United States Patent
Marras et al.

(10) Patent No.: US 11,542,547 B2
(45) Date of Patent: Jan. 3, 2023

(54) MULTIPLEX NUCLEIC ACID ASSAY METHODS CAPABLE OF DETECTING CLOSELY RELATED ALLELES, AND REAGENTS THEREFOR

(71) Applicant: Rutgers, The State University of New Jersey, New Brunswick, NJ (US)

(72) Inventors: Salvatore A. E. Marras, Roselle Park, NJ (US); Diana Vargas-Gold, Millburn, NJ (US); Sanjay Tyagi, New York, NY (US); Fred Russell Kramer, Riverdale, NY (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 216 days.

(21) Appl. No.: 16/091,824

(22) PCT Filed: Apr. 5, 2017

(86) PCT No.: PCT/US2017/026088
§ 371 (c)(1),
(2) Date: Oct. 5, 2018

(87) PCT Pub. No.: WO2017/176852
PCT Pub. Date: Oct. 12, 2017

(65) Prior Publication Data
US 2019/0225999 A1    Jul. 25, 2019

Related U.S. Application Data

(60) Provisional application No. 62/319,332, filed on Apr. 7, 2016.

(51) Int. Cl.
| | | |
|---|---|---|
| *C12Q 1/6858* | (2018.01) |
| *C12Q 1/6853* | (2018.01) |
| *C12Q 1/686* | (2018.01) |
| *C12Q 1/68* | (2018.01) |
| *C12P 19/30* | (2006.01) |
| *C12Q 1/6876* | (2018.01) |

(52) U.S. Cl.
CPC ............ *C12Q 1/6858* (2013.01); *C12P 19/30* (2013.01); *C12Q 1/68* (2013.01); *C12Q 1/686* (2013.01); *C12Q 1/6853* (2013.01); *C12Q 1/6876* (2013.01); *C12Q 2537/143* (2013.01); *C12Q 2600/16* (2013.01)

(58) Field of Classification Search
CPC ............................ C12Q 1/6853; C12Q 1/6858
See application file for complete search history.

(56) References Cited

U.S. PATENT DOCUMENTS

| | | |
|---|---|---|
| 2006/0141518 A1 | 6/2006 | Lao et al. |
| 2008/0280292 A1 | 11/2008 | Wangh et al. |
| 2016/0032373 A1 | 2/2016 | Whitman et al. |

FOREIGN PATENT DOCUMENTS

| | | |
|---|---|---|
| WO | 2014124290 A1 | 8/2014 |
| WO | 2015038634 A2 | 3/2015 |
| WO | 2015185902 A1 | 12/2015 |
| WO | 2016014921 A1 | 1/2016 |

OTHER PUBLICATIONS

Chevet, Low concentrations of tetramethylammonium chloride increase yield and specificity of PCR, Nucleic Acids Research, 23(16): 3343-3344, 1995. (Year: 1995).*
NPL_Gene Link, Inc.: PGR Additives & Enhancers, Dec. 31, 2014, Retrieved from Internet: <URL: https://www.genelink.com/Literature/ps/M40-3021-PCR_Additives_Ver5.1.pdf>.
Hung, et al: "A Specificity Enhancer for Polymerase Chain Reaction", Nucleic Acids Research, 1990, vol. 18, No. 16, 4953.
Chevet, et al: "Low Concentrations of Tetramethylammonium Chloride Increase Yield and Specificity of PCR", Nucleic Acids Research, 1995, vol. 23, No. 16, pp. 3343-3344.
Kovarova, et al: "New Specificity and Yield Enhancer of Polymerase Chain Reactions", Nucleic Acids Research, 2000, vol. 28, No. 13, e70.

* cited by examiner

*Primary Examiner* — Samuel C Woolwine
*Assistant Examiner* — Carolyn L Greene
(74) *Attorney, Agent, or Firm* — Fox Rothschild LLP

(57) ABSTRACT

This invention discloses multi-part primers for primer-dependent nucleic acid amplification methods. Also disclosed are multiplex assay methods, related reagent kits, and oligonucleotides for such methods.

17 Claims, 21 Drawing Sheets

Specification includes a Sequence Listing.

MULTIPLEX NUCLEIC ACID ASSAY METHODS CAPABLE OF DETECTING CLOSELY RELATED ALLELES, AND REAGENTS THEREFOR

CROSS REFERENCE TO RELATED APPLICATION

This application claims priority of U.S. Provisional Application No. 62/319,332 filed on Apr. 7, 2016. The content of the application is incorporated herein by reference in its entirety.

FIELD OF THE INVENTION

This invention relates to nucleic acid amplification and detection assays, for example, PCR amplification and detection methods, and to primers, reaction mixtures and kits for such methods.

BACKGROUND OF THE INVENTION

It has been a long-sought medical goal to be able to detect at a very early stage extremely rare mutations whose presence in a clinical sample is useful for diagnosing cancer, determining prognosis, and indicating the choice of effective therapy. The detection and quantitative assessment of relevant somatic mutations has multiple uses, including: (i) the detection of cancer at a treatable stage in patients who inherit genes that make cancer more likely; (ii) the detection of mutations in benign cancer cells that indicate that they may now metastasize; (iii) measurement of the abundance of cancer cells during treatment; and (iv) the determination as to whether drug-resistant cancer cells have arisen during treatment, so that therapy can be adjusted. A further goal is to develop methods that enable multiplex assays that can simultaneously measure the abundance of different rare mutations. If such assays were to become available, cancer could potentially be converted from an often-fatal disease to a chronic condition that can be managed by frequent testing combined with individualized therapeutic adjustments.

Spurring on these efforts is the realization that cancer cells, no matter where in the body they are located, divide frequently, undergo apoptosis and necrosis, as a consequence of which genomic DNA fragments from those cancer cells are present in each patient's blood plasma. This realization has opened up the possibility that the presence of rare mutations indicative of cancer diagnosis, prognosis, and treatment can be detected and quantitated at a very early stage, by performing "liquid biopsies," utilizing DNA isolated from plasma. The challenge facing assay designers is to find a means of selectively detecting and quantitating these rare mutant sequence fragments in plasma DNA, despite the presence of abundant related wild-type sequence fragments originating from normal cells throughout the body, and despite the fact that different relevant mutations, though originating in different cells, often occur in the same or adjacent codons. The success of "next-generation" sequencing for the detection of rare mutant sequence fragments in plasma DNA, though complex and costly, has illustrated the value of this approach (see, for example, Murtaza et al. (2013) Nature 497:108-112).

Molecular diagnostic assays based on the exponential amplification of nucleic acid target sequences, such as polymerase chain reactions, are inexpensive and sufficiently sensitive to generate signals from as little as a single template molecule. Conventionally, specificity is obtained by making a primer sufficiently long so that under the amplification reaction conditions, primarily during the primer-annealing step, the primer goes to only one place in a nucleic acid strand. For distinguishing between or among target sequences, allele-specific hybridization probes such as molecular beacon probes are commonly used. If the sequence being investigated is an allele, such as a single-nucleotide polymorphism (SNP) that is present in a mixture with another allele, for example, a wild-type (WT) variant, distinguishing by use of a probe has a practical detection limit of about 3% (allele selectivity of not less than about 300 target allele molecules in the presence of 10,000 molecules of the alternate allele) due to the tendency of amplification of the prevalent allele to overwhelm amplification of the rare allele.

Researchers have turned to modifying amplification primers to improve the selectivity of amplification assays. A primer that is highly allele-selective enables the exponential amplification of a mutant DNA sequence while simultaneously suppressing amplification of a far more abundant wild-type sequence that is present, even when the difference between them is a SNP. Simply shortening a conventional amplification primer will improve its allele-selectivity, but because that improvement comes at the expense of specificity, it is of limited value for analyzing mixtures of alleles. Other modifications of primers have been developed to improve their selectivity while retaining specificity. One such approach is ARMS ("amplification refractory mutation system"). An ARMS primer has a 3'-terminal nucleotide that is complementary to the sequence variant being investigated, but that is mismatched to another allele or alleles. See Newton et al. (1989) Nucleic Acids Res. 17:2503-2516; and Ferrie et al. (1992) Am. J. Hum. Genet. 51:251-262. ARMS relies on the refractory nature of certain DNA polymerases, that is, a tendency not to extend a primer-target hybrid having such a mismatch. ARMS has been demonstrated to be useful for determining zygosity (homozygous WT, heterozygous, or homozygous mutant (MUT)), but it has a practical detection limit for other uses of about 1% (not less than about 100 target allele molecules in the presence of 10,000 molecules of the alternate allele).

Other approaches seek to reduce the likelihood that a primer for a mutant sequence will hybridize to a mutant sequence and lead to its amplification, but is unlikely to hybridize to the corresponding wild-type sequence, thereby suppressing its amplification. Several primer designs have in common that they possess a priming sequence that is perfectly complementary to a mutant target, but contain an internal interrogating nucleotide that mismatches the corresponding wild-type sequence. Among such designs are dual priming oligonucleotide (DPO) primers, MyT primers, hairpin primers, and PASS primers. The length of their priming sequence is chosen so that, under annealing conditions, perfectly complementary mutant hybrids are likely to form, and are therefore likely to lead to the generation of amplicons, while mismatched wild-type hybrids are much less likely to form, and are therefore much less likely to lead to the generation of amplicons. Alternative approaches, involving PCR-clamping or the use of hairpin oligonucleotide blockers, utilize a mixture that contains both conventional DNA primers that bind to mutant sequences, and "anti-primers" that are designed to bind selectively to wild-type sequences, thereby preventing the initiation of wild-type amplicon synthesis. However, all of these approaches, though generally applicable for the detection of mutant sequences, are either not sufficiently sensitive to detect extremely rare mutants, not compatible with real-time PCR due to the presence of unnatural nucleotides in their sequence, or have not been shown to enable quantitative determinations in multiplex real-time PCR assays when different target mutations occur in the same codon.

We have developed multi-part primers that we refer to as "SuperSelective" primers whose structure and use in PCR assays is described in copending patent application PCT/US2014/015351, published 14 Aug. 2014 as WO 2014/124290 A1. We described real-time monoplex PCR assays in which SuperSelective primers were both "specific" (went to the correct place in the genome), and highly "selective" (rejected wild-type or other abundant sequences similar to the target sequence). We described real-time monoplex PCR assays utilizing plasmid DNA and a SuperSelective primer that successfully detected as few as 10 mutant alleles in a mixture containing 1,000,000 wild-type alleles, and we described a real-time monoplex PCR assay utilizing human DNA and a SuperSelective primer that successfully detected 10 mutant alleles in a sample containing 10,000 wild-type alleles although a plot of $C_T$ values versus the log of the starting number of mutant copies (templates) departed from linearity below 100 copies. We did not, however, demonstrate multiplex assays or describe multiplex assays for closely related rare mutant target sequences in which the SuperSelective primer design and the method were capable of detecting as few as ten mutant target sequences.

SUMMARY OF THE INVENTION

This invention includes multiplex assay methods that are capable of detecting in a sample containing genomic DNA fragments as few as ten copies of each of at least two different closely related, intended rare mutant DNA target sequences in the presence of 10,000 copies of a related wild-type target sequence where the mutant target sequences differ from each other and from their related wild-type sequence by as little as a single-nucleotide polymorphism (SNP). Intended target mutations are "closely related" if they occur in the same codon or in adjacent codons of the same gene, irrespective of whether those closely related target mutations occur on different sister chromosomes in the same cell, or whether they occur in chromosomes in different cells. Closely related mutations may differ from one another and from their related wild-type sequence by as little as a single-nucleotide difference. A single-nucleotide difference between a related wild-type sequence and a closely related mutant sequence is often referred to as a single-nucleotide polymorphism or SNP.

A first aspect of the invention is a multiplex assay method that is capable of amplifying and detecting in a sample as few as ten copies of each of at least two different closely related, intended rare mutant DNA target sequences in the presence of 10,000 copies of a related wild-type DNA target sequence, where the mutant DNA target sequences differ from each other and from the wild-type DNA target sequence by as little as a single-nucleotide polymorphism, comprising:

(a) preparing a non-symmetric primer-dependent amplification reaction mixture that includes the sample, a DNA polymerase, deoxyribonucleoside triphosphates, other reagents required for amplification, a distinguishably labeled homogeneous fluorescence detection probe, that is specific for an amplification product of each rare mutant DNA target sequence, an excess concentration of a reverse primer for the closely related mutant target sequences, and a limiting concentration of a unique multi-part primer for each intended rare mutant target sequence, wherein the sequence of each multi-part primer comprises, in the 5' to 3' direction, the following four contiguous DNA sequences that are copied by extension of the reverse primer:

a tag DNA sequence that is not complementary to any target DNA sequence, whose complement in an amplicon strand initiated by the reverse primer is the target of the probe and that is unique for each target sequence or target-sequence group that is to be separately identified;

an anchor DNA sequence that is sufficiently long so that it is able to hybridize with the closely related mutant DNA target sequences and with the related wild-type DNA target sequence during primer annealing;

a unique bridge DNA sequence at least six nucleotides long that does not hybridize during primer annealing to the unique multi-part primer's intended DNA target sequence, to any other closely related mutant target DNA sequences, or to the related wild-type DNA target sequence during primer annealing; and a unique foot DNA sequence that is 7 to 14 nucleotides long and that is perfectly complementary to the intended DNA target sequence but mismatches each other mutant DNA target sequence and the related wild-type DNA sequence by one or more nucleotides, at least one of which is the 3'-terminal nucleotide or the 3'-penultimate nucleotide, wherein:

(i) if the anchor DNA sequence and the foot DNA sequence of the multi-part primer are both hybridized to its intended target DNA sequences, thereby creating a primer-target hybrid, the primer-target hybrid comprises in the 5' to 3' direction of the multi-part primer: an anchor-target hybrid, a bubble, and a foot-target hybrid, said bubble having a circumference of 18 to 40 nucleotides and being formed by an intervening DNA sequence in the target DNA sequence that is at least eight nucleotides long and does not hybridize to the bridge DNA sequence during primer annealing, (ii) the bubble isolates the foot-target hybrid from the anchor-target hybrid, and the isolated foot-target hybrid is a weak hybrid that makes copying the intended target DNA sequence unlikely as evidenced by a delay of at least five cycles in the threshold value ($C_T$) as compared to the $C_T$ that would occur using a conventional primer (i.e., a DNA sequence that is 15-40 nucleotides long that is substantially complementary to a portion of the DNA sequence to be amplified that does not contain the target of the foot sequence) and forms a hybrid under primer annealing conditions;

(iii) the probability that during PCR amplification the multi-part primer for its intended target DNA sequence will initiate copying of any closely related mutant target DNA sequence or the related wild-type target DNA sequence is at least 1,000 times lower than the probability of initiating copying of its intended target sequence, as evidenced by a difference in threshold values ($\Delta C_T$) of at least ten thermal cycles;

(iv) the multi-part primer that has generated an amplicon strand has bridge and foot DNA sequences that are perfectly complementary to the amplicon strand's complementary strand; and (v) the length and sequence of the bridge DNA sequence of each multi-part primer, together with the length of the intervening DNA sequence of its intended target DNA sequence, result in a threshold value ($C_T$) observed for a sample containing only ten copies of its intended target DNA sequence that will occur within 60 cycles of exponential amplification and will be distinguishable from the $C_T$ observed from a sample containing no copies; and (b) repeatedly cycling the reaction mixture to amplify the closely related rare mutant target DNA sequences present in the sample and detecting the presence of those DNA sequences by measuring an intensity of fluorescence from each distinguishably labeled probe by real-time or end-point detection.

In one embodiment of the multiplex assay method, the cycling is temperature cycling in a polymerase chain reaction (PCR) method.

In one embodiment of the multiplex assay method, the amplification reaction mixture does not contain an allele-selectivity-enhancing reagent, and the foot DNA sequence of each multipart primer is 7-9 nucleotides long.

In one embodiment of the multiplex assay method, the amplification reaction mixture contains tetramethylammonium chloride (TMAC) or another allele-selectivity-enhancing reagent, and the foot DNA sequence of each multi-part primer is 8-10 nucleotides long.

In one embodiment of the multiplex assay method, the foot DNA sequence mismatches the closely related wild-type DNA sequence by one or more nucleotides, and wherein at least one of which is the 3'-terminal nucleotide.

In one embodiment of the multiplex assay method, a $C_T$ value for one target DNA sequence represents the same number of starting templates as it does for any other target DNA sequence.

In one embodiment of the multiplex assay method, the multiplex assay method includes amplifying and detecting a reference wild-type DNA sequence that is not closely related to the at least two closely related mutant target DNA sequences, wherein the primer-dependent amplification reaction mixture includes a limiting multi-part primer for, an excess reverse primer for, and a homogeneous fluorescence detection probe for, the reference DNA sequence, wherein the multi-part primer for the reference DNA sequence has the structural and functional limitations described in the first aspect set forth above, and wherein the length and nucleotide sequence of the bridge DNA sequence of the multi-part primer for the reference DNA sequence are coordinated with those of the multi-part primers for the mutant target DNA sequences so that the difference between the $C_T$ value obtained for each mutant target DNA sequence and the $C_T$ value obtained for the reference wild-type DNA sequence reflects the abundance of that mutant target DNA sequence relative to the abundance of the reference wild-type DNA sequence, irrespective of the amount of DNA present in the sample.

In one embodiment of the multiplex assay method, cycling the reaction mixture is performed by an instrument, wherein the number of target DNA sequences exceeds the number of colors the instrument can separately detect, and wherein multiple different probes are thermospecific hybridization probes having the same fluorophore but having different melting temperatures.

In one embodiment of the multiplex assay method, amplification and detection are a digital PCR method, and wherein the probes are color-coded molecular beacon probes.

In one embodiment of the multiplex assay method, amplification and detection are performed in a spectrofluorometric thermal cycler, and wherein the probes are color-coded molecular beacon probes.

In one embodiment, the multiplex assay method is capable of amplifying and detecting fewer than ten copies of any of the at least two closely related rare mutant target DNA sequences, wherein the hybrids formed by the multi-part primer anchor DNA sequences and the mutant target DNA sequences have melting temperatures (Tm's) that are lower than the Tm of hybrids formed by the reverse primer and the mutant target DNA sequences, wherein before step (b) multiple cycles of linear amplification utilizing the reverse primer are performed using a primer annealing temperature at which the reverse primer hybridizes but the multi-part primers are very unlikely to hybridize, and wherein step (b) is performed using a lower primer annealing temperature at which the multi-part primers and the reverse primer hybridize.

Assay methods according to this invention comprise selectively amplifying each closely related mutant sequence, if present in the sample, by a non-symmetric primer-dependent amplification method, such as a polymerase chain reaction (PCR) method, and separately detecting amplified products (amplicons) from each mutant target sequence by fluorescence detection that utilizes at least one fluorescently labeled probe. Methods according to this invention may be qualitative or quantitative. In some quantitative methods, the real-time PCR threshold value (or threshold cycle, $C_T$) reflects the amount of a mutant target sequence present in a sample. Certain embodiments further include amplifying a reference wild-type gene sequence, which may be the wild-type sequence related to the mutant sequences to be detected or a reference wild-type sequence that is present in the sample but is unrelated to those mutant sequences.

Assay methods according to this invention utilize SuperSelective primers having 5'-tag sequences that serve as targets for detection by fluorescently labeled hybridization probes. By including unique 5'-tag sequences (each different from all other 5'-tag sequences in a particular assay) in different SuperSelective primers, and including a distinguishably labeled probe targeting the complement of each different 5'-tag sequence, detecting probe hybridization identifies which tag sequence, and hence which SuperSelective primer, was amplified. Preferred hybridization probes are homogeneous detection probes whose hybridization is detectable without washing away unbound probes. Preferred fluorescent labels are fluorophores. Our most preferred homogeneous detection probes are molecular beacon probes labeled with at least one fluorophore and also labeled with a non-fluorescent quencher.

Assay methods according to this invention are multiplex assays that are capable of detecting in a sample containing genomic DNA fragments the presence of at least two closely related mutations of a selected wild-type sequence in the presence of an abundance of the wild-type sequence. Different embodiments have different objectives and features.

Certain embodiments have as their objective the detection of any one or more of several closely related mutations that may be present in a sample. Reaction mixtures for such assays include a different SuperSelective primer for each mutant target sequence, and optionally an unrelated wild-type gene sequence for the purpose of quantitation, wherein each SuperSelective primer has a different 5'-tag sequence whose complement is the target for a distinguishable fluorescent probe. Many such embodiments include homogeneous detection utilizing a different homogeneous detection probe (a probe whose hybridization to its target in the assay is detectable), preferably a different molecular beacon probe, for each target sequence. We prefer that each different molecular beacon probe be specific for the complement of a different 5'-tag sequence and be labeled with a fluorophore that is distinguishable from other fluorescent probes in the reaction. Such methods typically are performed in a spectrofluorometric thermal cycler, which limits the number of distinguishable colors (commonly used thermal cyclers are 5-color instruments) to a maximum of eight or sometimes ten. Other embodiments have as their objective the detection of any one or more groups of mutations, where the presence of one or more mutations in a group is technically significant, for example, significant regarding treatment of a cancer patient. Such methods typically are performed in a spectrofluorometric thermal cycler, which limits the number of distinguishable colors (commonly used thermal cyclers are 5-color instruments) to a maximum of ten. Reaction mixtures for such assays include a different SuperSelective primer for each mutant target sequence, and optionally an unrelated wild-type gene sequence for the purpose of quantitation, wherein each SuperSelective primer in a group has the same 5'-tag sequence, and each group has a different 5'-tag sequence; and reaction mixtures include a distinguishably different fluorophore-labeled hybridization probe targeting the complement of each different 5'-tag sequence, preferably a homogeneous detection probe whose hybridization is detectable without washing away unbound probes, most preferably a molecular beacon probe.

Yet other embodiments are multiplex assays that have the capability of detecting any one or more mutant target sequences, or groups of target sequences, from among a number that exceeds the number of colors of a spectrofluorometric thermal cycler. Certain of these embodiments employ what we refer to as "thermospecific" hybridization probes, preferably molecular beacon probes, whose probe-target hybrids have different melting temperatures (Tm's). For example, if a liquid biopsy sample is to be tested on a five-color spectrofluorometric thermal cycler for the presence of one or more of 35 different target sequences, 35 different SuperSelective primers, each specific for a different target sequence, can be divided into five sets of seven. All seven in each of the five sets have 5' tags whose complementary sequences are targets for seven different thermospecific hybridization probes, such as molecular beacon probes, all of which are labeled with the same fluorophore but all of which produce probe-target hybrids having distinguishable Tm's. Thus, each one of the 35 different target sequences, if present, can be identified by a combination of fluorescence color and Tm determined in a post-amplification (end-point) thermal analysis.

Yet other embodiments are screening assays, a type of multiplex assay whose objective is to determine which mutant target sequence from a list of many different mutant target sequences is present in a sample, or to determine that none of those mutant target sequences are present in that sample. In these assays, whichever mutant target sequence is present is exponentially amplified, preferably in a polymerase chain reaction, and the resulting amplicons (which are only generated if a mutant target sequence was present in the sample) are detected with fluorescently labeled hybridization probes. In such embodiments there is for each possible mutant target sequence a SuperSelective primer having a different 5'-tag sequence. Usually, the number of mutant target sequences on the list exceeds the number of different fluorescent colors that the detection instrument can distinguish, and when this occurs there is a different color-coded molecular beacon probe present in the assay for detecting each of the different 5'-tag sequence complements that can become incorporated into the resulting amplicons (see International Patent Publication WO 2004/099434 A3 for a description of color-coded molecular beacons). The use of SuperSelective primers in these screening assays enables rare mutant target sequences to be detected without interference from abundant related wild-type sequences.

Yet other embodiments are digital PCR assay methods, including assays carried out in many different reaction wells in a thermal cycler, and droplet digital PCR (ddPCR) assays carried out in many different droplets in a thermal cycler; and in both cases detection of the resulting amplicons is often carried out in a separate detection instrument, for example The Bio-Rad QX200™ Droplet Digital PCR System or the Stilla Technologies Naica™ System. Such methods utilize for each of numerous, say 15 or 35, target sequences a SuperSelective primer that has a 5'-tag sequence that is different from all other 5'-tag sequences in the reaction. For each of the different target sequences there is a color-coded molecular beacon probe that targets the complement of its 5'-tag sequence. Because digital PCR includes subdividing a reaction mixture into so many wells or droplets that each well or droplet is very likely to contain only one target molecule or no target molecule at all, such methods are quantitative.

The basic principal underlying digital PCR assays (illustrated here by a description of ddPCR) is that a sample can be diluted to such an extent that only one target DNA molecule is present in a droplet (or no target molecule is present in a droplet), and there are a large number of droplets. Then, simultaneous PCR amplifications are carried out in each droplet, and fluorescently labeled probes that are present in each droplet bind to the amplicons generated in that droplet (if it contained a target molecule), and become brightly fluorescent in a particular color code, indicating both that the droplet contained a target molecule and identifying which target sequence that was. The number of droplets that light up in the same color code provides an accurate measure of the number of the corresponding target molecules in the original sample; and this approach is so sensitive that even a single target molecule in a sample can be detected.

Classical droplet digital PCR has been used to detect and quantitate rare somatic mutations relevant to cancer diagnosis, prognosis, and therapy. See Sanmamed et al. (2015) Clin. Chem. 61:297-304. In order to separate the rare mutant target molecules from the much more abundant related wild-type molecules, more than a million droplets are required. See, for example, Hindson et al. (2011) Anal. Chem. 83:8604-8610. This large number of droplets is necessary because there are many more wild-type targets in a sample than the number of rare related mutant targets (which often only differ from the wild-type target by a single-nucleotide polymorphism), and because the probes (which are designed to bind to a subsequence within the amplicon that contains the mutation) occasionally bind to the corresponding sequence in the amplicons generated from the related wild-type targets, so it is desirable to have so many droplets that it is highly unlikely that a droplet that contains a mutant target will also contain one or more related wild-type targets. This assures that there will not be a droplet containing sufficient wild-type targets that the intensity of the signal generated in that droplet is similar to the intensity of the signal that would have been generated had that droplet contained the mutant target sequence, the consequence of which is that the droplet is mistakenly considered to contain the related mutant target. Put another way, had the original sample been divided into too few droplets, then droplets containing some wild-type target sequences and no related mutant target sequence will be mistaken for droplets containing mutant target.

However, when digital PCR embodiments employing SuperSelective primers are carried out to detect rare mutant target molecules in a sample, far fewer droplets (for example, only 20,000 to 30,000 droplets) are needed, because SuperSelective primers do not generate detectable amplicons from the relatively few related wild-type DNA molecules that may also be present in a droplet. In such digital PCR assays, detection may occur in a thermal cycler, in a flow cytometer, or with a microscope.

For selectively amplifying closely related mutant sequences, methods according to this invention utilize a different multi-part primer, which we call a "SuperSelective" primer, for each of the mutant target sequences and a common reverse primer, which preferably is a conventional PCR primer. For also amplifying the related wild-type sequence, methods according to this invention utilize a SuperSelective primer for that sequence and the same common reverse primer. For also amplifying an unrelated sequence, for example an unrelated mutant or wild-type sequence, methods according to this invention utilize a SuperSelective primer and a separate reverse primer for that sequence.

SuperSelective primers are multi-part oligodeoxyribonucleotides whose function in PCR amplification is divided into two parts. The function of efficiently binding to a gene of interest is assigned to a relatively long sequence segment (which we call the "anchor sequence" or "anchor"), and the function of selectively binding to a nearby subsequence within that gene that contains the mutation to be detected, and then initiating the synthesis of an amplicon, is assigned to a separate, short 3' sequence segment (which we call the "foot sequence" or "foot"). Consonant with its function, the anchor sequence is designed to form a strong hybrid with the intended target sequence of the primer during the primer-annealing step of PCR cycles. In this regard, it is similar to a conventional PCR primer in function and length. The foot sequence is a short sequence segment that is perfectly complementary to the probe's intended target sequence but mismatched to closely related target sequences, whether closely related mutant target sequences or a related wild-type sequence, by one or more nucleotides. Each nucleotide in the foot that is mismatched to a closely related mutant target sequence or to the related wild-type sequence is an "interrogating nucleotide." In SuperSelective primers, the anchor is separated from the foot by an additional, in many embodiments relatively long, sequence segment (which we call the "bridge sequence" or "bridge"). The bridge is chosen so as to insure that it does not form secondary structures and is not complementary to the "intervening sequence" in the template molecule that joins the target sequence for the anchor to the target sequence for the foot. Consequently, when the primer is hybridized to a template molecule, the bridge sequence in the primer and the intervening sequence in the template form a single-stranded "bubble" that functionally separates the efficient formation of the anchor hybrid from the formation of the foot hybrid. The circumference of the bubble in nucleotides is: length of the bridge sequence plus length of the intervening sequence plus 4. The resulting primers are bifunctional: under primer-annealing conditions, the long 5' anchor sequence enables the primer to bind efficiently and specifically to the genomic region of interest present in the target DNA fragments, while the short 3'-foot sequence (which possesses the interrogating nucleotide or nucleotides), because it is tethered to the anchor sequence by the bridge sequence, is able to form a weak, perfectly complementary hybrid with its intended target sequence. Due to its short length, the foot is unlikely to form a considerably weaker, mismatched hybrid with a closely related target sequence, whether it is the related wild-type sequence or a different mutation of that sequence.

In PCR assays, the selective step occurs when a SuperSelective primer binds to a DNA template that is present in the original sample being analyzed. Once the foot sequence of a SuperSelective primer initiates the synthesis of an amplicon, the entire sequence of the SuperSelective primer (including the "artificial" bridge sequence) is incorporated into that (+) amplicon. In subsequent thermal cycles of exponential amplification, the resulting amplicons are amplified efficiently in the normal manner, with the entire SuperSelective primer sequence, or at least the bridge and foot sequences, serving as a long conventional primer that is completely complementary to the (−) amplicons.

In our copending patent application PCT/US2014/015351 (International Publication Number WO 2014/124290 A1, publication date 14 Aug. 2014) we disclosed SuperSelective primers generally and exemplified their use in monoplex symmetric PCR assays using detection with SYBR® Green, a dsDNA binding dye. As described there, a SuperSelective primer is a multi-part primer having three contiguous DNA sequences (in the 5' to 3' direction): an anchor sequence, a bridge sequence, and a foot sequence, and meeting certain structural and functional criteria, as follows:

The anchor sequence hybridizes during primer annealing to the mutant target sequence to be detected and also to the corresponding wild-type sequence, forming a hybrid that is typically 15-40 nucleotides long.

The foot sequence that is at least 5 nucleotides long, preferably 6-7 nucleotides long, and that is perfectly complementary to the mutant target sequence to be detected but mismatched to the corresponding wild-type sequence and another mutation of that wild-type sequence by one or two nucleotides.

The bridge sequence is at least 6 nucleotides long and does not hybridize during primer annealing to the mutant target sequence to be detected or to the corresponding wild-type sequence or to another mutation of that wild-type sequence.

If the anchor and foot sequences are hybridized to the mutant target sequence to be detected, there is in the target sequence an intervening sequence at least 8 nucleotides long that does not hybridize to the bridge sequence during primer annealing, the bridge and intervening sequences together creating a bubble in the hybrid having a circumference of 16-52 nucleotides.

The circumference of the bubble and the length of the foot result in a weak foot/target sequence hybrid that makes copying the intended target sequence unlikely, as evidenced by a delay in the threshold cycle ($C_T$) of, typically, from two to ten thermal cycles as compared to using a conventional PCR primer.

The probability that during PCR amplification begun with either $10^6$ copies of the mutant target sequence or $10^6$ copies of the corresponding wild-type sequence, a primer/wild-type sequence hybrid will be extended is at least 1,000 times lower than the probability that a primer/target sequence hybrid will be extended, as evidenced by a difference in threshold cycles ($\Delta C_T$) of at least 10 cycles, preferably at least 12 cycles.

For use in multiplex assay methods according to this invention such as described in Examples 6-10 below that are capable of detecting in a sample containing genomic DNA fragments as few as ten copies of each of at least two different closely related, intended rare mutant DNA target sequences in the presence of 10,000 copies of a related wild-type target sequence, the SuperSelective primer for each mutant target sequence is a multi-part primer that comprises, in the 5' to 3' direction, four contiguous DNA sequences that are copied by extension of the reverse primer. As used in Examples 6-10, those sequences are:

(1) The 5' segment of the multi-part primer sequence is a tail that does not hybridize to any target sequence in a sample during primer annealing. Each tail in a multiplex assay is unique. Its complement that is made by extension of the common reverse primer serves as a target for a fluorophore-labeled probe. We refer to the tail as a "tag sequence" or "tag". The tag is sufficiently long that its complement can serve as the probe's target. The probe is a homogeneous detection probe whose hybridization leads to a detectable fluorescent signal. Types of such a probe are well known. They include at least one oligonucleotide that is labeled with a fluorophore. The probe may be, for example, a molecular beacon probe, a TaqMan® probe, a FRET probe (a fluorophore-labeled donor oligonucleotide and a fluorophore-labeled or quencher-labeled acceptor oligonucleotide), a yin-yang probe, a Resonsense probe, or an Eclipse probe. Our preferred detection probe is a molecular beacon probe.

(2) Immediately adjacent to the tag sequence is the anchor sequence, which is described above. The anchor sequence is sufficiently long that during PCR amplification, it hybridizes during the primer annealing step of a PCR cycle. The anchor sequence is sufficiently long so that it forms a strong hybrid under primer annealing conditions, being similar in that regard to a conventional PCR primer. SuperSelective primers for closely related mutant target sequences may include the same anchor sequence, or their anchor sequences may be slightly different. The same applies for a SuperSelective primer for the related wild-type sequence, if such a primer is included.

(3) Immediately adjacent to the anchor sequence is the bridge sequence. The bridge sequence is a unique sequence that does not hybridize to the primer's mutant target sequence or to any closely related target sequence, either a closely related mutant target sequence or the related wild-type sequence. In SuperSelective primers utilized in methods of this invention the bridge is at least six nucleotides long. It is not more than 18 nucleotides long, generally not more than 15 nucleotides long and in certain preferred embodiments 9-13 nucleotides long. When the anchor sequence is hybridized to a target sequence, the bridge sequence is opposite to, but does not hybridize with, a sequence in the target that we refer to as the "intervening sequence," further described below.

(4) Immediately adjacent to the bridge sequence and constituting the 3' end of the primer is the foot sequence. In SuperSelective primers utilized in methods of this invention as described in Examples 6-10 the foot sequence is a unique sequence that is 6-10 nucleotides long, preferably 7-9 nucleotides long and that is perfectly complementary to the primer's intended mutant target sequence but mismatches each other closely related target sequence, either a mutant target sequence or the related wild-type target sequence, by one or more nucleotides, which we refer to as "interrogating nucleotides." At least one interrogating nucleotide is the 3'-terminal nucleotide of the foot sequence or the nucleotide adjacent thereto (the 3'-penultimate nucleotide). The bridge sequence and the foot sequence do not together prime any other closely related rare mutant target sequence, their corresponding wild-type target sequence, or any non-target sequence in the mixture during primer annealing.

For use in assay methods according to this invention such as described in Examples 11-15 below that include the use of an allele-selectivity enhancing reagent and that are capable of detecting in a sample containing genomic DNA fragments fewer than ten copies of each of at least two different closely related, intended rare mutant DNA target sequences in the presence of 10,000 copies of a related wild-type target sequence, the SuperSelective primer sequences, surprisingly, are somewhat different. While the 5'-tag sequence and the anchor sequence remain as described above, there is more flexibility in the lengths of the bridge and foot sequences. A short foot sequence, for example 7-8 nucleotides long, can be used in combination with a long bridge sequence, for example, 18 nucleotides long and a consequently larger bubble circumference; and conversely, a longer foot sequence, for example 9-10 nucleotides long, can be used in combination with a short bridge sequence, for example 10 nucleotides long, and a consequently shorter bubble circumference. We have discovered that the optimum amount of the allele-selectivity enhancing reagent tetramethylammonium chloride (TMAC) is different in each of these cases. When TMAC is used, the length of the foot should be 7-14 nucleotides long and the circumference should be 24-40 nucleotides long.

Methods according to this invention comprise preparing a non-symmetric primer-dependent amplification mixture, such as a polymerase chain reaction (PCR) amplification mixture that includes the sample that contains or may contain at least two closely related mutant DNA target sequences; a DNA polymerase, deoxyribonucleoside triphosphates, and other reagents required for amplification; for each closely related target sequence to be amplified and detected, a unique SuperSelective primer as described above, in limiting concentration; a common conventional reverse primer for the closely related target sequences, in excess concentration; and for each closely related target sequence to be amplified and detected, a distinguishably labeled fluorescence detection probe, preferably a homogeneous fluorescence detection probe, most preferably a molecular beacon probe, that is specific for the complement of the tag of the SuperSelective primer for that target sequence. For embodiments using an allele-selectivity enhancing reagent, for example TMAC, the amplification mixture also includes an effective concentration, preferably an optimized concentration, of that reagent. Preparation of such a reaction mixture may include reverse transcribing RNA templates where appropriate. Methods according to this invention include subjecting the reaction mixture to multiple thermal cycles for amplification of the intended target sequences by a polymerase chain reaction (PCR) amplification, and detecting the presence of amplified products (amplicons) by measuring the intensity of fluorescence from each distinguishably labeled probe by real-time detection.

In PCR amplification with real-time detection, the fluorescence intensity of a probe's fluorophore is observed during multiple thermal cycles, for example, during the step of primer annealing. The threshold cycle ($C_T$) is the cycle of exponential amplification at which fluorescence intensity from the probe becomes detectable above background fluorescence. The concentration of each SuperSelective limiting primer is sufficient to obtain a $C_T$ during exponential amplification utilizing both the SuperSelective primer and the common reverse primer. The common reverse primer is in excess concentration, so that additional PCR thermal cycles after each SuperSelective primer has been used up produces single-stranded amplicons that contain the complement of the SuperSelective primer's tag. In methods of the invention that additionally distinguish among identically labeled probes, for example molecular beacon probes, by differences in their melting temperatures (Tm's), a post-amplification melt analysis is included.

In methods of this invention, when the anchor sequence and the foot sequence of a multi-part primer are both hybridized to the primer's intended target sequence in the sample, the bubble isolates the foot-sequence hybrid from the anchor-sequence hybrid, and the isolated foot-sequence hybrid is a weak hybrid that makes copying the intended target sequence unlikely as evidenced by a delay of at least five cycles in the threshold value ($C_T$) as compared to the $C_T$ that would occur using a conventional primer. The length and sequence of the bridge sequence of each multi-part primer, together with the length of the intervening sequence of its intended target sequence in the sample, result in a threshold value ($C_T$) observed for a sample containing as few as ten copies of its intended target sequence within 50 cycles of exponential amplification, and that $C_T$ is distinguishable from the $C_T$ observed from a sample containing no copies of its intended target. A hybrid that might or does form between the foot sequence and another closely related target sequence, either a closely related mutant sequence or the related wild-type sequence, is even weaker. In methods of this invention, the probability that during PCR amplification the SuperSelective primer for one intended target sequence will initiate copying of any closely related mutant target sequence or the related wild-type target sequence is at least 1,000 times lower than the probability of initiating copying of its intended target sequence, as evidenced by a difference in threshold values ($\Box C_T$) of at least 10 thermal cycles.

In certain preferred embodiments of the foregoing methods of this invention, a $C_T$ value for one target sequence represents the same number of starting templates as it does for any other target sequence.

Certain embodiments of the foregoing methods of this invention include amplifying and detecting a reference wild-type sequence that is related to the at least two closely related mutant target sequences. In such embodiments the reaction mixture, for example, the PCR assay mixture, includes a SuperSelective primer that is useful in methods of this invention (as described above) in limiting concentration for the related reference target sequence. Amplification of the reference sequence employs the same reverse primer as does amplification of the closely related mutant target sequences. The reaction mixture further includes a homogeneous fluorescence detection probe (as described above) whose target is the complement of the tag of the SuperSelective primer for the wild-type sequence.

Certain preferred embodiments of the foregoing methods of this invention include amplifying and detecting a reference wild-type sequence that is not related to the at least two closely related mutant target sequences. In such embodiments the reaction mixture includes a SuperSelective primer that is useful in methods of this invention (as described above) in limiting concentration and a separate conventional reverse primer in excess concentration for the unrelated reference sequence.

This invention also includes adding to reaction mixtures for the embodiments of methods described above an allele-selectivity enhancing reagent, for example, TMAC.

Certain embodiments of the foregoing methods of this invention are capable of amplifying and detecting fewer than ten copies of the at least two closely related rare mutant target sequences. In some embodiments the hybrids formed by multi-part primer anchor sequences and the mutant target sequences have melting temperatures (Tm's) that are lower than the Tm of hybrids formed by the common reverse primer and the mutant target sequences. PCR amplification is preceded by multiple cycles of linear amplification utilizing only the reverse primer at a primer annealing temperature at which the common reverse primer hybridizes but the multi-part primers rarely hybridize. Then, subsequent cycles of exponential amplification are performed using a lower primer annealing temperature at which the multi-part primers and the common reverse primer hybridize.

This invention also includes reagent kits that include reagents sufficient for performing amplification and detection according to any of the foregoing methods.

This invention also includes sets of oligonucleotides that includes primers and probes required for performing amplification and detection according to any of the foregoing methods.

DETAILED DESCRIPTION

Figure 1:
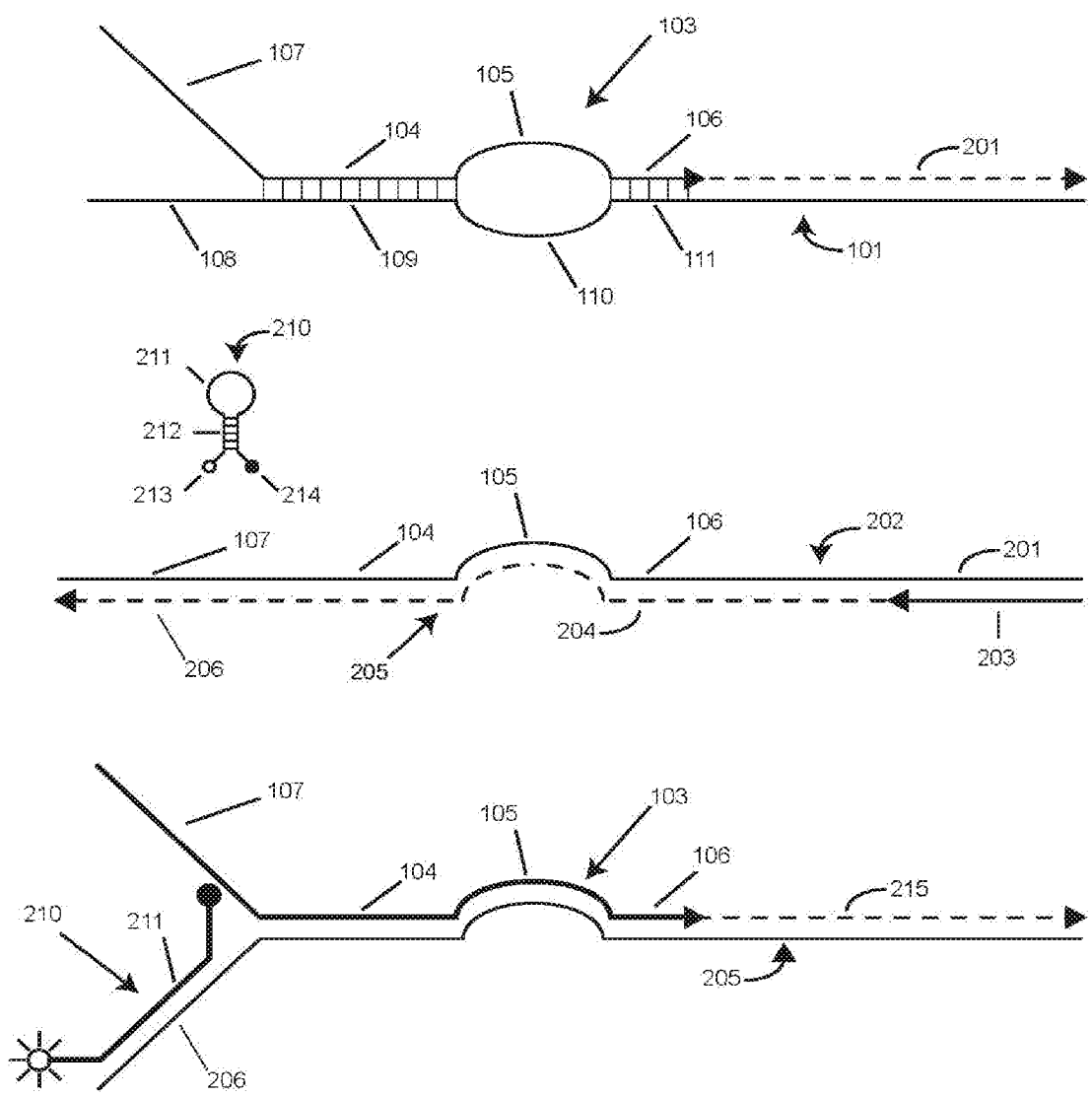
FIG. 1 is a schematic representation of a SuperSelective primer according to this invention and its copying and detection during PCR amplification.

Assays according to this invention are primer-dependent amplification and detection methods such as, for example, PCR amplification and detection methods. Methods according to this invention are multiplex assays that are capable of detecting in a sample containing genomic DNA fragments the presence of at least two closely related mutations of a selected wild-type sequence in the presence of an abundance of the related wild-type sequence. Reaction mixtures utilized in such methods include a SuperSelective primer for each mutant target sequence.

Primer-dependent amplification reactions useful in methods of this invention may be any suitable exponential amplification method, including the polymerase chain reaction (PCR), the ligase chain reaction (LCR), the nicking enzyme amplification reaction (NEAR), strand-displacement amplification (SDA), nucleic acid sequence-based amplification (NASBA), transcription-mediated amplification (TMA), and rolling circle amplification (RCA). Preferred methods utilize PCR. In non-symmetric PCR amplification methods, for example asymmetric PCR, one primer, the limiting primer, is present in a limiting amount so as to be exhausted prior to completion of amplification, after which linear amplification occurs, using the remaining primer, the excess primer. A non-symmetric PCR method useful in this invention is LATE-PCR (see, for example, European Patent EP 1,468,114; and Pierce et al. (2005) Proc. Natl. Acad. Sci. USA 102:8609-8614). In a non-symmetric amplification method according to this invention the multi-part primer is the limiting primer. Preferred methods also include digital PCR (see, for example, Vogelstein and Kinzler (1999) Proc. Natl. Acad. Sci. USA 98:9236-9241), where it is desirable to detect amplicons from a single mutant template molecule that is present in reactions that contain related wild-type molecules.

If the amplification reaction utilizes an RNA-dependent DNA polymerase (an example being NASBA), the amplification reaction is isothermal. We refer to repeated rounds of synthesis of amplified product as "cycles", but they are not thermal cycles. For such amplification the "intended target sequence" and the "unintended target sequence" that are primed by a multi-part primer according to this invention are RNA sequences that occur in an original sample and in the amplification reaction mixture, where they are present with the DNA polymerase and the multi-part primer.

If the amplification reaction utilizes a DNA-dependent DNA polymerase (an example being PCR), an original sample may contain either DNA or RNA targets. For such amplifications, the "intended target sequence" and the "unintended target sequence" that are primed by a multi-part primer that is useful in methods of this invention are DNA sequences that either occur in an original sample or are made by reverse transcribing RNA sequences that occur in the original sample. If the multi-part primer is used for reverse transcription, the "intended target sequence" and the "unintended target sequence" are RNA as well as cDNA. If a separate, outside primer is used for reverse transcription, the "intended target sequence" and the "unintended target sequence" are cDNA. In either case, the "intended target sequence" and the "unintended target sequence" are nucleic acid sequences that are present in the amplification reaction mixture with the DNA polymerase and the multi-part primer. Primer-dependent amplification reactions comprise repeated thermal cycles of primer annealing, primer extension, and strand denaturation (strand melting). Primer annealing may be performed at a temperature below the primer-extension temperature (for example, three-temperature PCR), or primer annealing and primer extension may be performed at the same temperature (for example, two-temperature PCR). The overall thermal profile of the reaction may include repetitions of a particular cycle, or temperatures/times may be varied during one or more cycles. For example, once amplification has begun and the priming sequence of a multi-part primer is lengthened, a higher annealing temperature appropriate for the longer primer might be used to complete the amplification reaction.

Although we describe in the examples set forth below assays in which there are two or three target sequences and two or three SuperSelective primers, multiplex assay methods of this invention may include more target sequences and more SuperSelective primers. For highly multiplexed assays that include more target sequences than there are colors that a spectrofluorometric thermal cycler can distinguish—occasionally a maximum of ten, sometimes a maximum of eight, but more typically five, methods of this invention include any of several ways to increase the capacity of an assay. One way is to utilize digital PCR methods, for example, whether droplet-based emulsion PCR or bead-based emulsion PCR, may be highly multiplexed. While it is expected that only one target sequence will be present in a particular amplification reaction (for example, in a droplet), the PCR mixture will contain a SuperSelective primer and a separate detection probe, for example, a molecular beacon probe, for each possible target. For numerous molecular beacon probes, where the number of different probes exceeds the number of differently colored fluorophores whose spectra can be distinguished by an instrument (typically not more than 7 or 8), a technique to increase the number of probes that can be identified may be employed. For example, as disclosed in published international patent application WO 2002/099434, and in U.S. Pat. Nos. 7,385,043 and 7,771,949, each probe can be coded with two or more colors by taking a quantity of the probe, dividing it into multiple aliquots, labeling each aliquot with a different fluorophore, and recombining the aliquots, whereby the probe is given a unique multi-color code. We refer to this process as "color coding" and to the resultant probes as "color-coded" molecular beacon probes. For example, starting with a panel of six distinguishable fluorophores, dividing the quantity of each probe into two aliquots, and labeling the two aliquots with different colors, fifteen different probes can be uniquely color-coded (if one adds six probes for which both aliquots are labeled with the same fluorophore, the number of uniquely colored probes increases to 21). Flow cytometry detection methods are well suited for detection in digital PCR droplets.

Another technique is to use "thermospecific" hybridization probes, preferably molecular beacon probes, wherein several different probes have the same fluorophore but are distinguishable by their Tm's. By performing a post-amplification melt, which can be done in a spectrofluorometric thermal cycler, probes of a given color can be distinguished from one another by Tm so as to enable identification of which probe is fluorescing.

Screening assays are multiplex assays in which it is expected that only one of many possible target sequences will be present in a sample. For amplification and detection using a spectrofluorometric thermal cycler, screening assays according to this invention utilize a different SuperSelective primer with a unique 5'-tag sequence for each of many (say 15 or 35) possible targets, and they use a uniquely color-coded molecular beacon probe, described above, for each different 5'-tag sequence.

FIG. 1 schematically depicts a SuperSelective primer useful in methods of this invention. In the top panel, SuperSelective primer 103 is shown hybridized to its intended target sequence 101. In the 5'-to-3' direction, primer 103 is a multi-part primer that includes four contiguous DNA sequences: 5' tag 107, anchor sequence 104, bridge sequence 105, and foot sequence 106. Tag sequence 107 is not complementary to the target sequence 101. When primer 103 is hybridized to target sequence 101, tag sequence 107 is opposite target sequence 108 but does not hybridize to it. Rather, tag 107 exists as a single-stranded tail (a "5' tail"). Anchor sequence 104 forms a sufficiently long hybrid, typically 15-40 nucleotides in length, with sequence 109 in target sequence 101 to efficiently bind primer 103 to target sequence 101 during primer annealing, as conventionally indicated by the short vertical lines between anchor sequence 104 and its binding site 109 (representing the pairing of complementary nucleotides). Anchor sequence 104 may be perfectly complementary to target sequence 101. It need not be perfectly complementary, however, as long as its functionality is maintained. Foot sequence 106 at the 3' end of primer 103 is perfectly complementary to sequence 111 of intended target sequence 101. If no allele-specificity-enhancing reagent is used, the foot sequence is 6-10 nucleotides long, preferably 7-9 nucleotides long, most preferably 7-8 nucleotides long. If an allele-specificity enhancing reagent is used, foot sequence 106 can be 7-14 nucleotides long, preferably 8-10 nucleotides long in some cases. Whereas anchor sequence 104 imparts specificity to primer 103 by binding to a sequence of interest in all target sequences, closely related mutants, and related wild-type, foot sequence 106 imparts selectivity by selectively hybridizing to its intended target sequence during primer annealing in favor of even sequences differing by only a single nucleotide (allele-selectivity). Separating anchor sequence 104 and foot sequence 106 is bridge sequence 105, which does not hybridize to target sequence 101. Bridge sequence 105 is a unique sequence that is 8-20 nucleotides long, does not form secondary structures, and is not complementary to target sequence 101 or to any closely related target sequence or to the related wild-type sequence. When anchor sequence 104 and foot sequence 106 are hybridized to strand 101, bridge sequence 105 is opposite unhybridized sequence 110 in target sequence 101, which we refer to as an "intervening" sequence. Intervening sequence 110 is at least 6 nucleotides long. Together, bridge sequence 105 and intervening sequence 110 form a single-stranded "bubble" whose circumference in nucleotides is the length of the bridge sequence plus the length of the intervening sequence plus 4. In methods according to this invention, the circumference of the bubble is in the range of 18-30 nucleotides or, if an allele-selectivity enhancing reagent is used, in the range of 18-40 nucleotides.

PCR amplification with multi-part primer 103 and conventional reverse primer 203 by the polymerase chain reaction is depicted in the three panels of FIG. 1. The top panel shows extension of primer 103 by a DNA polymerase utilizing intended mutant target strand 101 as a template to produce extension 201. This creates strand 202 (middle panel). The middle panel in FIG. 1 depicts what happens in the next amplification cycle. Conventional reverse primer 203 hybridizes to amplified product strand 202 and is then extended by the DNA polymerase using strand 202 as a template to produce extension 204. Primer 203 and extension 204 comprise amplicon strand 205 (bottom panel). It will be observed that extension 204 includes sequences perfectly complementary to all four contiguous sequences (tag, anchor, bridge, and foot) of primer 103. Sequence 206 in amplicon strand 205 is complementary to tag sequence 107 and serves as a binding site for homogeneous detection probe 210. Because tag sequence 107 is a unique sequence, its complement, sequence 206, is also a unique sequence. Probe 210 is a molecular beacon probe. It comprises single-stranded loop 211, stem hybrid 212, fluorophore 213, and quencher 214. Loop 211 is complementary to sequence 206. In the next amplification cycle and subsequent cycles during the exponential phase of PCR amplification, as depicted in the bottom panel of FIG. 1, amplicon strand 205 is copied by extension (215) of another copy of primer 103. It will be observed that the totality of primer 103 is perfectly complementary to strand 205; there is no unhybridized bridge sequence 105 and no bubble. Probe 210 competes with primer segment 107 for hybridizing to sequence 206. For the portion of strands 205 where probe 210 competes successfully, loop 211 hybridizes to sequence 206, and the probe becomes fluorescent. As shown in FIG. 1, even for strand 205 to which probe 210 is hybridized, anchor sequence 104, bridge sequence 105, and foot sequence 106 all hybridize to strand 205, and primer 103 acts as a very efficient conventional PCR primer. Because multiplex assays according to this invention utilize non-symmetric PCR wherein the SuperSelective primers are limiting primers and the common reverse primer is the excess primer, amplification changes from exponential to linear when a SuperSelective primer is used up. Referring again to FIG. 1, this results in production of amplicon strands 205 that have no complementary amplicon strand 202 with which to form a duplex. Molecular beacon probes 210 or other homogeneous detection probes do not have to compete with amplicon strands 202 to bind to such strands and signal.

The bubble formed by bridge sequence 105 and intervening sequence 110 may be symmetric, meaning that the lengths of the bridge sequence and the intervening sequence are the same, or the bubble may be non-symmetric, meaning that the lengths of the bridge sequence and the intervening sequence differ from one another. In either case, the bridge sequence is sufficiently long that the bridge sequence and the foot sequence together comprise an efficient PCR primer, as will be explained. Because of this, if the bubble is both quite small and non-symmetric, we often choose a bridge sequence 105 that is longer than intervening sequence 110.

Figure 2:
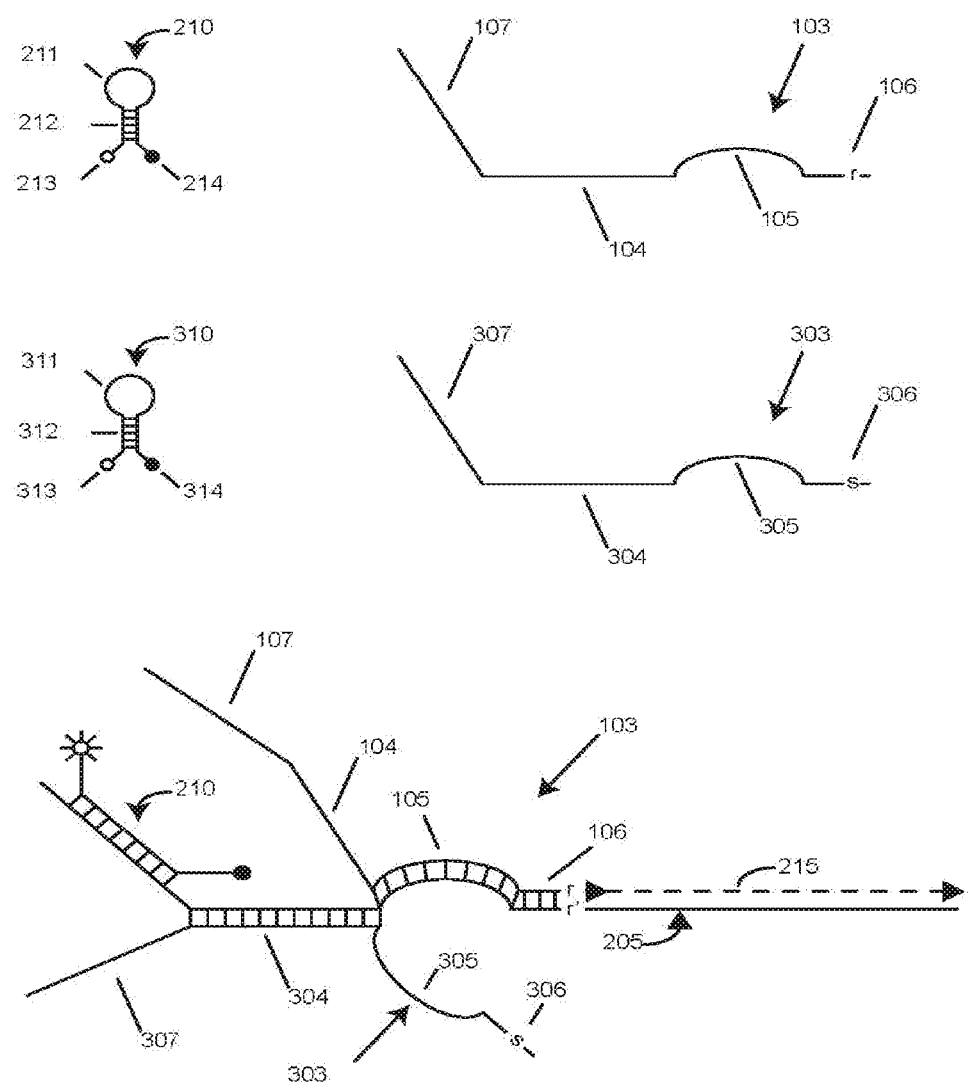
FIG. 2 is a schematic representation of two SuperSelective primers for different closely related allelic target sequences, showing why only the correct primer for a given target sequence is copied.

As explained above, each SuperSelective primer in a multiplex reaction mixture according to this invention may have a different, unique tag sequence; a different, unique bridge sequence; and a different, unique foot sequence. However, the anchor sequences of the multiple SuperSelective primers in a multiplex amplification reaction for closely related mutations may be identical or very similar This creates the possibility that during primer annealing the anchor sequence of an incorrect primer (a primer for a different closely related target sequence, mutant or wild-type) may hybridize to a product strand of the intended target sequence. In multiplex methods according to this invention that does not lead to incorrect copying, as is shown in FIG. 2. Shown at the top of FIG. 2 are primer 103 and molecular beacon probe 210 for intended target sequence 101 (FIG. 1). Shown in the middle of FIG. 2 are a SuperSelective primer 303 and molecular beacon probe 310 for a closely related target sequence (not shown). This molecular beacon probe comprises single-stranded loop 311, stem hybrid 312, fluorophore 313, and quencher 314. Primer 303 includes, in the 5' to 3' direction, tag sequence 307, anchor sequence 304, bridge sequence 305, and foot sequence 306. Primer 103's foot 106 is shown to have interrogating nucleotide "r" at the 3'-penultimate position. Primer 303's foot 306 is shown to have a different interrogating nucleotide "s" at the 3'-penultimate position. The target for loop 311 of molecular beacon probe 310 is the complement of tag sequence 307. The schematic at the bottom of FIG. 2 shows amplicon strand 205 (FIG. 1), to which primer 103 is perfectly complementary. However, anchor sequence 304 of primer 303 is the same or very similar to anchor sequence 104 of primer 103, so it can hybridize to the complement of the strand made by extension of primer 103 (strand 205 in FIG. 1). Anchor sequence 304 is shown hybridized to strand 205. However, none of its other sequences hybridize to strand 205. Tag 307, bridge 305, and foot 306 remain as single-stranded tails. This allows bridge sequence 105 and foot sequence 106 of correct primer 103 to hybridize to strand 205. In SuperSelective primers for use in methods of the invention, bridge sequence 105 and foot sequence 106 together comprise an efficient conventional PCR primer for strand 205, as shown in the bottom panel. Thus, the function of SuperSelective primer 103 to become an efficient PCR primer after the commencement of amplification is fulfilled even if the SuperSelective primers all have the same anchor sequence. The effect of the wrong primer binding through its anchor sequence is minimal, and efficient copying can still occur.

Monoplex Investigations of SuperSelective Primers

The following is an explanation of our nomenclature for SuperSelective primers. Primers that contain a 5'-tag sequence are described by the lengths (in nucleotides) of the four primer segments and the length of the intervening sequence, except that the foot is defined by the number of nucleotides 5' to the interrogating nucleotide or nucleotides, the number of interrogating nucleotides (relative, for example, to the related wild-type sequence), and the number of nucleotides 3' to the interrogating nucleotide(s). For example, 32-30-10/9-6:1:1 describes a primer having a tag 32 nucleotides long, an anchor 30 nucleotides long, a bridge 10 nucleotides long opposite an intervening sequence 9 nucleotides long, and a foot containing 6 nucleotides 5' to a single interrogating nucleotide and 1 nucleotide 3' to the interrogating nucleotide. Primers that do not contain a tag lack the first descriptor. For example, 24-14/12-5:1:1 describes a primer having an anchor 24 nucleotides long, a bridge 14 nucleotides long opposite an intervening sequence 12 nucleotides long, and a foot containing 5 nucleotides 5' to a single interrogating nucleotide and 1 nucleotide 3' to the interrogating nucleotide.

We have investigated the effect on selectivity ($\Delta C_T$) of varying several structural features of SuperSelective primers using monoplex symmetric PCR assays containing no allele-selectivity enhancing reagent, only a single SuperSelective primer, and both the intended mutant target sequence and the related wild-type sequence that differ by a single nucleotide. It is an objective to have assays with SuperSelective primers that are quantitative, wherein the PCR threshold cycle ($C_T$) reflects the starting number of an intended target sequence. An inverse linear relationship between the logarithm of the number of mutant targets originally present in a sample and the $C_T$ value observed for that sample is the hallmark of quantitative exponential amplification assays, so our investigations have included as well the effect on linearity. Experiments from this investigation are presented below in Examples 1-5. Fluorescence detection in those examples utilized SYBR® Green dye, because separate detection of different amplicons was not required.

Figure 3:
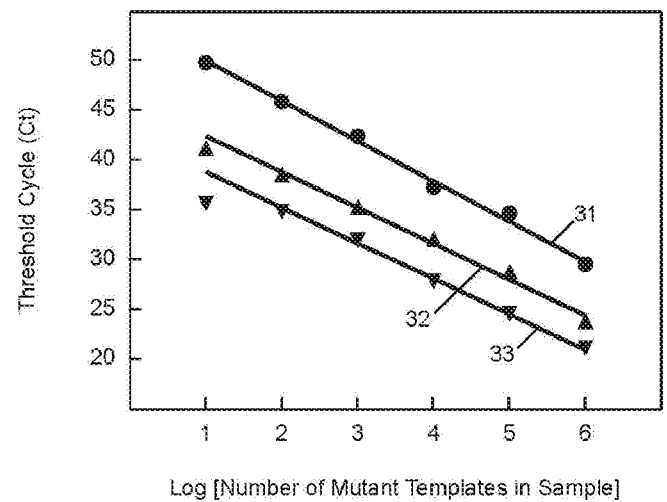
FIG. 3 is a graph of $C_T$ versus the log of the starting number of target sequences for PCR assays in Example 1 utilizing SuperSelective primers with foot sequences of different lengths.

Example 1 presents monoplex experiments using restriction enzyme-digested plasmid DNA to investigate effects resulting from changing the length of the foot sequence. We explored the effect of shortening the length of the SuperSelective primer for EGFR L858R mutant sequence's foot to overcome the probability that the foot will form a hybrid with the G-C rich sequence present in the EGFR wild-type target sequence. We carried out three sets of symmetric PCR assays, each set utilizing a SuperSelective primer whose foot sequence was 6, 7, or 8 nucleotides in length. In all other respects, the design of the primers was the same: (i) the interrogating nucleotide was located at the 3'-penultimate position of each foot; (ii) the anchor sequence was 24 nucleotides long; and (iii) the bridge sequence and the intervening sequence were both 14 nucleotides long. Each set of PCR assays was initiated with different quantities of mutant template ($10^6$, $10^5$, $10^4$, $10^3$, $10^2$, and $10^1$ copies) in the presence of $10^6$ copies of the wild-type template. In FIG. 3 the resulting threshold values are plotted as a function of the logarithm of the number of mutant templates initially present. The $C_T$ values obtained with the primer possessing the shortest foot length (six nucleotides, 4:1:1) all fall on straight line 31, demonstrating that even though the EGFR target sequence is G-C rich, as few as 10 mutant templates could be quantitated without interference from the 1,000,000 wild-type templates that were present. Primers possessing longer foot lengths (seven nucleotides, 5:1:1; or eight nucleotides, 6:1:1), however, led to a divergence from linearity when the mutant targets are most rare, due, we believe, to inadequate suppression of amplicon synthesis on the abundant wild-type templates. These results demonstrate that shorter foot lengths, though lowering the equilibrium abundance of foot hybrids, resulting in longer delays before the threshold cycle is achieved, lead to enhanced selectivity (that is, less "allele-selectivity"). From a thermodynamic standpoint, the improved selectivity at shorter foot lengths is due to the higher ratio of the equilibrium abundance of perfectly complementary mutant foot hybrids compared to the equilibrium abundance of mismatched wild-type foot hybrids.

Figure 4:
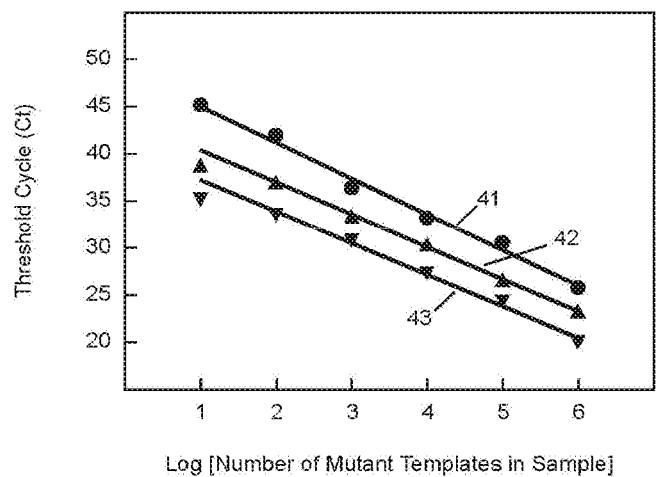
FIG. 4 is a graph of $C_T$ versus the log of starting number of target sequences for PCR assays in Example 2 utilizing SuperSelective primers that form bubbles of different circumferences.

Example 2 presents monoplex experiments using restriction enzyme-digested plasmid DNA to investigate the effects of varying the circumference of the bubble (length of the bridge sequence plus the length of the intervening sequence plus 4). The single-stranded bubble functionally separates the anchor hybrid from the foot hybrid (see FIG. 1). We carried out three sets of symmetric PCR assays that were identical to the experiment described in Example 1, except that three different SuperSelective primers were utilized, each forming a symmetrical bubble when hybridized to its template. Each of these three primers possessed the same 7-nucleotide-long foot sequence, with the interrogating nucleotide located at the 3'-penultimate position, and the length of the anchor sequence in each of the primers was maintained at 24 nucleotides. However, the bridge sequence in each primer was chosen to be 10, 14, or 18 nucleotides in length, and the identity of the anchor sequence in each primer was chosen so as to create an intervening sequence in the template that was the same length as the bridge sequence. Consequently, the circumference of the bubble formed by each of these primers when fully hybridized to a template (consisting of the bridge sequence, the intervening sequence, the two nucleotides on the end of the anchor hybrid, and the two nucleotides on the end of the foot hybrid) was 24, 32, or 40 nucleotides in length. Each set of PCR assays was initiated with different quantities of mutant template ($10^6$, $10^5$, $10^4$, $10^3$, $10^2$, and $10^1$ copies) in the presence of $10^6$ copies of wild-type template. In FIG. 4 the resulting threshold values are plotted as a function of the logarithm of the number of mutant templates initially present. The $C_T$ values obtained with the primer forming the largest bubble (40 nucleotides) all fall on straight line 41, demonstrating that even though the EGFR target sequence is G-C rich, as few as 10 mutant templates could be quantitated without interference from the 1,000,000 wild-type templates that were present. Primers possessing smaller bubbles (32 nucleotides and 24 nucleotides), however, lead to a divergence from linearity when there are only 10 mutant targets present, due, we believe, to inadequate suppression of amplicon synthesis on the abundant wild-type templates. The superior linearity of the data obtained with the primer that forms the largest bubble, although resulting in longer delays before the threshold cycle is achieved, indicates that reducing the equilibrium abundance of both the mutant hybrids and the wild-type hybrids (as a consequence of the greater entropic freedom of the foot relative to its target) enhances the selectivity of the assay.

Example 3 presents monoplex experiments using restriction enzyme-digested plasmid DNA to investigate the effects of varying the position of a single interrogating nucleotide within the foot sequence, including the primer's ability to discriminate mutant templates from wild-type templates. We carried out a series of symmetric PCR assays in which six different SuperSelective primers were utilized, each possessing an interrogating nucleotide at a different position within a 7-nucleotide-long foot sequence. The lengths of the anchor sequence, bridge sequence, and intervening sequence were maintained at 24, 14, and 14 nucleotides, respectively. The feet were 6:1:0, 5:1:1, 4:1:2, 3:1:3, 2:1:4, and 1:1:5. Two reactions were carried out with each primer, one initiated with $10^6$ copies of mutant template, and one initiated with $10^6$ copies of wild-type template. The threshold cycles that were observed are listed in Table 4 in Example 3. The results show that the window of discrimination (ΔCt) between the threshold cycle ($C_T$) for the mutant and the threshold cycle ($C_T$) for the wild type is widest when the location of the interrogating nucleotide is closest to the 3' end of the primer. Because there is only a small difference in ΔCt between the primer whose interrogating nucleotide was located at the 3' end of the foot (ΔCt=18.8), and the primer whose interrogating nucleotide was located at the penultimate position from the 3' end of the foot ($\Delta C_T$=18.2), we conclude that placement of the interrogating nucleotide at either position works well. Since the interrogating nucleotide at the penultimate position from the 3' end of the foot does not form a base pair with the corresponding nucleotide in the wild-type sequence under PCR annealing conditions, the 3'-terminal nucleotide of the foot is very unlikely to form a base pair with its corresponding nucleotide in the wild-type sequence.

Example 4 presents experiments using restriction enzyme-digested plasmid DNA to investigate the effects of varying the symmetry of the bubble. We investigated the effect of altering the symmetry of the bubble on the primer's ability to discriminate mutant templates from wild-type templates. We carried out a series of symmetric PCR assays in which one of five different SuperSelective primers was utilized. All formed bubbles that had the same circumference, but they possessed bridge sequences of different lengths. In these primers, rather than keeping all anchor sequences identical, the identity of the anchor sequence was chosen so as to create an intervening sequence in the template whose length, in combination with the length of the bridge sequence in the primer, resulted in a bubble whose circumference was 32 nucleotides. Two reactions were carried out for each primer, one initiated with $10^6$ copies of mutant template, and one initiated with $10^6$ copies of wild-type template. The threshold cycles that were observed are listed in Table 5 in Example 4. The results show that the window of discrimination (ΔCt) between the threshold cycle for the mutant target sequence and the threshold cycle for the wild-type sequence varied among the five primers, with the $\Delta C_T$ for the symmetric bubble being the highest, but there was not much difference in the $\Delta C_T$ values. We note that the circumference of the bubble (Example 2) had a somewhat greater effect on $\Delta C_T$, which reflects the equilibrium probability of a foot sequence encountering a target sequence.

Figure 5:
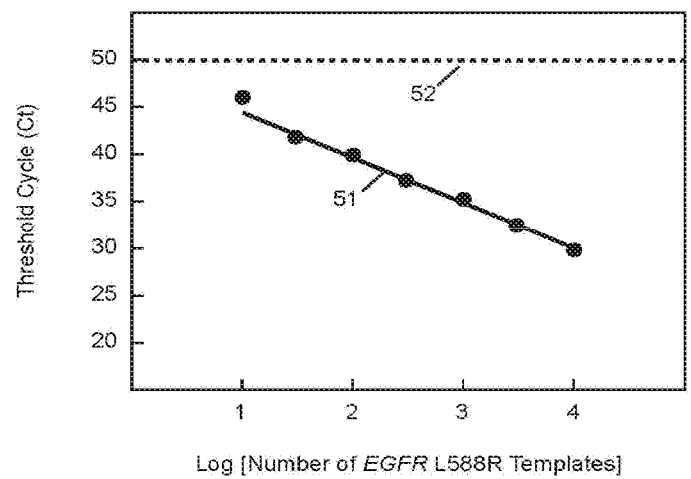
FIG. 5 is a graph of $C_T$ versus the log of starting number of target sequences for PCR assays in Example 5.

Example 5 reports experiments with restriction enzyme-digested human genomic DNA. The assays described in Examples 1-4 were carried out with DNA fragments obtained from plasmids that were digested with a restriction endonuclease in order to mimic the target sequences that occur in plasma samples. Clinical plasma samples, however, contain DNA fragments from the entire human genome. Although the number of DNA fragments in a clinical sample is highly variable from person-to-person, and from time-to-time in a given person, there are usually no more than 10,000 wild-type template fragments related to each target mutation in samples obtained from 10 mL of blood. To mimic assays initiated with DNA fragments isolated from blood plasma, we utilized the EGFR L858R 24-14/14-5:1:1 SuperSelective primer in a set of eight monoplex symmetric PCR assays that were initiated with samples that contained different quantities of restriction enzyme-digested genomic DNA isolated from human cell line H1975, which harbors the EGFR L858R mutation (DNA from 0; 10; 30; 100; 300; 1,000; 3,000; or 10,000 H1975 cells) in the presence of restriction enzyme-digested genomic DNA isolated from 10,000 human cells that contain wild-type EGFR genes. The results are shown in FIG. 5. The linearity of the plot of the $C_T$ values (line 51) as a function of the logarithm of the number of mutant fragments initially present in each reaction confirms the specificity of assays that utilize SuperSelective primers when the samples contain genomic DNA fragments. Moreover, the high $C_T$ value of the reaction initiated with only wild-type DNA (dashed line 52) confirms that the primer's selectivity is unaffected by the presence of genomic DNA fragments. The significance of this experiment is that SuperSelective primers, by virtue of their bifunctionality (both the anchor and the foot must form hybrids for amplicons to be synthesized) are so specific that they are unaffected by the presence of DNA fragments from the rest of the human genome.

We have also investigated the effects of the allele-selectivity enhancing reagent tetramethylammonium chloride (TMAC) on assay methods using SuperSelective primers, including the effect on selectivity ($\Delta C_T$) of varying several structural features of SuperSelective primers using monoplex PCR assays containing different amounts of this allele-selectivity enhancing reagent, only a single SuperSelective primer, and both the intended mutant target sequence and the related wild-type sequence that differs by a single nucleotide. Experiments from this investigation are presented below in Examples 11 to 14.

Multiplexing with SuperSelective Primers

Multiplex amplification and detection assays are assays that are capable of amplifying and detecting at least two nucleic acid sequences. Screening assays are a special case of multiplex assays that are capable of amplifying and detecting at least two nucleic acid sequences, but not more than one sequence of many possible target sequences is expected to occur. Multiplex assays and assay methods can be divided into two types. The first type is amplification and detection of unrelated mutant target sequences that are widely separated. For multiplexing of that type, a unique primer pair is used for each unrelated sequence to be amplified and detected. The second type is amplification and detection of closely related target sequences. For multiplexing of that type, a different forward primer is used for each closely related sequence, but a common reverse primer is used. In an amplification and detection assay for two closely related sequences, additional sequences to be amplified and detected may also be closely related, using a unique forward primer but the same reverse primer. Alternatively, or in addition, additional sequences to be amplified and detected may be unrelated to the at least two closely related sequences, using a unique primer pair for amplification. In the examples below, we describe duplex assays for two closely related mutations, and we describe triplex assays for two closely related mutations plus either their related wild-type sequence or an unrelated wild-type sequence.

In multiplex real-time PCR assays, where different target sequences are closely related, as occurs for the measurement of the abundance of mutations that, although they may occur in different cells, are located in the same or adjacent codons, the amplicons generated from a more abundant mutant can form heteroduplexes with complementary amplicons generated from a less abundant mutant, which results in the premature inhibition of the exponential amplification of the less abundant mutant, thereby altering the $C_T$ value of the less abundant mutant. We have discovered that the use of non-symmetric primer concentrations, in which the concentration of each SuperSelective primer is limited, preserves the independence of the $C_T$ value of each mutant target sequence and allows it to be separately determined. Apparently, the concentration of each SuperSelective primer in the initial reaction mixture is so low that even if all of the SuperSelective primers for a more abundant mutant are incorporated into (+) amplicons, there are never enough of these (+) amplicons present to significantly inhibit the exponential amplification of less abundant mutants through heteroduplex formation. Moreover, after all of the SuperSelective primers for a given mutant are incorporated into (+) amplicons, the presence of the excess common conventional reverse primers enables complementary (−) amplicons to continue to be synthesized. During this latter "linear" phase of amplification, the distinctively colored molecular beacons that bind to those (−) amplicons face virtually no competition from the less abundant complementary (+) amplicons, and the continued synthesis of those (−) amplicons provides a $C_T$ value for each mutant that is inversely linearly proportional to the abundance of that mutant in the original sample. We have also discovered that in SuperSelective primers for different mutations in the same or adjacent codons, making the sequences of the bridges different from one another creates a non-complementary region in any heteroduplex that forms between the respective amplicons, which in turn causes a SuperSelective primer to bind to and initiate synthesis on only the correct amplicon, so that the resulting Ct value is not compromised by heteroduplex formation.

Figure 6:
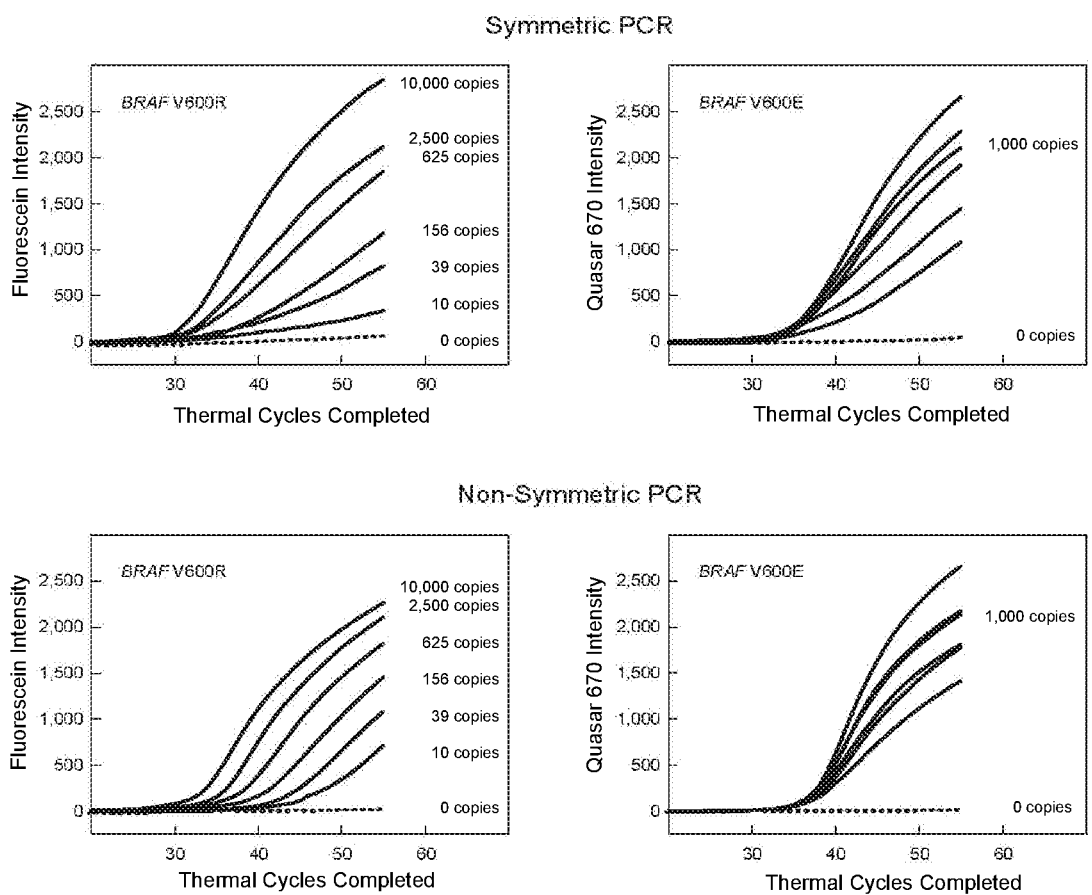
FIG. 6 shows the real-time fluorescence results (fluorescence intensity versus thermal cycle number) for the multiplex assays described in Example 6.

Example 6 and FIG. 6 illustrate the former discovery. They show the difference between symmetric PCR and non-symmetric PCR for amplifying and detecting two closely related mutant target sequences, BRAF V600R and BRAF V600E, in the presence of the related BRAF wild type. Samples contained restriction enzyme-digested plasmid DNA: a fixed amount of the wild-type target sequence (10,000 copies), a fixed amount of the BRAF V600E mutant target sequence (1,000 copies), and varying amounts of the BRAF V600R mutant target sequence (from 10,000 copies to no copies). The reactions included a SuperSelective primer for each mutant target sequence and a molecular beacon probe for the amplicons of each. Real-time fluorescence measurements (fluorescence intensity versus thermal cycle number) are presented in FIG. 6. The top left panel shows the real-time curves from the V600R probe with symmetric PCR. The bottom left panel shows the real-time curves from the V600R probe with non-symmetric PCR. When amplification was by symmetric PCR, the samples that started with differing amounts of the V600R mutant template all had similar $C_T$'s, but the slopes of the curves thereafter differed as a function of the starting quantity of the BRAF V600R mutant target sequence. When amplification was by non-symmetric PCR, on the other hand, the opposite was the case: the $C_T$ varied with the starting quantity of the BRAF V600R mutant target sequence but the slopes of the curves thereafter were parallel. The results shown in FIG. 6 demonstrate that in multiplex assays under symmetric PCR conditions, product strands (amplicons) from less abundant BRAF V600R target sequences form heteroduplexes with complementary amplicon strands from more abundant BRAF V600E target sequences, resulting in the $C_T$ values of the less abundant BRAF V600R target sequences being altered by virtue of their binding to the more abundant BRAF V600E amplicons. Alteration obscured the expected variation of $C_T$ with the starting number of templates. On the other hand, under non-symmetric PCR conditions, heteroduplexes are less abundant, thereby enabling the independent quantitation of the relative abundance of the BRAF V600R target sequences present in each sample. These results demonstrate that the $C_T$ values determined in multiplex real-time PCR assays containing non-symmetric primer concentrations provide quantitative results, despite simultaneously detecting different mutations that occur in the same codon.

Figure 7:
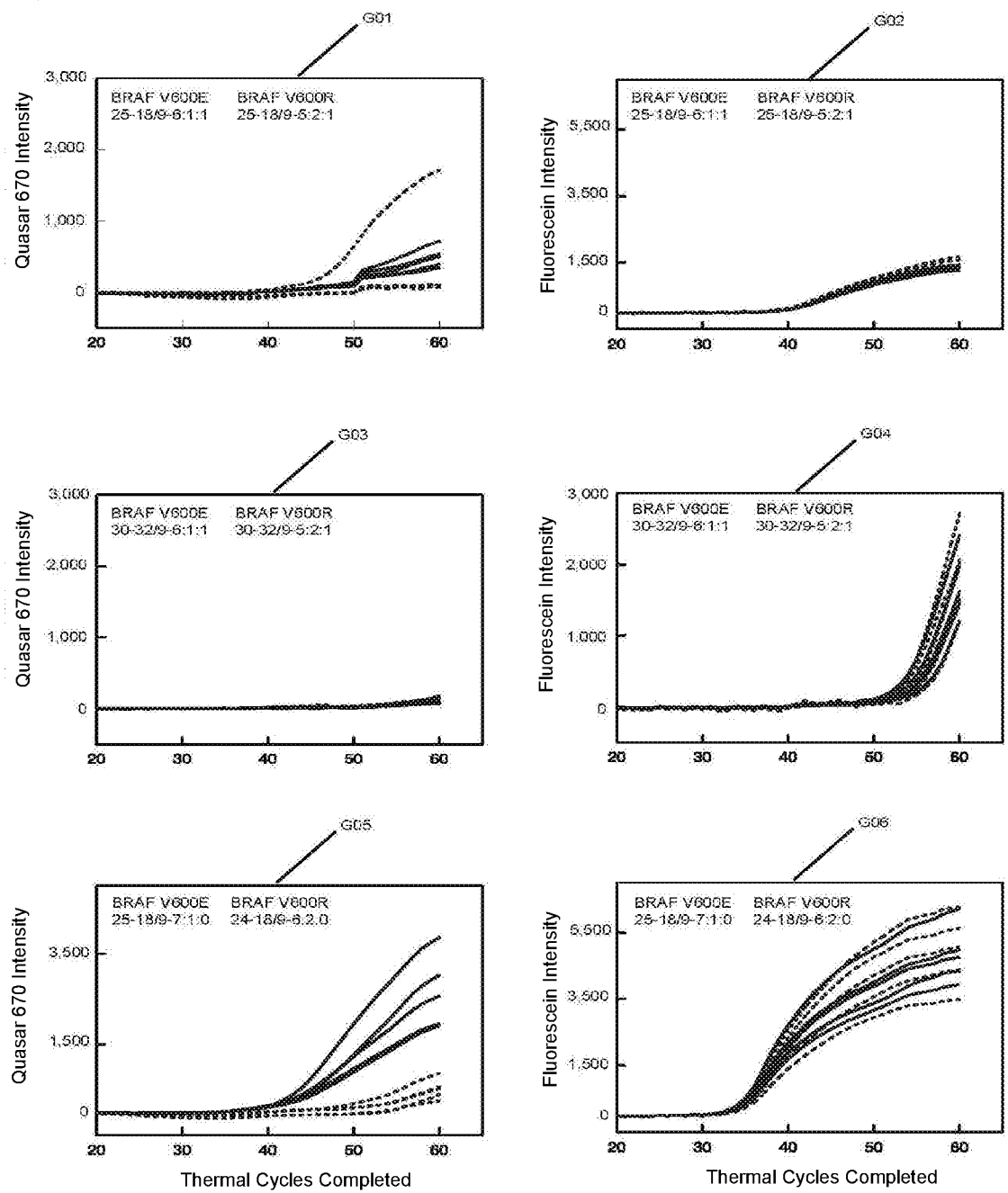
FIG. 7 shows the real-time fluorescence results for duplex PCR assays in which a molecular beacon probe targeted the complement of the bridge sequence of a SuperSelective primer as described in Example 7A.

In our copending patent application PCT/US2014/015351 (International Publication Number WO 2014/124290 A1, publication date 14 Aug. 2014) we disclosed a method of multiplexing (detecting two or more targets in the same reaction) in which the complements of long bridge sequences can be used as targets of probes, such as molecular beacons, to detect and distinguish more than one target in a single tube. Example 7 shows that while multiplex detection of more than one target is feasible with this approach, the sensitivity of detection is limited. FIG. 7, graphs G01 and G02 describe a duplex experiment in which two alternative targets (BRAF V600E and BRAF V600R) were detected using a pair of primers having 18-nucleotide long bridge sequences (BRAF V600E 25-18/9-6:1:1 and BRAF V600R 25-18/9-5:2:1 (SEQ ID No. 36 and 37)). While 1,000 molecules of a target were detectable, 5 copies did not yield detectable signals. The sensitivity of these duplex reactions was limited due to the relatively small length (18 nucleotides) of the bridge sequence. The probe-target hybrids were not stable enough to remain bound at the annealing temperatures. A solution to this problem is to increase the bridge length, as had been described. However, as also had been described, increasing the bridge length also leads to a delay in appearance of the signals. When the bridge length was increased to 32 nucleotides from 18 nucleotides (primers BRAF V600E 30-32/9-6:1:1 and BRAF V600R 30-32/9-5:2:1 (SEQ ID No. 32 and 32)), the $C_T$ values moved to the right to such a great extent that 1,000 molecules of mutant BRAF V600R could be detected in fewer than 60 cycles, but 5 molecules of mutant BRAF V600E did not produce a detectable signal within 60 cycles (FIG. 7, graphs G03 and G04).

One possible way that we devised to obtain detectable signals from the shorter 18-nucleotide long bridges is to extend the probe-binding region outwards from the bridge into the anchor and foot regions. FIG. 7, graphs G05 and G06, show results obtained from a pair of SuperSelective primers in which the probe binding regions also included a few nucleotides from the foot and the anchor regions (primers BRAF V600E 25-18/9-7:1:0 and BRAF V600R 24-18/9-6:2:0 (SEQ ID No. 34 and 35)). These primers not only yielded higher fluorescence intensities, 5 copies of BRAF V600E mutant could be detected. Although effective, this solution constrains the design of the primer sequences.

A better approach that we have discovered is the methods according to this invention, wherein a different amplifiable tag sequence is introduced at the 5' end of each primer. The complements (present in the other strand of the amplicons) then serve as the targets of the probes. The length of the probe-target hybrid can be chosen independently of the length of the bridge. As noted, these tags are copied during amplification and their complement is present in the other strand.

Figure 8:
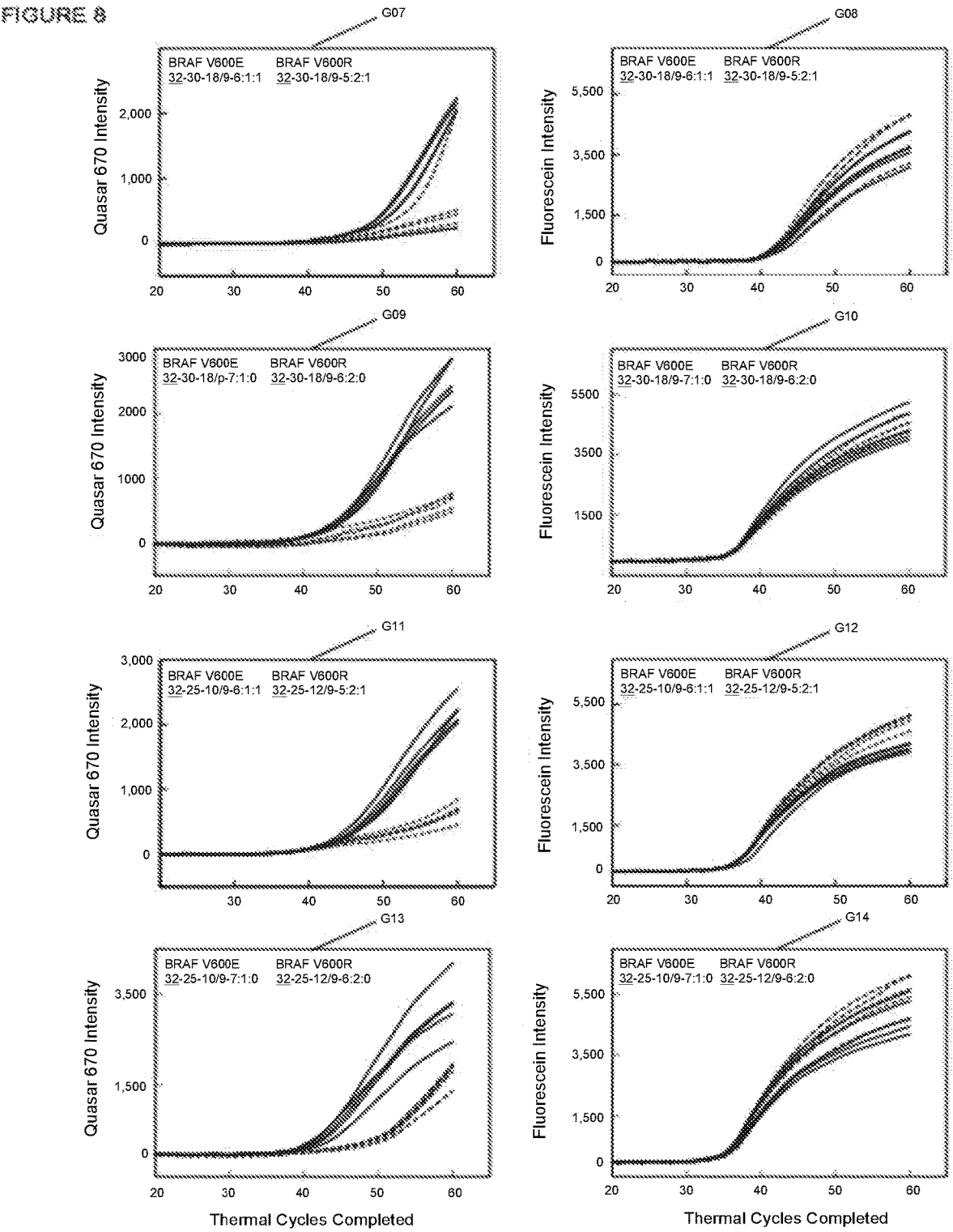
FIG. 8 shows the real-time fluorescence results for duplex PCR assays in which a molecular beacon probe targeted the complement of the 5'-tag sequence of a SuperSelective primer as described in Example 7B.

The effectiveness of such 5' tags is demonstrated in FIG. 8 (graphs G07-G14). Experiments shown in graphs G07-G08 utilized primers BRAF V600E 32-30-18/9-6:1:1 and BRAF V600R 32-30-18/9-5:2:1 (SEQ ID No. 28 and 29), which possessed a 5' tag of 32 nucleotides and a bridge of 18 nucleotides. These experiments show that most reactions initiated with 5 copies of BRAF V600E, can generally be distinguished from the reactions that had no BRAF V600E (however, one reaction with 5 copies failed to give any signal, and one negative control reaction gave rise to a detectable signal). Primers BRAF V600E 32-30-18/9-7:1:0 and BRAF V600R 32-30-18/9-6:2:0 (SEQ ID No. 30 and 31), which are similar to the previous pair except that the discriminating nucleotide lies at the 3' end rather than at the penultimate position, result in a similarly high level of discrimination (graphs G09-G10).

We have discovered that a further improvement in the sensitivity of duplex assays results when the lengths of the bridge sequences are reduced even more. This is demonstrated in graphs G11-G12 and G13-G14. When primers with shorter bridge sequences (10-12 nucleotides as opposed to 18 nucleotides) (primers BRAF V600E 32-25-10/9-6:1:1 and BRAF V600R 32-25-12/9-5:2:1 (SEQ ID No. 19 and 20)) are used, reactions initiated with five molecules of BRAF V600E target can be clearly distinguished from reactions that were initiated with no molecules of BRAF V600E target (graphs G11-G12). In addition, when another pair of primers were used, which are similar to this pair in all respects except that the discriminating nucleotide lies at the 3' end rather than at the penultimate position (primers BRAF V600E 32-25-10/9-7:1:0 and BRAF V600R 32-25-12/9-6:2:0 (SEQ ID No. 26 and 27)) similarly high levels of discrimination can be achieved (graphs G13-G14).

An important clinical goal of multiplex real-time PCR assays that utilize SuperSelective primers is to measure the abundance of different rare DNA fragments that possess mutations relevant to cancer, and to determine their abundance in relation to the amount of DNA present in the sample. However, in these multiplex assays each SuperSelective primer possesses a somewhat different foot sequence, which affects the strength of the foot hybrid (enthalpy), and each SuperSelective primer possesses a distinctly different bridge sequence, whose length and rigidity as part of the bubble affects the probability that the foot hybrid will form (entropy). Consequently, the $C_T$ value observed with a given SuperSelective primer in a multiplex PCR assay for a given number of DNA fragments containing a particular mutation can occur somewhat earlier or somewhat later than the $C_T$ values observed for the same number of DNA fragments containing a different mutation, thereby making it difficult to inter-compare the abundance of the different mutant fragments. Where this occurs, multiple graphs or charts of $C_T$ value versus the number of starting templates or $C_T$ value versus the logarithm of the number of templates initially present would be provided to a user, requiring a different graph or chart for each SuperSelective primer.

We have discovered that it is possible to make small changes in the length of a SuperSelective primer's bridge sequence in order to fine-tune the $C_T$ value that will be obtained for a given number of target sequences (without significantly affecting the selectivity of the primer). It is even possible to fine-tune the resulting $C_T$ value by making small changes in the nucleotide sequence of its bridge (without changing the number of nucleotides), thereby altering the rigidity of the bridge. In this manner, the design of each member of a set of SuperSelective primers that will be used together in a multiplex PCR assay can be adjusted (based on preliminary experimentation) so that a $C_T$ value for one target sequence represents the same number of starting templates as does that same $C_T$ value for any other target sequence. The $C_T$ values for all target sequences will then fall on the same line in a graph of $C_T$ value versus the logarithm of the starting number of templates. Consequently, a set of $C_T$ values for all of the different target sequences whose abundance is measured in the same assay will be directly inter-comparable. When a set of SuperSelective primers is fine-tuned, a user would need only a single graph or chart of $C_T$ value versus number of starting templates or $C_T$ value versus the logarithm of the number of templates initially present.

Figure 9:
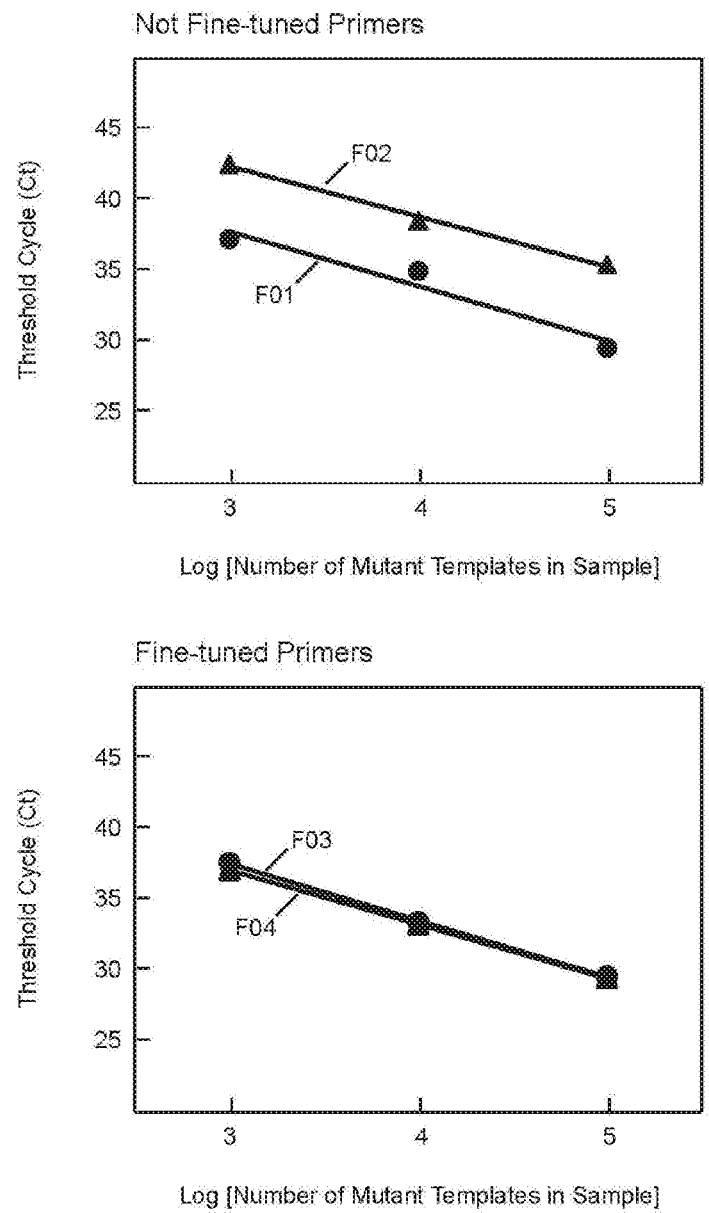
FIG. 9 presents graphs of $C_T$ versus the log of starting number of target sequences for PCR assays in Example 8 utilizing SuperSelective primers, before and after fine tuning.

Example 8 and FIG. 9 illustrate the fine-tuning of a set of two SuperSelective primers used in a duplex assay to detect two closely related mutant sequences. We started with SuperSelective primers that were not fine-tuned. Non-symmetric PCR was performed, and real-time fluorescence measurements were made. As shown in the top panel of FIG. 9, the resulting plots of $C_T$ versus the starting number of target sequences fell on different lines, not on the same line. We have found a way, which we call fine-tuning, to correct that. It will be appreciated that to fine-tune a set of primers, one or more primers can be modified. In the case of Example 8, we kept one primer the same and modified only the other primer to lower the $C_T$ values obtained with the modified primer for a given starting number of target sequences. Although some trials may be required, the effect of changing the circumference of a bubble, provided in Example 2, and the effect of changing bubble symmetry, provided in Example 4, are a guide to modifying a bridge for fine-tuning. As demonstrated in the experiment of Example 2, whose results are shown in Table 3 and FIG. 4, relatively large changes in bubble circumference produce relatively small changes in the $C_T$ values obtained with a SuperSelective primer. In the experiment reported in Example 8, what we did was to shorten the bridge sequence by five nucleotides without changing the length of the intervening sequence. As shown in the bottom panel of FIG. 9, this change in one SuperSelective primer resulted in the two SuperSelective primers being fine-tuned. The plots of $C_T$ value versus the logarithm of the number of starting templates fell on the same line. For triplex assays to amplify and detect not only two closely related mutant sequences but also a reference wild-type sequence, as reported in Examples 9 and 10, the sets of three SuperSelective primers that we used were fine tuned, as shown in FIGS. 10-13.

The unique ability to choose the length and nucleotide sequence for the bridge of each SuperSelective primer present in real-time multiplex assays enables the inclusion of a SuperSelective primer (preferably fine-tuned) for the amplification of a reference wild-type sequence, either an unrelated wild-type sequence or a related wild-type sequence. For use of an unrelated wild-type sequence, the PCR assay mixture includes a SuperSelective primer and a conventional reverse primer that are specific for the amplification of a reference wild-type sequence present in the sample. For use of a related wild-type sequence, the PCR assay mixture includes a SuperSelective primer that is specific for the reference wild-type sequence that is present in the sample, but no additional reverse primer is required. In either case, the generation of amplicons from the reference sequence (reflected by the fluorescence of a distinctively colored molecular beacon) serves as an internal control to assure that the PCR assay is functioning well. Moreover, the $C_T$ value of the wild-type amplicons reflects the amount of DNA present in the sample, and if that $C_T$ value turns out to be higher than a pre-determined value, the assay results would be ignored due to there being too little DNA in the sample for the rare target mutations, if they exist, to be present. Significantly, the use of a fine-tuned SuperSelective primer that generates a $C_T$ value that reflects the amount of DNA in the sample enables the $C_T$ values generated by the similarly fine-tuned SuperSelective primers for the mutant target sequences to be directly inter-compared. The difference between the $C_T$ value of a rare mutant and the $C_T$ value of the reference gene is a direct reflection of their relative abundance, and this comparison does not require a pre-determination of the amount of DNA in the sample.

Examples 9 and 10 demonstrate the value of including primers for a reference wild-type gene in non-symmetric multiplex assays employing fine-tuned SuperSelective primers. In Example 9, the wild-type reference is unrelated; in Example 10 it is related. Triplex real-time non-symmetric PCR assays simultaneously amplified BRAF V600E and BRAF V600R mutant sequences, and either an unrelated reference EGFR wild-type sequence (Example 9) or a related BRAF wild-type sequence (Example 10). Each reaction contained three differently colored molecular beacon probes to detect the resulting amplicons. In each example two sets of reactions were carried out. The first set contained fixed amounts of the wild-type fragments and BRAF V600E fragments (10,000 copies and 1,000 copies, respectively), and different quantities of BRAF V600R fragments (0; 10, 39; 156; 625; and 2,500 copies). The second set contained fixed amounts of the wild-type fragments and BRAF V600R fragments (10,000 copies and 1,000 copies, respectively, and different quantities of BRAF V600E fragments (0; 10, 39; 156; 625; and 2,500). Both sets in Example 9 contained 10,000 BRAF wild-type fragments to simulate actual samples, though the reactions did not include a SuperSelective primer for the exponential amplification of the BRAF wild-type sequence.

The results (shown in FIGS. 10-13) demonstrate that the $C_T$ values determined for each target sequence, when plotted against the logarithm of the number of those target sequences present in the sample, all lie on a straight line, confirming that the designs of the SuperSelective primers used in these multiplex assays were fine-tuned so that the different $C_T$ values could be directly inter-compared. Consequently, the difference ($\Delta$Ct) between the $C_T$ value obtained for each mutant target sequences in the sample and the Ct value obtained for the reference wild-type target sequence reflects the abundance of those mutant target sequences relative to the abundance of the reference wild-type target sequence, irrespective of the amount of DNA present in the sample. It is probable that the amount of DNA in a liquid biopsy sample taken from an individual will vary considerably in the course of a day. However, the abundance of each target mutation relative to the abundance of a reference gene is likely to be a reliable indicator of the underlying clinical situation. Based on comparison of the results of Examples 9 and 10, particularly the distinguishable difference in $C_T$ values between ten copies of mutant target sequence and no copies of that sequence, we prefer to use an unrelated wild-type sequence.

Multiplex Assays with Allele-Selectivity Enhancing Reagents

Certain multiplex assays, including screening assays, require an ability to detect mutations present in samples in very low copy number, for example, fewer than ten copies in DNA fragments in a liquid biopsy sample. The number of mutant DNA fragments present in a liquid biopsy sample is quite low, and is often less than ten when, for example, symptoms have not yet occurred, or when new mutations arise that are best detected early (such as when a drug-resistance mutation first appears). Detecting fewer than ten copies, even one copy, of a mutant target allelic sequence in the presence of 10,000 copies of the related wild-type sequence requires very high allele-selectivity. As has been described, two ways to increase allele-sensitivity in assay methods utilizing SuperSelective primers are to reduce the length of the foot sequence and to increase the circumference of the bubble formed by the bridge and the intervening sequence. We have found that doing so has several drawbacks. First, the $C_T$ value for fewer than ten copies of a mutant target sequence is undesirably high. Second, that $C_T$ value has substantial variability among repeat samples (for example, this variability is observed to occur when multiple samples are tested that nominally possess four target fragments). Third, because of this inherent variability, a control sample possessing only wild-type target fragments can generate a $C_T$ that is similar and difficult, if not impossible, to differentiate.

We have discovered that certain reagents, including Hofmeister salts and particularly tetramethylammonium chloride (TMAC) increase the allele-selectivity of SuperSelective primers to distinguish among closely related sequences, for example, between a mutant allele and a wild-type allele, or between different mutant alleles, or among multiple mutant alleles and their related wild-type allele. We have investigated the use of SuperSelective primers of various constructions with different concentrations of TMAC. Experiments from this investigation are presented below in Examples 11-14.

Figure 14:
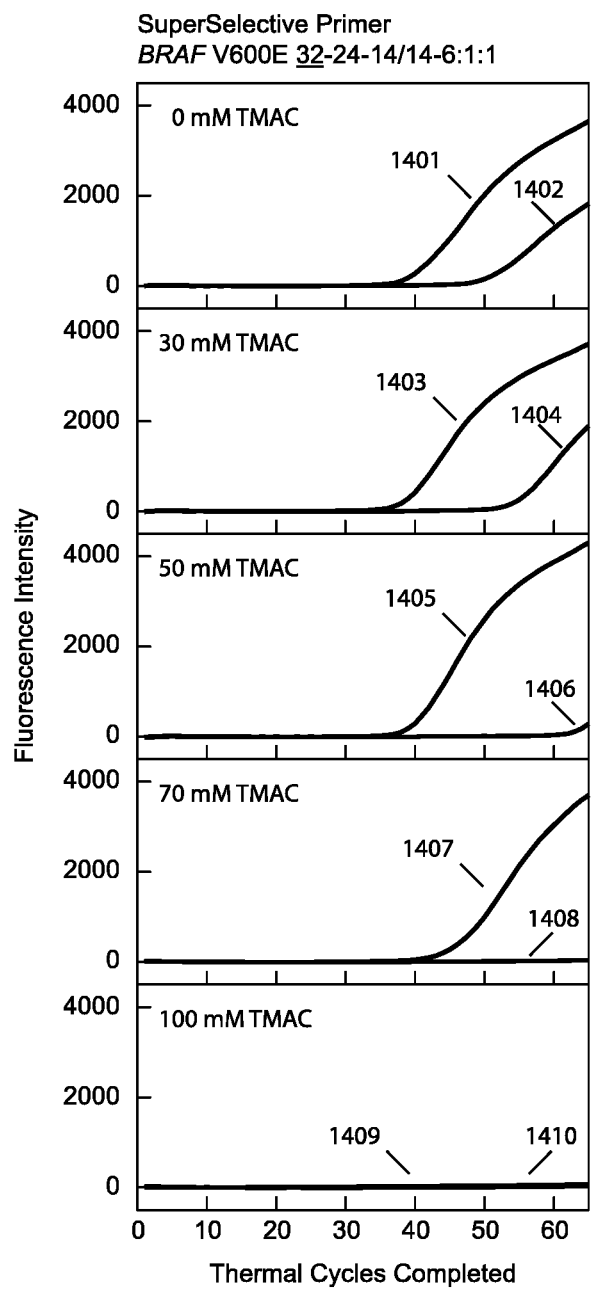
FIG. 14 shows the real-time fluorescence results of PCR assays described in Example 11A with a SuperSelective primer having a 6:1:1 foot and different concentrations of TMAC.
Figure 15:
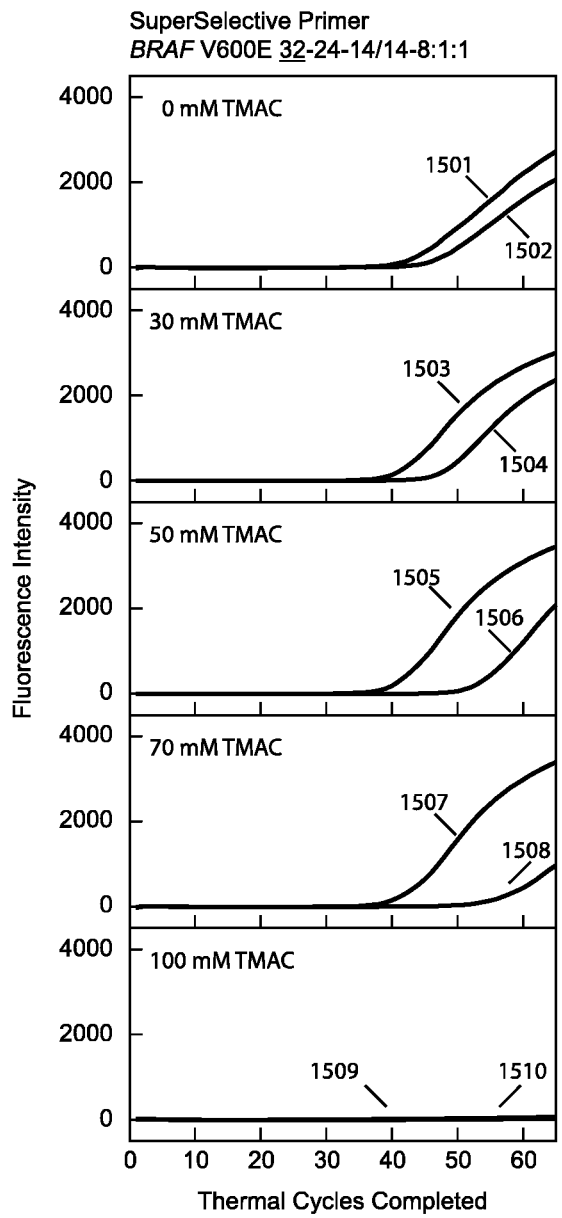
FIG. 15 shows the real-time fluorescence results of PCR assays described in Example 11B with a SuperSelective primer having an 8:1:1 foot and different concentrations of TMAC.

Example 11 shows several things:

Comparing the top panels of FIGS. 14 and 15, it can be seen that, as expected, without TMAC the assay with the shorter 6:1:1 foot gave a better $\Delta C_T$ between samples that contain mutant target sequences in the presence of a large number of related wild-type sequences and samples that only contain the large number of related wild-type sequences.

From the bottom panels of FIGS. 14 and 15, it can be seen that too high a concentration of TMAC (in these reactions, 100 mM) suppresses the amplification of the mutant sequence to the point that no $C_T$ was obtained after 60 cycles of PCR amplification.

From each of FIGS. 14 and 15 it can be seen that the $\Delta C_T$ obtained with each primer varied with the concentration of TMAC. The $\Delta C_T$ through 60 PCR cycles increased to a maximum (50 mM TMAC for the 6:1:1 foot and 70 mM TMAC for the 8:1:1 foot) and then could not be calculated, as amplification of the mutant sequence was totally suppressed.

Comparing FIGS. 14 and 15, it can be seen that with the 8:1:1 foot increasing the TMAC concentration up to 70 mM had essentially no effect on the $C_T$ of the mutant target sequence, whereas it did have a delaying effect of about 5 cycles with the shorter 6:1:1 foot.

Figure 16:
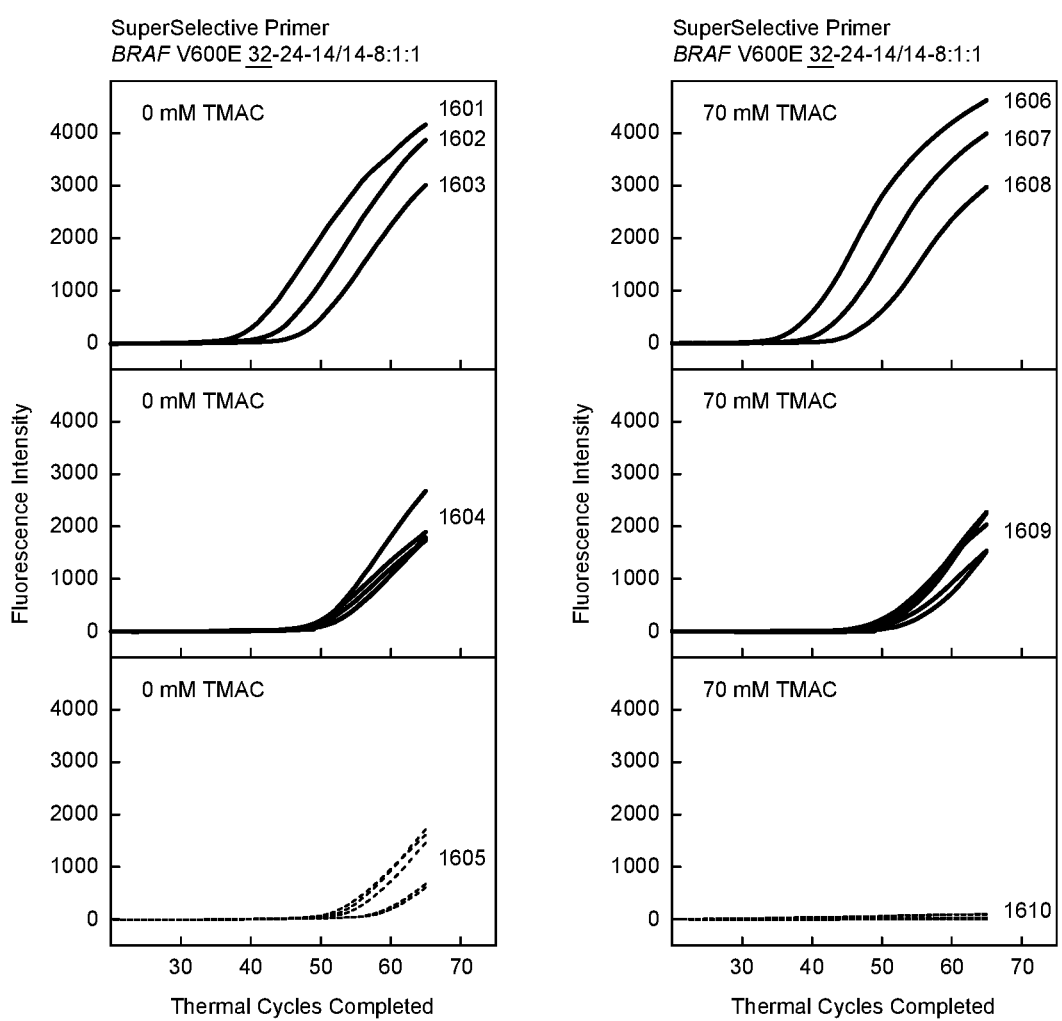
FIG. 16 shows real-time fluorescence results of PCR assays described in Example 12 with a SuperSelective primer having an 8:1:1 foot, with and without TMAC.

Example 12 demonstrates that TMAC can virtually eliminate background signals from samples containing no copies of a mutant target sequence in the presence of a large number of copies of the related wild-type sequence. Using the same 32-24/14-8:1:1 SuperSelective forward primer as used in Example 11, and 70 mM TMAC that was found to be optimal (FIG. 15, curves 1507 and 1508), we performed a series of PCR assays with 40,000 copies of wild-type sequence (an amount that might be found in a liquid biopsy sample) and either 10,000; 1,000; 100; 10; or no copies of the related mutant target sequence. For comparison, we performed a similar series with no TMAC. Five reactions with ten copies of the mutant target sequence were performed to assess variability when the number of target sequences is so low that the Poisson factor becomes significant, as has been explained above. We did the same for samples with no mutant copies. FIG. 16, like FIG. 15, shows that samples with no copies of the mutant target sequence had no $C_T$ during 65 cycles of PCR amplification. FIG. 16 also shows that all five levels of mutant target sequence concentration were distinguishable by $C_T$. In particular, despite some variability, the $C_T$ from 10 copies was distinguishable from the $C_T$ from 100 copies and from no copies, whose curve had no $C_T$. In contrast, without TMAC there was overlap in the range of $C_T$'s from 10 copies and the range from no copies.

Figure 17:
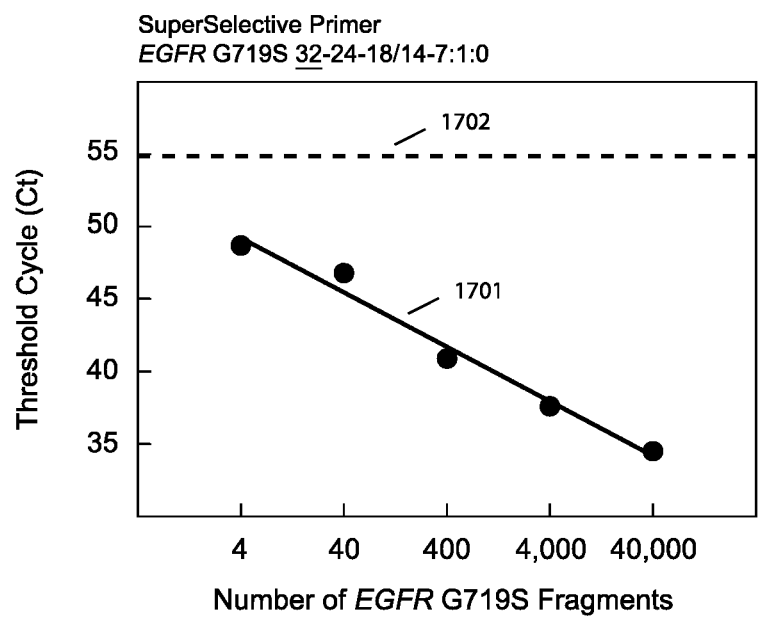
FIG. 17 is a semi-logarithmic plot of $C_T$ versus the starting number of target sequences for PCR assays described in Example 13.

Example 13 and FIG. 17 show that a plot of threshold cycle ($C_T$) versus the log of the starting number (from 4 to 40,000) of mutant target sequences in a sample such as might occur in a liquid biopsy sample (40,000 copies of the wild-type sequence) fall quite close to a straight line fit to the data (FIG. 17, line 1701); and that the $C_T$ for 4 mutant target sequences (48.7) is distinguishable from the very suppressed $C_T$ for only wild-type sequences (54.9). In this Example we used a 32-24-18/14-7:1:0 SuperSelective forward primer and 50 mM TMAC, which we believe to be more nearly optimal for a primer having a foot of 8 nucleotides.

Figure 18:
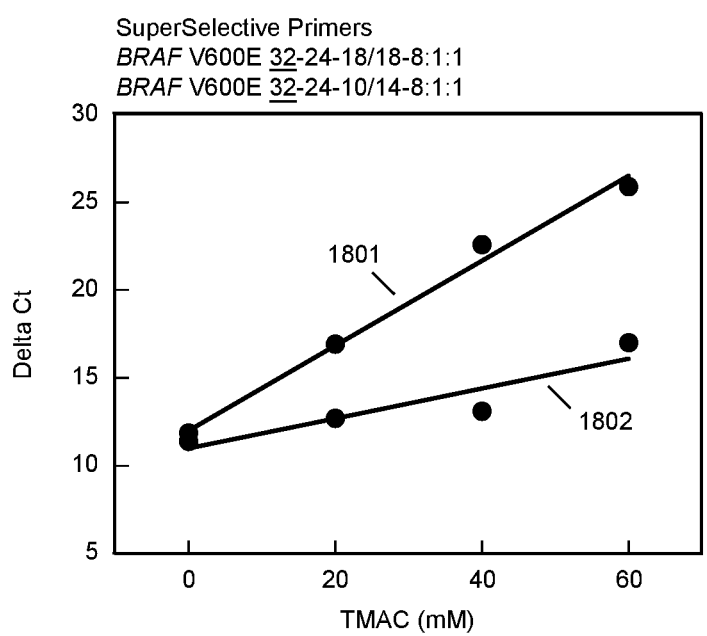
FIG. 18 is a plot of $\Delta C_T$ versus TMAC concentration for the PCR assays described in Example 14 with SuperSelective primers that create different size bubbles.

Example 14 and FIG. 18 compares the effect of different TMAC concentrations on assays that utilize SuperSelective primers having the same length foot sequence (8:1:1) but having different bridge sequences and forming different bubbles: an 18-nucleotide long bridge that forms a symmetric bubble 40 nucleotides in circumference, or a 10-nucleotide bridge that forms an asymmetric bubble 28 nucleotides in length. FIG. 18 shows that increasing the TMAC concentration had a larger effect on $\Delta C_T$ for the former (18/18 bridge) primer than on the latter (10/14 bridge) primer. Consequently, whereas somewhat above 50 mM TMAC was required to achieve a $\Delta C_T$ of about 15 using the SuperSelective primer that formed a smaller bubble (primer with the 10/14 bridge), less than 20 mM TMAC was required to achieve the same $\Delta C_T$ with the SuperSelective primer that formed a larger bubble (primer with the 18/18 bridge).

Figure 19:
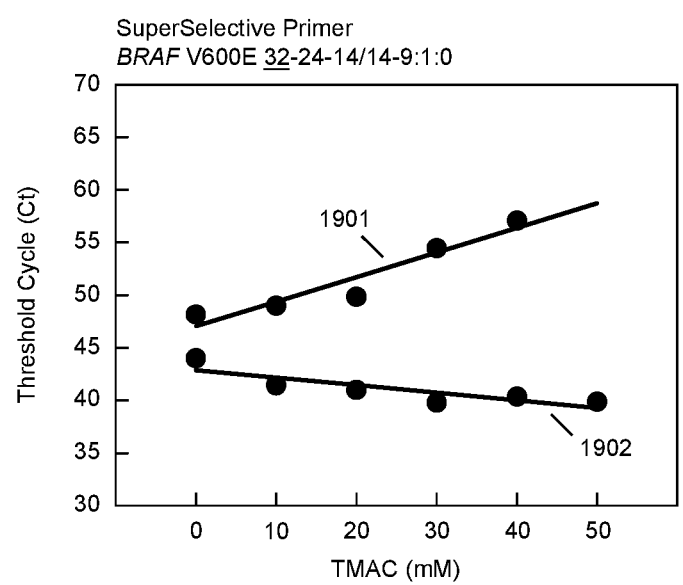
FIG. 19 is a plot of $C_T$ versus TMAC concentration for the PCR assays described in Example 15 for the SuperSelective primer having a 9:1:0 foot sequence.
Figure 20:
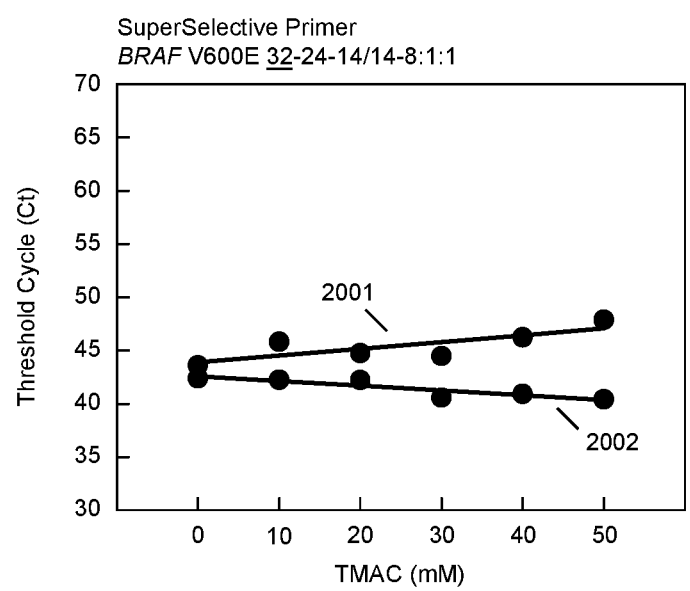
FIG. 20 is a plot of $C_T$ versus TMAC concentration for the PCR assays described in Example 15 for the SuperSelective primer having an 8:1:1 foot sequence.
Figure 21:
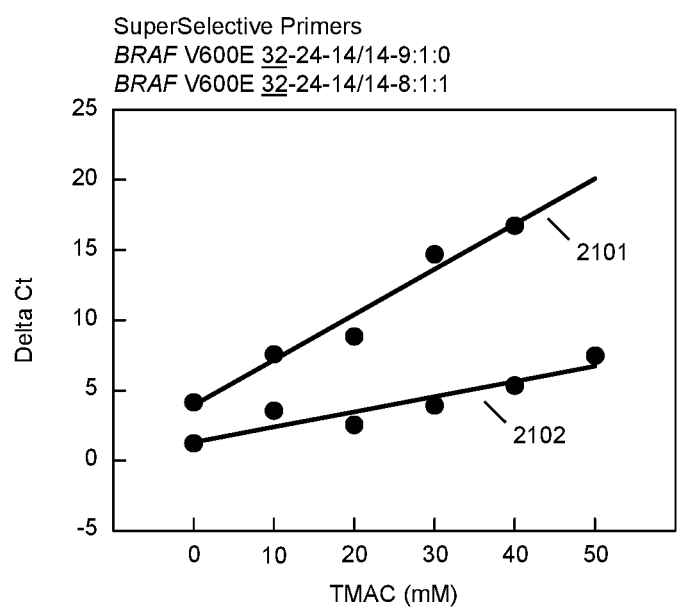
FIG. 21 is a plot of $\Delta C_T$ versus TMAC concentration for the PCR assays described in Example 15 with SuperSelective primers that have an interrogating nucleotide in different positions.

Example 15 and FIGS. 19-21 compare the effect of different TMAC concentrations (from 0 to 50 mM) in assays that utilize SuperSelective primers having the same ten-nucleotide-long foot but a different position of a single interrogating nucleotide in the foot sequence: either a 3'-terminal interrogating nucleotide (a 9:1:0 foot), or a 3'-penultimate interrogating nucleotide (an 8:1:1 foot). PCR assay mixtures contained either 0 or 4,000 copies of a mutant target sequences plus in each case 400,000 copies of the closely related wild-type sequence. Values of $C_T$ in Table 8 in Example 15 are plotted in FIGS. 19-20. Line 1902 in FIG. 19 and line 2002 in FIG. 20 show that as TMAC concentration increased, the $C_T$ of samples that included mutant target sequence decreased slightly, no matter which SuperSelective primer was used. Line 1901 in FIG. 19 and line 2001 in FIG. 20 show that as TMAC concentration increased, the $C_T$ of samples with only wild-type increased, albeit at different rates; the $C_T$ of samples with the primer having the 9:1:0 foot increased faster with TMAC concentration than did the $C_T$ of samples with the primer having the 8:1:1 foot, and the $C_T$ did not even occur in the presence of 50 mM TMAC after 65 cycles of amplification for the primer with the 9:1:0 foot. FIG. 21 shows that for both SuperSelective primers the $\Delta C_T$ ($C_T$ for the wild-type target sequence only minus $C_T$ for the mutant target sequence plus the wild-type target sequence) increased with increasing TMAC concentration, but, due to the differing effect of increasing TMAC concentration on the samples with only wild-type, the increase in $\Delta C_T$ with increasing TMAC concentration was greater for the primer having the 3'-terminal interrogating nucleotide (line 2101) than it was for the primer having the 3'-penultimate interrogating nucleotide (line 2102); that is, the slope of line 2101 is greater than the slope of line 2102.

The results of our experiments show that when we added different concentrations of TMAC (0 to 100 mM) to PCR assays containing SuperSelective primers, the effects were pronounced, dramatically increasing the $C_T$ values of samples possessing only wild-type DNA, while slightly decreasing the $C_T$ values of samples possessing both wild-type DNA fragments and mutant DNA fragments. There is a marked increase in allele-selectivity by, we conclude, a combination of thermodynamics and consequent kinetics.

FIGS. 14-16 show that as the TMAC concentration is increased, there is a maximum separation in the $C_T$ values of samples with and without mutant DNA fragments. At even higher TMAC concentrations the $C_T$ value of samples containing mutant DNA fragments increases, consequently reducing the separation in the $C_T$ values of samples with and without mutant DNA fragments. This surprising result shows that there is an optimal TMAC concentration for improving the selectivity of SuperSelective PCR assays. In our work to date, we have optimized roughly, comparing TMAC concentrations varying in 10-mM increments, but it will be appreciated that using smaller increments will permit more precise optimization, if desired.

The effect of TMAC depends on the length of the SuperSelective primer's foot. The optimal TMAC concentration for SuperSelective primers possessing relatively short feet (say 7 or 8 nucleotides in length) is lower than the optimal TMAC concentration for SuperSelective primers possessing relatively longer feet (say 9 or 10 nucleotides long).

The foregoing effects of TMAC depend on the G-C content of the foot. If the foot is high G-C, the foot should be shorter than if the foot is high A-T, and a shorter foot requires less TMAC concentration. The effect of TMAC also depends on the location of the "interrogating nucleotide" in the foot (which is the nucleotide that is complementary to the corresponding nucleotide in the mutant, but not complementary to the corresponding nucleotide in the wild-type): TMAC has a greater effect on $\Delta C_T$, if the interrogating nucleotide is the 3'-terminal nucleotide of the foot sequence.

We have drawn the following inferences from these observations:
- The mechanism by which TMAC weakens mismatched hybrids (though not known) is dependent on the number of nucleotides in the hybrid.
- TMAC has a greater weakening effect on mismatched foot hybrids having low G-C content; the relative effect of TMAC on foot hybrids depends on the length of the foot, in the sense that shorter perfectly complementary foot hybrids are already quite weak, so it takes less TMAC to significantly destabilize them, and mismatched short foot hybrids are weakest of all, and are therefore most easily affected, leading to much later $C_T$ values.
- The relative effect of TMAC on foot hybrids depends on the position of the interrogating nucleotide, with the greater effect on hybrids containing a 3'-terminal mismatch.

While not wishing to be bound by any theory, we theorize that TMAC not only weakens mismatched foot hybrids relative to corresponding perfectly complementary foot hybrids, thereby lowering their thermodynamic ratio at equilibrium, but by lowering their relative inherent stability, TMAC differentially shortens the mean persistence time of mismatched foot hybrids relative to the mean persistence time of comparable perfectly complementary hybrids, thereby enhancing the allele-selectivity of the PCR assay. Again not wishing to be bound by any theory, we currently theorize that TMAC prevents keto-enol tautomerism from occurring. The more TMAC, the less keto-enol tautomerism that occurs. Keto-enol tautomerism can result in a mismatched base pair temporarily pairing; and keto-enol tautomerism can result in complementary base pair temporarily not pairing. According to our current theory it would work as follows:

(i) For SuperSelective primers that possess a 3'-terminal interrogating nucleotide, keto-enol tautomerism enables terminal mismatched nucleotides in the foot hybrid to occasionally form a 3'-terminal base pair (consequently the polymerase does have a probability of generating an amplicon). The more TMAC, the less keto-enol tautomerism, the less likely that a 3'-terminal (mismatched) base pair will occur, the less likely that the polymerase can generate an amplicon, and the higher is the $C_T$ value.

(ii) For SuperSelective primers that possess a 3'-penultimate interrogating nucleotide, we believe that the mismatched penultimate base pair tends to prevent the 3'-terminal (matched) base pair from forming. However, due to keto-enol tautomerism, the mismatched penultimate base pair occasionally forms, leading to an occasionally fully matched foot hybrid even though there is a mismatch. The more TMAC, the less keto-enol tautomerism, the less likely that that a penultimate (mismatched) base pair will occur, the less likely that the polymerase can generate an amplicon, and the higher is the $C_T$ value.

(iii) The effect of TMAC on increasing the Ct value with a mismatched foot hybrid is greater with a SuperSelective primer possessing a 3'-terminal interrogating nucleotide than the effect of TMAC on increasing the $C_T$ value with a mismatched foot hybrid formed by a SuperSelective primer possessing a penultimate interrogating nucleotide, because it is far easier to prevent the formation of the single mismatched base pair at the 3' end of the foot hybrid than it is to both prevent the formation of the single mismatched base pair at the 3'-penultimate base pair as well as the virtually simultaneous formation of the complementary (matched) base pair at the 3' end of the foot hybrid.

(iv) As for the perfectly complementary foot hybrids formed by either SuperSelective primer, we hypothesize that the coming together of the perfectly complementary hybrid is occasionally prevented by the momentary presence of keto-enol tautomerism in one of the (nominally complementary) base pairs. However, the more TMAC that is present, the less likely is the formation of a keto-enol tautomer, and therefore the more likely is the formation of the foot hybrid, leading to an earlier $C_T$ value.

For designing a set of SuperSelective primers for use in a multiplex assay, we start by testing candidate SuperSelective primers in monoplex non-symmetric PCR assays in which each SuperSelective primer contains a 3'-terminal interrogating nucleotide and a 14/14 bridge/intervening sequence (32-nucleotide bubble). If the assay is intended to discriminate against a closely related wild-type sequence, we first check to make sure that in the primer/wild-type hybrid, if formed, the interrogating nucleotide would not form a G-T base pair—if it would, we switch to the other target strand. We test different foot lengths (for example, 7:1:0, 8:1:0 and 9:1:0) and different TMAC concentrations (20 mM to 50 mM) to ascertain the lowest concentration of TMAC that completely eliminates amplification of the wild-type sequence (no $C_T$ after 65 cycles) and the highest concentration that does not adversely affect the $C_T$ of the intended target sequence. We select a TMAC concentration to use. As all amplifications in a multiplex assay will include a single TMAC concentration, we then proceed to, as necessary, "fine tune" one or more of the SuperSelective primers by changing the lengths of the bridge and intervening sequences, and/or changing the position of the interrogating nucleotide so that the $C_T$ values obtained with any of the SuperSelective primers will reflect the number of mutant DNA fragments in the sample, irrespective of which SuperSelective primer generates the observed $C_T$ value.

By including in a PCR assay mixture an optimal concentration of TMAC, SuperSelective primers possessing longer foot sequences and smaller bubbles can be used, thereby decreasing the variability in $C_T$ values obtained when amplifying samples containing a small number of mutant DNA fragments (generally less than 10), and yet, the $C_T$ value obtained is likely to be distinguishable from the $C_T$ value obtained from a sample containing no mutant DNA fragments, as shown particularly in FIGS. 16 and 17.

Multiplex Assays with Pre-Amplification

As has been noted, potential problems arise when the number of mutant target molecules present in a sample source, for example a subject's blood, is less than ten, for example five or fewer. One problem is sample-to-sample variation. If the sample source has on average three copies of a mutant target sequence, some samples of DNA from 10,000 cells will contain precisely three copies, while others can be expected to contain fewer copies (even none) or more copies. Another problem arises from the presence of two or more different SuperSelective primers for closely related target sequences, which compete for binding to these rare targets through their identical or nearly identical anchor sequences, yet only one of these SuperSelective primers is designed to copy a particular rare target molecule, and this introduces another source of initial variability. And finally, an additional problem arises from the low probability that a SuperSelective primer will initiate copying of its intended target sequence in any given PCR thermal cycle. With very few starting templates, the thermal cycle in which exponential amplification begins may vary, and with it the threshold cycle ($C_T$). Consequently, the $C_T$ value is subject to a Poisson factor that results in the observed $C_T$ value occasionally varying from the expected $C_T$ value, and not being reliably distinguishable from the $C_T$ value of a sample that contains no mutant target fragments. Such false-negative results would diminish the utility of assays that require maximum sensitivity.

These problems are addressed by including TMAC, another effective Hofmeister salt, or another allele-selectivity enhancing reagent, as discussed above. To address these problems without such an additive, our solution is to enhance the number of target templates in a sample to which the SuperSelective primers can bind, through the use of linear pre-amplification. Before beginning exponential PCR amplification, we perform multiple cycles of linear amplification utilizing only the conventional reverse primer. The number of cycles of pre-amplification can be from three to forty, preferably from five to thirty. We describe here two methods for carrying out the linear pre-amplification.

A first method involves modifying the amplification method only, not the SuperSelective primers. In this method amplification and detection are carried out in a multi-chamber cassette. Linear pre-amplification is carried out in a first chamber in which the reaction mixture is a PCR assay mixture minus the SuperSelective primers. After pre-amplification, the resulting reaction mixture is transferred to a second chamber containing the SuperSelective primers, thereby creating the reaction mixture for exponential amplification. While the same thing could be accomplished using a reaction tube, the tube would have to be opened to add the SuperSelective primers after linear pre-amplification, a step that we recommend against.

A second method involves modifying both the amplification method and the SuperSelective primers. For this method the SuperSelective primers that are used are SuperSelective primers useful in methods of this invention that have short anchor sequences. They may be primers that have been designed for methods of this invention in which the anchor sequences are shortened to lower the Tm of the anchor sequence to 8-15° C. below the Tm of the common reverse primer. Amplification is begun with a complete PCR assay mixture that includes all primers, but cycles of pre-amplification are performed using a primer annealing temperature at least 4° C. above the Tm of the SuperSelective primers but below the Tm of the reverse primer, so that annealing of the SuperSelective primers is very unlikely but annealing of the reverse primer is very likely. Following the prescribed number of pre-amplification cycles, PCR amplification is performed according to methods of this invention using a lower primer annealing temperature at which all primers hybridize to their targets. For example, a reverse primer may be constructed to have a Tm of 70-75° C., and the SuperSelective primers can have relatively short anchor sequences that have Tm's of 60-62° C. Multiple cycles of pre-amplification with those primers can be carried out using a primer annealing temperature of 72° C., which is at least 10° C. above the Tm's of the SuperSelective primers, after which PCR amplification can be carried out using a primer annealing temperature of 60° C. Primer Tm's may be measured or calculated as is known to obtain a concentration-adjusted Tm.

Each cycle of pre-amplification creates a number of new copies of each target sequence (mutant and wild-type) equal to the starting number. For a starting number of five copies, for example, ten cycles of pre-amplification will result in 55 copies at the start of PCR amplification; 25 cycles of pre-amplification will result in 130 copies; and so on. Those numbers of copies at the start of PCR decrease variability of the cycle at which copying actually starts and are well within the detection limit of multiplex assays according to this invention. Even if the original sample contained a very small number of mutant target strands, the resulting $C_T$ value is likely to be distinguishably greater than the $C_T$ value obtained from a sample that contains no mutant target strands, and it is therefore quite unlikely that a false-negative result will occur.

EXAMPLES

Presented below in Table 1 are the sequences of primers used in monoplex PCR assays for the EGFR mutation L858R in Examples 1-5.

TABLE 1

| Primer | Sequence (5' to 3') | SEQ ID NO. |
|---|---|---|
| EGFR L858R | | |
| 24-14/14-4:1:1 | TGGTGAAAACACCGCAGCATGTCA<u>CACGAGTGAGCCCC</u>GGGCGG | 1 |
| 24-14/14-5:1:1 | CTGGTGAAAACACCGCAGCATGTC<u>GCACGAGTGAGCCC</u>TGGGCGG | 2 |

TABLE 1-continued

| Primer | Sequence (5' to 3') | SEQ ID NO. |
|---|---|---|
| 24-14/14-6:1:1 | ACTGGTGAAAACACCGCAGCATGTTGGAGCTGTGAGCCTTGGGCGG | 3 |
| 24-14/14-6:1:0 | ACTGGTGAAAACACCGCAGCATGTTGCACGAGTGAGCCTTGGGCG | 4 |
| 24-14/14-5:1:1 | CTGGTGAAAACACCGCAGCATGTCGCACGAGTGAGCCCTGGGCGG | 2 |
| 24-14/14-4:1:2 | TGGTGAAAACACCGCAGCATGTCACACGAGTGAGCCACGGGCGG | 5 |
| 24-14/14-3:1:3 | GGTGAAAACACCGCAGCATGTCAAACGAGTGAGCCACAGGCGGGC | 6 |
| 24-14/14-2:1:4 | GTGAAAACACCGCAGCATGTCAAGGAAGTGAGCCACAAGCGGGC | 7 |
| 24-14/14-1:1:5 | TGAAAACACCGCAGCATGTCAAGACAGACTGACCCAAACGGGCCA | 8 |
| 24-10/10-5:1:1 | TGAAAACACCGCAGCATGTCAAGACACTCAGCCCTGGGCGG | 9 |
| 24-14/14-5:1:1 | CTGGTGAAAACACCGCAGCATGTCGCACGAGTGAGCCCTGGGCGG | 2 |
| 24-18/18-5:1:1 | CGTACTGGTGAAAACACCGCAGCACTGACGACAAGTGAGCCCTGGGCGG | 10 |
| 24-18/10-5:1:1 | TGAAAACACCGCAGCATGTCAAGACACACGACAAGTGAGCCCTGGGCGG | 11 |
| 24-16/12-5:1:1 | GGTGAAAACACCGCAGCATGTCAATCCAACAAGTGAGCCCTGGGCGG | 12 |
| 24-14/14-5:1:1 | CTGGTGAAAACACCGCAGCATGTCGCACGAGTGAGCCCTGGGCGG | 2 |
| 24-12/16-5:1:1 | TACTGGTGAAAACACCGCAGCATGGACGACGAGCCCTGGGCGG | 13 |
| 24-10/18-5:1:1 | CGTACTGGTGAAAACACCGCAGCACTGACGGCCCTGGGCGG | 14 |
| Reverse Primer | GCATGGTATTCTTTCTCTTCCGCA | 15 |

The bridge sequence within each SuperSelective primer is underlined, and the interrogating nucleotide in its foot sequence is represented by a bold letter. The primers are arranged into groups that reflect their use in comparative experiments.

The EGFR L858R sequence that was the target for the primers in Table 1 was:

(SEQ ID No. 16)
3'-CCTTGCATGACCACTTTTGTGGCGTCGTACAGTTCTAGTGTCTAAAACCCGCCC
GGTTTGACGACCCACGCCTTCTCTTTCTTATGGTACGTCTT-5'

For purposes of illustration, the binding sites for the anchor and foot sequences of the 24-14/14-5:1:1 primer (SEQ ID No. 2) are underlined, as is the sequence of the reverse primer (SEQ ID No. 15).

Example 1. EGFR Mutation L858R and the Effect of Decreasing the SuperSelective Primer Foot Length To investigate the effect of the length of the foot sequence on selectivity and delay, the performance of three primers was compared in monoplex, symmetric PCR assays with detection using SYBR® Green dye. The primers (Table 1) were 24-14/14-4:1:1 (SEQ ID No. 1), 24-14/14-5:1:1 (SEQ ID No. 2), and 24-14/14-6:1:1 (SEQ ID No. 3). For all three primers, the anchor sequence was 24 nucleotides long, the bridge sequence was 14 nucleotides long, the bubble was 32 nucleotides in circumference and symmetric (the intervening sequence was the same length as the bridge sequence). Furthermore, in all three cases, the single interrogating nucleotide was located at the 3'-penultimate position in the foot of the primer. Using Integrated DNA Technologies' SciTools program for calculating the melting temperatures of DNA hybrids (specifying parameters: [oligo]=0.12 µM; [Na$^+$]=60 mM; [Mg$^{2+}$]=3 mM; [dNTPs]=0.25 mM each); the Tm for the binding of the 24-14/14-4:1:1 anchor sequence to a template was 68.9° C., and the Tm for the binding of the entire multi-part primer to the resulting complementary amplicon was 80.8° C.; the Tm for the binding of the 24-14/14-5:1:1 anchor sequence to a template was 67.8° C., and the Tm for the binding of the entire multi-part primer to the resulting complementary amplicon was 80.4° C.; and the Tm for the binding of the 24-14/14-6:1:1 anchor sequence to a template was 69.0° C., and the Tm for the binding of the entire multi-part primer to the resulting complementary amplicon was 79.9° C.

Primer sequences and their intended target plasmids were prepared by inserting a 115-base pair EGFR gene fragment, containing either the EGFR L858R mutation or the corresponding EGFR wild-type sequence, into a pGEM-11Zf(+) vector (Promega). Mutant and wild-type plasmid DNAs were digested with restriction endonuclease Mse I (New England Biolabs). The digestion mixture contained 10 units Mse I and 4 µg of mutant or wild-type genomic DNA in a 20-µL volume that contained 5 mM KAc, 2 mM Tris-Ac (pH 7.9), 1 mM MgAc, 1% bovine serum albumin, and 100 μM dithiothreitol. The reactions were incubated for 120 min at 37° C., followed by incubation for 20 min at 65° C. to inactivate the enzyme.

PCR amplifications were performed in 30-μL volumes containing 50 mM KCl, 10 mM Tris-HCl (pH 8.0), 3 mM $MgCl_2$, 1.5 Units AmpliTaq Gold DNA polymerase (ThermoFisher Scientific), 250 μM each of the four deoxyribonucleoside triphosphates (dNTPs), 120 nM of each primer, and 1×SYBR® Green dsDNA dye (ThermoFisher Scientific). In this series, reaction mixtures contained $10^6$ copies of the related wild-type (WT) sequence and a dilution series of the mutant (MUT) intended target sequence. Amplifications were carried out using 0.2 ml polypropylene PCR tubes (white) in a Bio-Rad IQ5 spectrofluorometric thermal cycler. The thermal-cycling profile was 10 min at 95° C., followed by 60 cycles of 95° C. for 20 sec, 60° C. for 20 sec, and 72° C. for 20 sec. SYBR® Green fluorescence intensity was measured at the end of the chain elongation step (72° C.) of each thermal cycle.

From the real-time fluorescence measurements (not shown), the assay instrument automatically calculated the threshold cycle ($C_T$) for each reaction. The $C_T$ values are listed in Table 2.

TABLE 2

| | Threshold Cycles ($C_T$) Observed for Reactions Containing Different Numbers of Intended Targets | | | | | |
|---|---|---|---|---|---|---|
| Primer | $10^6$ | $10^5$ | $10^4$ | $10^3$ | $10^2$ | $10^1$ |
| 24-14/14-4:1:1 | 29.5 | 34.7 | 37.3 | 42.4 | 45.9 | 49.8 |
| 24-14/14-5:1:1 | 23.8 | 28.8 | 32.0 | 35.3 | 38.5 | 41.2 |
| 24-14/14-6:1:1 | 20.4 | 24.8 | 28.5 | 31.9 | 34.8 | 35.7 |

FIG. 3 is a set of graphs showing the $C_T$ values observed (for each set of reactions containing the same primer) as a function of the logarithm of the number of MUT templates present in each reaction. Line 31 is a linear correlation fit to the $C_T$ values for the primer possessing a six-nucleotide-long foot sequence (4:1:1); line 32 is a linear correlation fit to the $C_T$ values for the primer possessing a seven-nucleotide-long foot sequence (5:1:1); and line 33 is a linear correlation curve fit to the $C_T$ values for the primer possessing an eight-nucleotide-long foot sequence (6:1:1).

Example 2. EGFR Mutation L858R and the Effect of Increasing the Circumference of the Bubble The experiment described in Example 1 was repeated using primers (Table 1) 24-10/10-5:1:1 (SEQ ID No. 9), 24-14/14-5:1:1 (SEQ ID No. 2), and 24-18/18-5:1:1 (SEQ ID No. 10). In all three cases, the anchor sequence was 24-nucleotides long, and the foot sequence was 5:1:1, so the single interrogating nucleotide was located at the 3'-penultimate position in the foot of each primer. The choice of the anchor sequence was such that the intervening sequence created when the primer binds to its template was the same length as the primer's bridge sequence, resulting in a symmetrical bubble. The bubble circumferences formed by this series of three multi-part primers were 24, 32, and 40 nucleotides in length, respectively.

Using Integrated DNA Technologies' SciTools program for calculating the melting temperatures of DNA hybrids (specifying parameters: [oligo]=0.12 μM; [$Na^+$]=60 mM; [$Mg^{2+}$]=3 mM; [dNTPs]=0.25 mM each); the Tm for the binding of the 24-10/10-5:1:1 anchor sequence to a template was 67.2° C., and the Tm for the binding of the entire multi-part primer to the resulting complementary amplicon was 78.5° C.; the Tm for the binding of the 24-14/14-5:1:1 anchor sequence to a template was 67.8° C., and the Tm for the binding of the entire multi-part primer to the resulting complementary amplicon was 80.4° C.; and the Tm for the binding of the 24-18/18-5:1:1 anchor sequence to a template was 68.7° C., and the Tm for the binding of the entire multi-part primer to the resulting complementary amplicon was 79.7° C.

For each of the three multi-part primer designs, a series of PCR amplification and detection assays was carried out as described in Example 1, utilizing a dilution series starting with $10^6$ copies of the WT template plus $10^6$, $10^5$, $10^4$, $10^3$, $10^2$, or $10^1$ copies of the MUT template, respectively. The assay instrument automatically calculated the threshold cycle ($C_T$) for each reaction. The $C_T$ values calculated from the real-time data for each reaction (not shown) are listed in Table 3.

TABLE 3

| | Threshold Cycles ($C_T$) Observed for Reactions Containing Different Numbers of Intended Targets | | | | | |
|---|---|---|---|---|---|---|
| Primer | $10^6$ | $10^5$ | $10^4$ | $10^3$ | $10^2$ | $10^1$ |
| 24-10/10-5:1:1 | 20.0 | 24.3 | 27.3 | 30.8 | 33.5 | 35.2 |
| 24-14/14-5:1:1 | 23.3 | 26.6 | 30.4 | 33.4 | 37.0 | 38.8 |
| 24-18/18-5:1:1 | 25.8 | 30.6 | 33.2 | 36.4 | 42.0 | 45.2 |

FIG. 4 is a set of graphs showing the $C_T$ values observed (for each set of reactions containing the same primer) as a function of the logarithm of the number of MUT templates present in each reaction. Line 43 is a linear correlation fit to $C_T$ values for the primer that formed a bubble with a circumference that was 24-nucleotides long; line 42 is a linear correlation fit to $C_T$ values for the primer that formed a bubble with a circumference that was 32-nucleotides long; and line 41 is a linear correlation fit to $C_T$ values for the primer that formed a bubble with a circumference that was 40-nucleotides long.

Example 3. EGFR Mutation L858R and the Effect of Varying the Position of a Single Interrogating Nucleotide within the Foot Sequence The experiment described in Example 2 was repeated using primers (Table 1) 24-14/14-6:1:0 (SEQ ID No. 4), 24-14/14-5:1:1 (SEQ ID No. 2), 24-14/14-4:1:2 (SEQ ID No. 5), 24-14/14-3:1:3 (SEQ ID No. 6), 24-14/14-2:1:4 (SEQ ID No. 7), and 24-14/14-1:1:5 (SEQ ID No. 8). The lengths of the anchor, bridge, intervening, and foot sequences was held constant in all the primers. The position of the single interrogating nucleotide in the foot was varied.

Using Integrated DNA Technologies' SciTools program for calculating the melting temperatures of DNA hybrids (specifying parameters: [oligo]=0.06 μM; [$Na^+$]=60 mM; [$Mg^{2+}$]=3 mM; [dNTPs]=0.25 mM each); the Tm for the binding of the 24-14/14-6:1:0 anchor sequence to a template was 69.0° C., and the Tm for the binding of the entire multi-part primer to the resulting complementary amplicon was 79.5° C.; the Tm for the binding of the 24-14/14-5:1:1 anchor sequence to a template was 67.8° C., and the Tm for the binding of the entire multi-part primer to the resulting complementary amplicon was 80.4° C.; the Tm for the binding of the 24-14/14-4:1:2 anchor sequence to a template was 67.8° C., and the Tm for the binding of the entire multi-part primer to the resulting complementary amplicon was 79.3° C.; the Tm for the binding of the 24-14/14-3:1:3 anchor sequence to a template was 66.4° C., and the Tm for the binding of the entire multi-part primer to the resulting complementary amplicon was 78.7° C.; the Tm for the binding of the 24-14/14-2:1:4 anchor sequence to a template was 65.6° C., and the Tm for the binding of the entire multi-part primer to the resulting complementary amplicon was 78.2° C.; and the Tm for the binding of the 24-14/14-1:1:5 anchor sequence to a template was 67.2° C., and the Tm for the binding of the entire multi-part primer to the resulting complementary amplicon was 78.5° C.

PCR amplifications were carried out as described in Example 1. PCR mixtures contained either $10^6$ copies of the wild-type (WT) sequence or $10^6$ copies of the related mutant target (MUT) sequence. Table 4 lists the machine-calculated $C_T$ values for both targets with each primer, and also shows the difference ($\Delta C_T$).

TABLE 4

Threshold Cycles ($C_T$) Observed for Reactions Containing Primers whose Interrogating Nucleotide is Located at Different Positions in the Foot Sequence

| Primer | $10^6$ MUT Templates | $10^6$ WT Templates | $\Delta C_T$ |
| --- | --- | --- | --- |
| 24-14/14-6:1:0 | 24.3 | 43.1 | 18.8 |
| 24-14/14-5:1:1 | 22.9 | 41.1 | 18.2 |
| 24-14/14-4:1:2 | 21.2 | 36.1 | 14.9 |
| 24-14/14-3:1:3 | 23.0 | 35.2 | 12.2 |
| 24-14/14-2:1:4 | 23.1 | 33.2 | 10.1 |
| 24-14/14-1:1:5 | 21.1 | 30.4 | 9.3 |

Example 4. EGFR Mutation L858R and the Effect of Varying the Bubble Symmetry

The experiment described in Example 3 was repeated using primers (Table 1) 24-18/10-5:1:1 (SEQ ID No. 11), 24-16/12-5:1:1 (SEQ ID No. 12), 24-14/14-5:1:1 (SEQ ID No. 2), 24-12/16-5:1:1 (SEQ ID No. 13), and 24-10/18-5:1:1 (SEQ ID No. 14). The 24-14/14-5:1:1 primer forms a "symmetrical" bubble that includes its 14-nucleotide-long bridge sequence and a 14-nucleotide-long intervening sequence from the template. The other primers form "asymmetric" bubbles wherein the bridge sequence and an intervening sequence in the template have different lengths. In this experiment, all of the multi-part primers that were compared had an anchor sequence 24-nucleotides long and a 5:1:1 foot sequence. For each multi-part primer, the identity of the anchor sequence was selected so that the sum of the length of the bridge sequence plus the length of the intervening sequence (formed by the binding of both the anchor sequence and the foot sequence to the template) equals 28. Consequently, the circumference of the bubble formed by each of these five multi-part primers was always the same.

Using Integrated DNA Technologies' SciTools program for calculating the melting temperatures of DNA hybrids (specifying parameters: [oligo]=0.12 µM; [Na$^+$]=60 mM; [Mg$^{2+}$]=3 mM; [dNTPs]=0.25 mM each); the Tm for the binding of the 24-18/10-5:1:1 anchor sequence to a template was 67.2° C., and the Tm for the binding of the entire multi-part primer to the resulting complementary amplicon was 79.6° C.; the Tm for the binding of the 24-16/12-5:1:1 anchor sequence to a template was 67.8° C., and the Tm for the binding of the entire multi-part primer to the resulting complementary amplicon was 79.0° C.; the Tm for the binding of the 24-14/14-5:1:1 anchor sequence to a template was 67.8° C., and the Tm for the binding of the entire multi-part primer to the resulting complementary amplicon was 80.4° C.; the Tm for the binding of the 24-12/16-5:1:1 anchor sequence to a template was 67.2° C., and the Tm for the binding of the entire multi-part primer to the resulting complementary amplicon was 79.9° C.; and the Tm for the binding of the 24-10/18-5:1:1 anchor sequence to a template was 68.7° C., and the Tm for the binding of the entire multi-part primer to the resulting complementary amplicon was 79.8° C.

PCR amplifications were carried out as described in Example 1. The samples with each primer contained either $10^6$ copies of the mutant (MUT) target sequence or $10^6$ copies of the related wild-type (WT) sequence. From real-time fluorescence results, that is, SYBR Green® fluorescence intensity as a function of the number of amplification cycles (not shown), the machine-calculated $C_T$ values for both targets with each primer were obtained, and the difference ($\Delta C_T$) was calculated. The results are shown in Table 5.

TABLE 5

Threshold Cycles ($C_T$) Observed for Reactions Containing Primers that Form Bubbles with Varying Symmetries

| Primer | $10^6$ MUT Templates | $10^6$ WT Templates | $\Delta C_T$ |
| --- | --- | --- | --- |
| 24-18/10-5:1:1 | 22.8 | 39.3 | 16.5 |
| 24-16/12-5:1:1 | 22.1 | 38.2 | 16.1 |
| 24-14/14-5:1:1 | 22.9 | 41.1 | 18.2 |
| 24-12/16-5:1:1 | 22.5 | 38.4 | 15.9 |
| 24-10/18-5:1:1 | 22.1 | 39.5 | 17.4 |

Example 5. Selective Amplification of the L858R Mutant Sequence in Samples Containing Human Genomic DNA To mimic assays initiated with DNA fragments isolated from blood plasma, we utilized the EGFR L858R 24-14/14-5:1:1 (SEQ ID No. 2) primer in a set of eight PCR assays that were initiated with samples that contained different quantities of restriction enzyme-digested genomic DNA isolated from human cell line H1975, which harbors the EGFR L858R mutation (DNA from 0; 10; 30; 100; 300; 1,000; 3,000; or 10,000 cells) in the presence of restriction enzyme-digested genomic DNA isolated from 10,000 human cells that contain wild-type EGFR genes.

PCR amplifications were performed in 30-µL volumes containing 50 mM KCl, 10 mM Tris-HCl (pH 8.0), 3 mM MgCl$_2$, 1.5 Unit AmpliTaq Gold DNA polymerase, 250 µM of each deoxyribonucleoside triphosphate (dNTP), 60 nM of each primer, and 1×SYBR® Green. Amplifications were carried out using 0.2 ml polypropylene PCR tubes (white) on a Bio-Rad IQ5 spectrofluorometric thermal cycler. The thermal-cycling profile was 10 min at 95° C., followed by 60 cycles of 95° C. for 20 sec, 60° C. for 15 sec, and 72° C. for 20 sec. SYBR® Green fluorescence intensity was measured at the end of each chain elongation stage (72° C.). The results are shown in FIG. 5. The threshold cycle measured for each reaction that contained mutant templates is plotted as a function of the logarithm of the number of mutant templates initially present in each reaction. Line 51 is a linear correlation fit to the data points. Dashed line 52 identifies the $C_T$ value for the amplification initiated with only wild-type templates.

In Examples 6-10 below we describe duplex assays for two closely related mutations, and we describe triplex assays for two closely related mutations plus either their corresponding wild-type sequence or an unrelated sequence that is amplified by a different primer pair. Set forth in Table 6 are the sequences of primers and probes used in these multiplex PCR assays.

TABLE 6

| Primers and Probes | Sequence (5' to 3') | SEQ ID No: |
|---|---|---|
| BRAF V600E 32-30-10/9-6:1:1 | ACCTGCCGTCAACACGTGCGCAGTAGACCATCATGAAGACCTCACAGT AAAAATAGGTGATTCAGACCCAACCTACAGAG | 17 |
| BRAF V600E 32-30-15/9-6:1:1 | ACCTGCCGTCAACACGTGCGCAGTAGACCATCATGAAGACCTCACAGT AAAAATAGGTGATTCTTAATAGACCCAACCTACAGAG | 18 |
| BRAF V600E 32-25-10/9-6:1:1 | ACCTGCCGTCAACACGTGCGCAGTAGACCATCGACCTCACAGTAAAAA TAGGTGATTCAGACCCAACCTACAGAG | 19 |
| BRAF V600R 32-30-12/9-5:2:1 | ACGTGCCCTCAATACGAGCCCCCTTCACCAACATGAAGACCTCACAGT AAAAATAGGTGATTAATGGACGGAACCTACAAGG | 20 |
| BRAF V600R 32-25-12/9-5:2:1 | ACGTGCCCTCAATACGAGCCCCCTTCACCAACGACCTCACAGTAAAAA TAGGTGATTAATGGACGGAACCTACAAGG | 21 |
| BRAF Wild Type 32-30-10/9-8:0:0 | ACGACCCGACAACCGTTGCTGCGTACTGCATCATGAAGACCTCACAGT AAAAATAGGTGATTCCACAGCACACTACAGTG | 22 |
| BRAF Reverse Primer | ATCAGTGGAAAAATAGCCTCAATTCTTACCATCC | 23 |
| EGFR Wild Type 32-25-14/9-8:0:0 | ACGACCCGACAACCGTTGCTGCGTACTGCATCGGAACGTACTGGTGAA AACACCGCAAATAGCCGCAGATCGATCACAG | 24 |
| EGFR Reverse Primer | CATGGTATTCTTTCTCTTCCGCACCCA | 25 |
| BRAF V600E 32-25-10/9-7:1:0 | ACCTGCCGTCAACACGTGCGCAGTAGACCATCAGACCTCACAGTAAAA ATAGGTGATCAGACCCAACGCTACAGA | 26 |
| BRAF V600R 32-25-12/9-6:2:0 | ACGTGCCCTCAATACGAGCCCCCTTCACCAACAGACCTCACAGTAAAA ATAGGTGATAATGGACGGAACGCTACAAG | 27 |
| BRAF V600E 32-30-18/9-6:1:1 | ACCTGCCGTCAACACGTGCGCAGTAGACCATCATGAAGACCTCACAGT AAAAATAGGTGATTCAACTTAATAGACCCAACCTACAGAG | 28 |
| BRAF V600R 32-30-18/9-5:2:1 | ACGTGCCCTCAATACGAGCCCCCTTCACCAACATGAAGACCTCACAGT AAAAATAGGTGATTACCCAATATGGACGGAACCTACAAGG | 29 |
| BRAF V600E 32-30-18/9-7:1:0 | ACCTGCCGTCAACACGTGCGCAGTAGACCATCCATGAAGACCTCACAG TAAAAATAGGTGATCAACTTAATAGACCCAACGCTACAGA | 30 |
| BRAF V600R 32-30-18/9-6:2:0 | ACGTGCCCTCAATACGAGCCCCCTTCACCAACATGAAGACCTCACAG TAAAAATAGGTGATACCCAATATGGACGGAACGCTACAAG | 31 |
| BRAF V600E 30-32/9-6:1:1 | ATGAAGACCTCACAGTAAAAATAGGTGATTACCTGCCGTCAACACG TGCGCAGTAGACCATCCTACAGAG | 32 |
| BRAF V600R 30-32/9-5:2:1 | ATGAAGACCTCACAGTAAAAATAGGTGATTACGTGCCCTCAATACG AGCCCCCTTCACCAACCTACAAGG | 33 |
| BRAF V600E 25-18/9-7:1:0 | AGACCTCACAGTAAAAATAGGTGATCACGTTATAAGAATTAACGCT ACAGA | 34 |
| BRAF V600R 24-18/9-6:2:0 | GACCTCACAGTAAAAATAGGTGATACCCAATATAGAAGGAACGCTA CAAG | 35 |
| BRAF V600E 25-18/9-6:1:1 | AGACCTCACAGTAAAAATAGGTGATCACGTTATAAGAATTAACCTA CAGAG | 36 |
| BRAF V600R 25-18/9-5:2:1 | AGACCTCACAGTAAAAATAGGTGATACCCAATATAGAAGGAACCTA CAAGG | 37 |
| Molecular Beacon V600E | Quasar 670-CGCCTGACCTGCCGTCAACACGTGCGCAGTAGACCATCCAGGCG-Black Hole Quencher 2 | 38 |
| Molecular Beacon V600R | FAM-CGCCTGACGTGCCCTCAATACGAGCCCCCTTCACCAACCAGGCG-Black Hole Quencher 1 | 39 |

TABLE 6-continued

| Primers and Probes | Sequence (5' to 3') | SEQ ID No: |
|---|---|---|
| Molecular Beacon Wild Type | CalFluor Red 610-CGCCTGA<u>CGACCCGACAACCGTTGCTGCGTACTGCATC</u>CAGGCG-Black Hole Quencher 2 | 40 |
| Molecular Beacon V600E2 | Quasar 670-CCGCTGA<u>TAGGTGATCACGTTATAAGAATTAACGC</u>CAGCGG-Black Hole Quencher 2 | 41 |
| Molecular Beacon V600R2 | FAM-CCGTGC<u>AGGTGATACCCAATATAGAAGGAACGC</u>GCACGG-Black Hole Quencher 1 | 42 |

The 5'-tag sequences (where there is a tag) and the bridge sequences within each SuperSelective primer are underlined, and the interrogating nucleotide or nucleotides in the foot sequences are represented by bold letters. The primers are arranged into groups that reflect their use in comparative experiments. For the molecular beacon probes, the single-stranded loops are underlined.

The BRAF sequences that are the targets for the BRAF primers in Table 6 are:

BRAF V600E MUT:
(SEQ ID No. 43)
3'-TAAAGAAG<u>TACTTCTGGAGTGTCATTTTTATCCACTAAAACCAGATC</u>G

<u>ATGTCTC</u>TTTAGAGCTACCTCACCCAGGGTAGTCAAACTTGTCAACAGACC

TAGGTAAAACA<u>CCTACCATTCTTAACTCCGATAAAAAGGTGACTA</u>ATTTA

A-5'.

For purposes of illustration, the binding sites for the anchor and foot sequences of the 32-30-10/9-6:1:1 primer (SEQ ID No. 17) are underlined, as is the sequence of the reverse primer (SEQ ID No. 23).

BRAF V600R MUT:
(SEQ ID No. 44)
3'-TAAAGAAG<u>TACTTCTGGAGTGTCATTTTTATCCACTAAAACCAGATC</u>

<u>GATGTTCC</u>TTTAGAGCTACCTCACCCAGGGTAGTCAAACTTGTCAACAGA

CCTAGGTAAAACA<u>CCTACCATTCTTAACTCCGATAAAAAGGTGACTA</u>ATT

TAA-5'.

For purposes of illustration, the binding sites for the anchor and foot sequences of the 32-30-12/9-5:2:1 primer (SEQ ID No. 20) are underlined, as is the sequence of the reverse primer (SEQ ID No. 23).

BRAF WT:
(SEQ ID No. 45)
3'-TAAAGAAG<u>TACTTCTGGAGTGTCATTTTTATCCACTAAAACCAGATC</u>

<u>GATGTCAC</u>TTTAGAGCTACCTCACCCAGGGTAGTCAAACTTGTCAACAGA

CCTAGGTAAAACA<u>CCTACCATTCTTAACTCCGATAAAAAGGTGACTA</u>ATT

TAA-5'.

For purposes of illustration, the binding sites for the anchor and foot sequences of the 32-30-10/9-8:0:0 primer (SEQ ID No. 22) are underlined, as is the sequence of the reverse primer (SEQ ID No. 23).

EGFR WT:
(SEQ ID No. 46)
3'-CCGTCGGT<u>CCTTGCATGACCACTTTTGTGGCGTCGTACAGTT</u>CTAGT

GTCTAAAACCCGACCGGTTTGACGA<u>CCCACGCCTTCTCTTTCTTATGGTA</u>

<u>C</u>GTCTTCCTCCGTTT-5'.

For purposes of illustration, the binding sites for the anchor and foot sequences of the 32-25-14/9-8:0:0 primer (SEQ ID No. 24) are underlined, as is the sequence of the reverse primer (SEQ ID No. 25).

Example 6. Symmetric Versus Non-Symmetric PCR Amplification

The effect of the type of PCR amplification, symmetric versus non-symmetric, was investigated by parallel sets of reactions. Each sample contained 10,000 copies of the BRAF wild-type target sequence (SEQ ID No. 34), 1,000 copies of the BRAF V600E mutant target sequence (SEQ ID No. 32), and differing amounts (10,000; 2,500; 625; 156; 39; 10; or 0 copies) of the BRAF V600R mutant target sequence (SEQ ID No. 33). Plasmids containing BRAF sequences (either the V600E mutant sequence, the V600R mutant sequence, or the wild-type sequence) were purchased from Integrated DNA Technologies, and were prepared by inserting a 200-base-pair gene fragment into pIDTSmart Amp vectors. Mutant and wild-type plasmid DNA was digested with restriction endonuclease Sca I (New England Biolabs). The digestion mixture contained 10 units Sca I and 4 µg of mutant or wild-type genomic DNA in a 20-µL volume that contained 100 mM NaCl, 10 mM $MgCl_2$, 1 mM dithiothreitol, and 50 mM Tris-HCl (pH 7.9). The reactions were incubated for 120 min at 37° C., followed by an incubation for 20 min at 80° C. to inactivate the enzyme.

PCR amplifications were performed in 30-µL volumes containing, in addition to the foregoing amounts of target sequences, 50 mM KCl, 10 mM Tris-HCl (pH 8.0), 2.5 mM $MgCl_2$, 1.5 Units Platinum Taq DNA polymerase (ThermoFisher Scientific), 250 µM each of the four deoxyribonucleoside triphosphates (dNTPs), either 500 nM (symmetric PCR) or 60 nM (non-symmetric PCR) of each of BRAF SuperSelective primer BRAF V600E 32-30-10/9-6:1:1 (SEQ ID No. 17) and BRAF V600R 32-30-12/9-5:2:1 (SEQ ID No. 20), 1,000 nM of the BRAF reverse primer (SEQ ID No. 23), 300 nM of Molecular Beacon V600E (SEQ ID No. 29), and 300 nM of Molecular Beacon V600R (SEQ ID No. 30). Amplifications were carried out using 0.2 ml polypropylene PCR tubes (white) in a Bio-Rad IQ5 spectrofluorometric thermal cycler. The thermal-cycling profile was 2 min at 95° C., followed by 60 cycles of 95° C. for 20 sec, 60° C.

for 20 sec, and 72° C. for 20 sec. Molecular beacon fluorescence intensity was measured at the end of each annealing stage (60° C.).

The results are shown in FIG. 6. The top panels are graphs of real-time fluorescence curves, fluorescence intensity versus number of thermal cycles completed, for the symmetric PCR amplifications. The graph on the left gives the intensity of fluorescence from Molecular Beacon V600R for each of the seven samples containing a different amount of the BRAF V600R mutant target sequence. The graph on the right gives the intensity of fluorescence from Molecular Beacon V600E for the same seven samples (all of which contained 1,000 copies of the BRAF V600E mutant target sequence). The bottom panels are corresponding graphs for the non-symmetric PCR amplifications.

Example 7. Duplex Assays Wherein the Complement of the Bridge Sequence or the Complement of the 5'-Tag Sequence is the Target of the Probe To compare the performance of various bridge sequences and various tag sequences, we performed a series of duplex reactions. All duplex reactions contained 10,000 molecules of BRAF wild-type target (SEQ ID No. 45), 1,000 molecules of BRAF V600R target SEQ ID No. 44), and either 5 or 0 molecules of BRAF V600E mutant target (SEQ ID No. 43). The targets of these amplification reactions were plasmids that were prepared and fragmented by a restriction enzyme as described in Example 6. Primers were designed as described in Example 1, and molecular beacons were designed as described on the molecular beacon website (molecular-beacons.org). The tag sequences were arbitrary and were designed so that they would not interact with the 3' end of any primer present in the reaction.

A. Complement of the Bridge as the Target of the Probe

We ran three experiments in which the probes targeted the complement of the bridge. In the first experiment, the non-symmetric PCR mixture contained, in addition to the target sequences, 60 nM of SuperSelective primer BRAF V600E 25-18/9-6:1:1 (SEQ ID No. 36), 60 nM of SuperSelective primer BRAF V600R 25-18/9-5:2:1 (SEQ ID No. 37), 1,000 nM of BRAF common reverse primer (SEQ ID No. 23), 300 nM of the Quasar 670-labeled molecular beacon BRAF V600E2 (SEQ ID No. 41), 300 nM of the fluorescein-labeled molecular beacon BRAF V600R2 (SEQ ID No. 42), and additional amplification reagents as described in Example 6. In the second experiment, the non-symmetric PCR mixture contained, in addition to the target sequences, 60 nM of SuperSelective primer BRAF V600E 30-32/9-6:1:1 (SEQ ID No. 32), 60 nM of SuperSelective primer BRAF V600R 30-32/9-5:2:1 (SEQ ID No. 33), 1,000 nM of BRAF common reverse primer (SEQ ID No. 23), 300 nM of the Quasar 670-labeled molecular beacon BRAF V600E (SEQ ID No. 38), 300 nM of the fluorescein-labeled molecular beacon BRAF V600R (SEQ ID No. 39), and additional amplification reagents as described in Example 6. In the third experiment, the non-symmetric PCR mixture contained, in addition to the target sequences, 60 nM of SuperSelective primer BRAF V600E 25-18/9-7:1:0 (SEQ ID No. 34), 60 nM of SuperSelective primer BRAF V600R 24-18/9-6:2:0 (SEQ ID No. 35), 1,000 nM of BRAF common reverse primer (SEQ ID No. 23), 300 nM of the Quasar 670-labeled molecular beacon BRAF V600E2 (SEQ ID No. 41), 300 nM of the fluorescein-labeled molecular beacon BRAF V600R2 (SEQ ID No. 42), and additional amplification reagents as described in Example 6.

Amplification and real-time detection were performed as described in Example 6. Each experiment was repeated five times. The results are shown in FIG. 7, which includes three pairs of graphs of fluorescence intensity versus the number of thermal cycles completed. In each pair of panels, the left graph is for Quasar 670 (V600E molecular beacon) and the right graph is for fluorescein (V600R molecular beacon). Replicate reactions that were initiated with 5 copies of BRAF V600E mutant target sequence are presented by continuous lines and the fluorescence changes in the reactions initiated with 0 copies of BRAF V600E mutant target sequence are presented by broken lines. The top pair of graphs, G01 and G02, shows the results of the first experiment, in which the bridge length was 18 nucleotides and the bubble circumference was 31 nucleotides. The middle pair of graphs, G03 and G04, shows the results of the second experiment, in which the bridge length was 32 nucleotides and the bubble circumference was 45 nucleotides. The bottom pair of graphs, G05 and G06, shows the results of the third experiment, in which the bridge length and bubble circumference were as in the first experiment but the feet of the SuperSelective primers were different.

B. Complement of the Tag as the Target of the Probe

We ran four experiments in which the probes targeted the complement of the 5' tag. In the first experiment, the non-symmetric PCR mixture contained, in addition to the target sequences, 60 nM of SuperSelective primer BRAF V600E 32-30-18/9-6:1:1 (SEQ ID No. 28), 60 nM of SuperSelective primer BRAF V600R 32-30-18/9-5:2:1 (SEQ ID No. 29), 1,000 nM of BRAF common reverse primer (SEQ ID No. 23), 300 nM of the Quasar 670-labeled molecular beacon BRAF V600E (SEQ ID No. 38), 300 nM of the fluorescein-labeled molecular beacon BRAF V600R (SEQ ID No. 39), and additional amplification reagents as described in Example 6. In the second experiment, the non-symmetric PCR mixture contained, in addition to the target sequences, 60 nM of SuperSelective primer BRAF V600E 32-30-18/9-7:1:0 (SEQ ID No. 30), 60 nM of SuperSelective primer BRAF V600R 32-30-18/9-6:2:0 (SEQ ID No. 31), 1,000 nM of BRAF common reverse primer (SEQ ID No. 23), 300 nM of the Quasar 670-labeled molecular beacon BRAF V600E (SEQ ID No. 38), 300 nM of the fluorescein-labeled molecular beacon BRAF V600R (SEQ ID No. 39), and additional amplification reagents as described in Example 6. In the third experiment, the non-symmetric PCR mixture contained, in addition to the target sequences, 60 nM of SuperSelective primer BRAF V600E 32-25-10/9-6:1:1 (SEQ ID No. 19), 60 nM of SuperSelective primer BRAF V600R 32-25-12/9-5:2:1 (SEQ ID No. 20), 1,000 nM of BRAF common reverse primer (SEQ ID No. 23), 300 nM of the Quasar 670-labeled molecular beacon BRAF V600E (SEQ ID No. 38), 300 nM of the fluorescein-labeled molecular beacon BRAF V600R (SEQ ID No. 39), and additional amplification reagents as described in Example 6. In the fourth experiment, the non-symmetric PCR mixture contained, in addition to the target sequences, 60 nM of SuperSelective primer BRAF V600E 32-25-10/9-7:1:0 (SEQ ID No. 26), 60 nM of SuperSelective primer BRAF V600R 32-25-12/9-6:2:0 (SEQ ID No. 27), 1,000 nM of BRAF common reverse primer (SEQ ID No. 23), 300 nM of the Quasar 670-labeled molecular beacon BRAF V600E (SEQ ID No. 38), 300 nM of the fluorescein-labeled molecular beacon BRAF V600R (SEQ ID No. 39), and additional amplification reagents as described in Example 6.

Amplification and real-time detection were performed as described in Example 6. Each experiment was repeated five times. The results are reported in FIG. 8, which includes four pairs of graphs of fluorescence intensity versus the number of thermal cycles completed. In each pair of panels, the left graph is for Quasar 670 (V600E molecular beacon) and the right graph is for fluorescein (V600R molecular beacon). Replicate reactions that were initiated with 5 copies of BRAF V600E mutant target sequence are presented by continuous lines and the fluorescence changes in the reactions initiated with 0 copies of BRAF V600E mutant target sequence are presented by broken lines. The top pair of graphs, G07 and G08, is from the first experiment, in which the bridge length was 18 nucleotides and the bubble circumference was 31 nucleotides. The second pair of graphs, G09 and G10, is from the second experiment, in which the bridge length and the bubble circumference were unchanged, but the interrogating nucleotide in the foot of the V600E SuperSelective primer was changed from the 3'-penultimate nucleotide to the 3'-terminal nucleotide. The third pair of graphs, G11 and G12, is from the third experiment, in which the bridge lengths and bubble circumferences were short. The fourth (bottom) set of graphs, G13 and G14, is from the fourth experiment, in which the bridge lengths were again short, but the interrogating nucleotide of the V600E SuperSelective primer was changed from the 3'-penultimate nucleotide to the 3' terminal nucleotide.

Example 8. Fine-Tuning SuperSelective Primers for Multiplex Assays

If the plots of $C_T$ values as a function of the logarithm of the number of templates present in a reaction for a set of different SuperSelective primers in a multiplex reaction fall on different lines, we describe that set of SuperSelective primers as being not fine-tuned. On the other hand, if those plots fall on the same line, we describe that set of SuperSelective primers as being fine-tuned. In designing SuperSelective primers for a multiplex assay, an initial design almost always yields primers that are not fine-tuned. By adjusting the lengths and identities (nucleotide sequences) of the bridges, we can fine-tune the primers. In this example we describe first a multiplex assay in which the SuperSelective primers turned out not to be fine-tuned; and we then describe the same multiplex assay after we fine-tuned the set of SuperSelective primers. Mutant BRAF V600E, Mutant BRAF V600R, and wild-type BRAF plasmid DNAs were prepared as described in Example 6.

A. Primers Before Fine-tuning

Two series of reactions were prepared. For the first series of reactions, each sample contained 100,000 copies of the BRAF wild-type target sequence (SEQ ID No. 45), 10,000 copies of the BRAF V600E mutant target sequence (SEQ ID No. 43), and differing amounts (100,000; 10,000; or 1,000 copies) of the BRAF V600R mutant target sequence (SEQ ID No. 44). For the second series of reactions, each sample contained 100,000 copies of the BRAF wild-type target sequence (SEQ ID No. 45), 10,000 copies of the BRAF V600R mutant target sequence (SEQ ID No. 44), and differing amounts (100,000; 10,000; or 1,000 copies) of the BRAF V600E mutant target sequence (SEQ ID No. 43).

PCR amplifications were performed as described in Example 6 with the following modifications for the primers and the molecular beacon probes that were used. The reactions contained 60 nM of each of the BRAF SuperSelective primers BRAF V600E 32-30-15/9-6:1:1 (SEQ ID No. 18) and BRAF V600R 32-30-12/9-5:2:1 (SEQ ID No. 20), 1,000 nM of the BRAF reverse primer (SEQ ID No. 23), 300 nM of Molecular Beacon V600E (SEQ ID No. 38) and 300 nM of Molecular Beacon V600R (SEQ ID No. 39). The results are shown in the top panel of FIG. 9, which is a graph of the $C_T$ values observed as a function of the logarithm of the number of variable templates present in each reaction. The solid circles represent the reactions with differing amounts of BRAF V600R and the solid triangles represent the reactions with differing amounts of BRAF V600E. Line F01 is a linear correlation fit to the BRAF V600R data and line F02 is a linear correlation fit to the BRAF V600E data.

B. Primers after Fine-Tuning

For the assay with fine-tuned primers, the reactions were as described in part A except that the SuperSelective primers were BRAF V600E 32-30-10/9-6:1:1 (SEQ ID No. 17) and BRAF V600R 32-30-12/9-5:2:1 (SEQ ID No. 20). The results are shown in the bottom panel of FIG. 9, which is a graph of the $C_T$ values observed as a function of the logarithm of the number of variable templates present in each reaction. The solid circles represent the reactions with differing amounts of BRAF V600R and the solid triangles represent the reactions with differing amounts of BRAF V600E. Line F03 is a linear correlation fit to the BRAF V600R data and line F04 is a linear correlation fit to the BRAF V600E data.

As indicated, in fine-tuning the primers we kept the BRAF V600R primer (SEQ ID No. 20) the same and modified only the BRAF V600E primer so that line F04 fell atop line F03. Comparing the untuned primer (SEQ ID No. 18) to the tuned primer (SEQ ID No. 17), whose sequences are given in Table 6, it can be seen that in this instance we kept the 5'-terminal nucleotide of the bridge sequence but removed the next five nucleotides (TTATT) from the bridge sequence of the BRAF V600E primer, which achieved our objective of fine-tuning.

Example 9. Multiplex PCR Assays that Amplify and Detect an Unrelated Reference Wild-Type Sequence Triplex assays were performed to amplify and detect two closely related mutant target sequences (BRAF V600R and BRAF V600E) and also an unrelated wild-type sequence (EGFR). In a first series, the starting amount of the BRAF V600R mutant target sequence was varied. In a second series, the starting amount of the BRAF V600E mutant target sequence was varied.

Mutant BRAF V600E and BRAF V600R plasmid DNA were prepared as described in Example 6, and wild-type EGFR plasmid DNA was prepared as described in Example 1.

A. Varying BRAF V600R

Each of six samples contained 10,000 copies of the EGFR wild-type target sequence (SEQ ID No. 46), 10,000 copies of the BRAF wild-type sequence (SEQ ID No. 45), 1,000 copies of the BRAF V600E mutant target sequence (SEQ ID No. 43), and differing amounts (2,500; 625; 156; 39; 10; or 0 copies) of the BRAF V600R mutant target sequence (SEQ ID No. 44).

PCR amplifications were performed in 30-μL volumes containing, in addition to the foregoing amounts of target sequences, 50 mM KCl, 10 mM Tris-HCl (pH 8.0), 2.5 mM $MgCl_2$, 1.5 Units Platinum Taq DNA polymerase (ThermoFisher Scientific), 250 μM each of the four deoxyribonucleoside triphosphates (dNTPs), 60 nM of primer BRAF V600E 32-30-10/9-6:1:1 (SEQ ID No. 17), 60 nM of primer BRAF V600R 32-30-12/9-5:2:1 (SEQ ID No. 20), 60 nM of primer EGFR wild type 32-25-14/9-8:0:0 (SEQ ID No. 24), 1,000 nM of the BRAF reverse primer (SEQ ID No. 23), 500 nM of the EGFR reverse primer (SEQ ID No. 25), 300 nM of Molecular Beacon V600E (SEQ ID No. 38), 300 nM of Molecular Beacon V600R (SEQ ID No. 39), and 300 nM of Molecular Beacon Wild Type (SEQ ID No. 40). Amplifications were carried out using 0.2 ml polypropylene tubes (white) in a Bio-Rad IQ5 spectrofluorometric thermal cycler. The thermal-cycling profile was 2 min at 95° C., followed by 55 cycles of 95° C. for 20 sec, 60° C. for 20 sec, and 72° C. for 20 sec. Molecular beacon fluorescence intensity was measured at the end of each annealing stage (60° C.).

Figure 10:
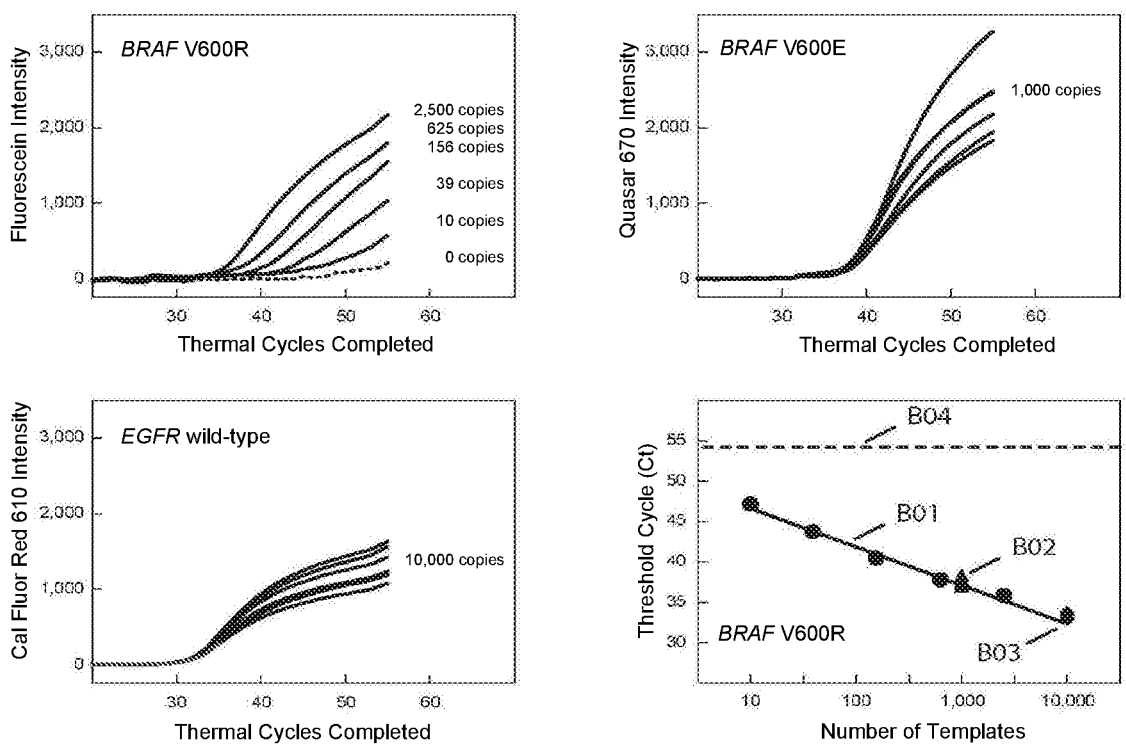
FIG. 10 shows the real-time fluorescence results for multiplex PCR assays described in Example 9A in which an unrelated wild-type sequence was also amplified and detected.

The results are shown in FIG. 10. Three of the panels are graphs of real-time fluorescence curves, fluorescence intensity versus the number of thermal cycle completed. The top left graph shows the curves of fluorescence from Molecular Beacon V600R for the six samples that contained different amounts of the BRAF V600R mutant target sequence. The top right graph shows the curves of fluorescence from Molecular Beacon V600E for the 1,000 copies of the BRAF V600E target sequence contained in each of those six samples. The lower left graph shows the curves of fluorescence from Molecular Beacon Wild Type for the 10,000 copies of the EGFR wild-type sequence contained in each of those six samples. The lower right panel is a graph of the $C_T$ values obtained from the real-time curves as a function of the logarithm of the number of templates present in each reaction. The solid circles are the $C_T$ values for BRAF V600R; solid triangles, B02, are the $C_T$ values for BRAF V600E; and solid diamonds, B03, are the $C_T$ values for the EGFR wild type. Line B01 is a linear correlation fit to the BRAF V600R data. Dashed line B04 identifies the $C_T$ value for the amplification initiated with 10,000 EGFR wild-type templates, 10,000 BRAF wild-type templates, 1,000 BRAF V600E templates, and no BRAF V600R templates.

B. Varying BRAF V600E

Each of six samples contained 10,000 copies of the EGFR wild-type target sequence (SEQ ID No. 46), 10,000 copies of the BRAF wild-type sequence (SEQ ID No. 45), 1,000 copies of the BRAF V600R mutant target sequence (SEQ ID No. 44), and differing amounts (2,500; 625; 156; 39; 10; or 0 copies) of the BRAF V600E mutant target sequence (SEQ ID No. 43). Amplification reaction mixtures and PCR amplifications were as reported in part A above.

Figure 11:
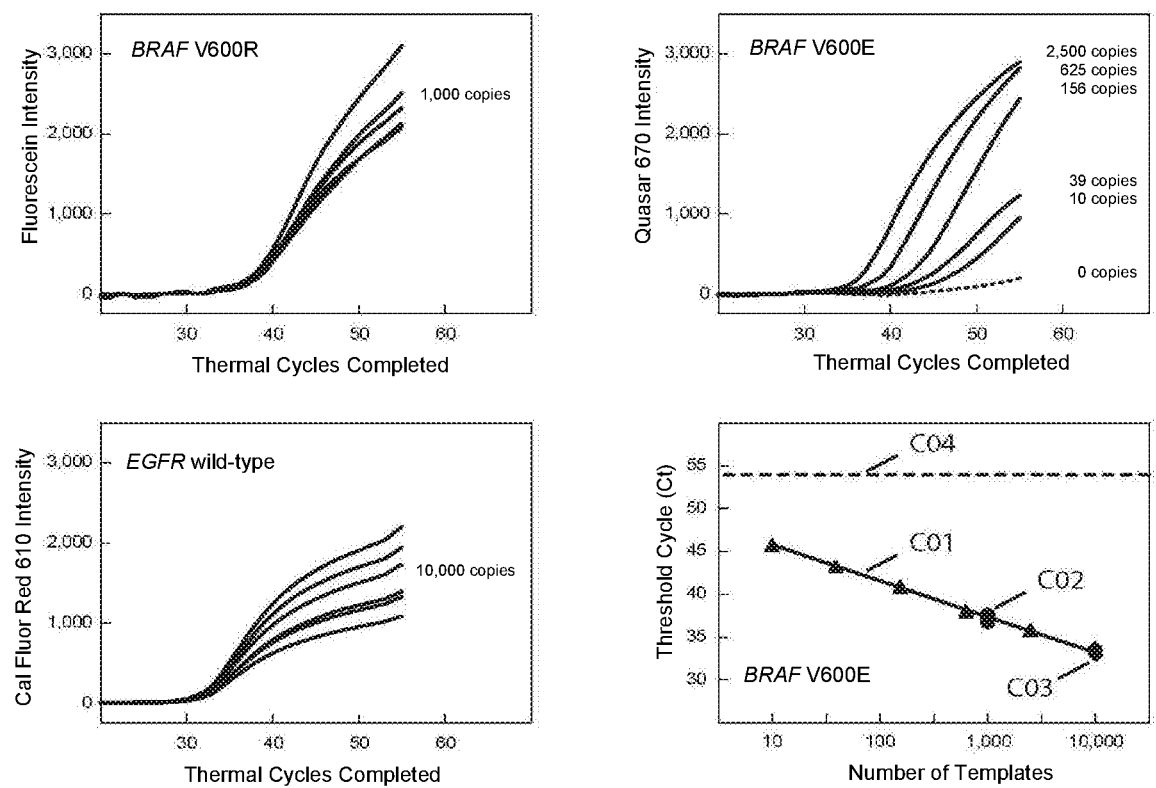
FIG. 11 shows the real-time fluorescence results for multiplex PCR assays described in Example 9B in which an unrelated wild-type sequence was also amplified and detected.

The results are shown in FIG. 11. Three of the panels are graphs of real-time fluorescence curves, fluorescence intensity versus the number of thermal cycles completed. The top right graph shows the curves of fluorescence from Molecular Beacon V600E for the six samples that contained different amounts of the BRAF V600E mutant target sequence. The top left graph shows the curves of fluorescence from Molecular Beacon V600R for the 1,000 copies of the BRAF V600R target sequence contained in each of those six samples. The lower left graph shows the curves of fluorescence from Molecular Beacon Wild Type for the 10,000 copies of the EGFR wild-type sequence contained in each of those six samples. The lower right panel is a graph of the $C_T$ values obtained from the real-time curves as a function of the logarithm of the number of templates present in each reaction. The solid triangles are the $C_T$ values for BRAF V600E; solid circles, C02, are the $C_T$ values for BRAF V600R; and solid diamonds, C03, are the $C_T$ values for the EGFR wild type. Line C01 is a linear correlation fit to the BRAF V600E data. Dashed line C04 identifies the $C_T$ value for the amplification initiated with 10,000 EGFR wild-type templates, 10,000 BRAF wild-type templates, 1,000 BRAF V600R templates, and no BRAF V600E templates.

Example 10. Multiplex PCR Assays that Amplify and Detect a Related Reference Wild-Type Sequence Triplex assays were performed to amplify and detect two closely related mutant target sequences (BRAF V600R and BRAF V600E) and also their related wild-type sequence (BRAF Wild Type). In a first series, the starting amount of the BRAF V600R mutant target sequence was varied. In a second series, the starting amount of the BRAF V600E mutant target sequence was varied.

Mutant BRAF V600E, Mutant BRAF V600R, and wild type BRAF plasmid DNAs were prepared as described in Example 6.

A. Varying BRAF V600R

Each of six samples contained 10,000 copies of the BRAF wild-type target sequence (SEQ ID No. 45), 1,000 copies of the BRAF V600E mutant target sequence (SEQ ID No. 43), and differing amounts (2,500; 625; 156; 39; 10; or 0 copies) of the BRAF V600R mutant target sequence (SEQ ID No. 44).

PCR amplifications were performed as described in Example 9 with the following modifications to the primers and to the molecular beacon probes. The reactions contained 60 nM of each of BRAF SuperSelective primer BRAF V600E 32-30-10/9-6:1:1 (SEQ ID No. 17), BRAF V600R 32-30-12/9-5:2:1 (SEQ ID No. 20), BRAF Wild Type 32-30-10/9-8:0:0 (SEQ ID No. 22), 1,500 nM of the BRAF reverse primer (SEQ ID No. 23), 300 nM of Molecular Beacon V600E (SEQ ID No. 38), 300 nM of Molecular Beacon V600R (SEQ ID No. 39), and 300 nM of Molecular Beacon Wild Type (SEQ ID No. 40).

Figure 12:
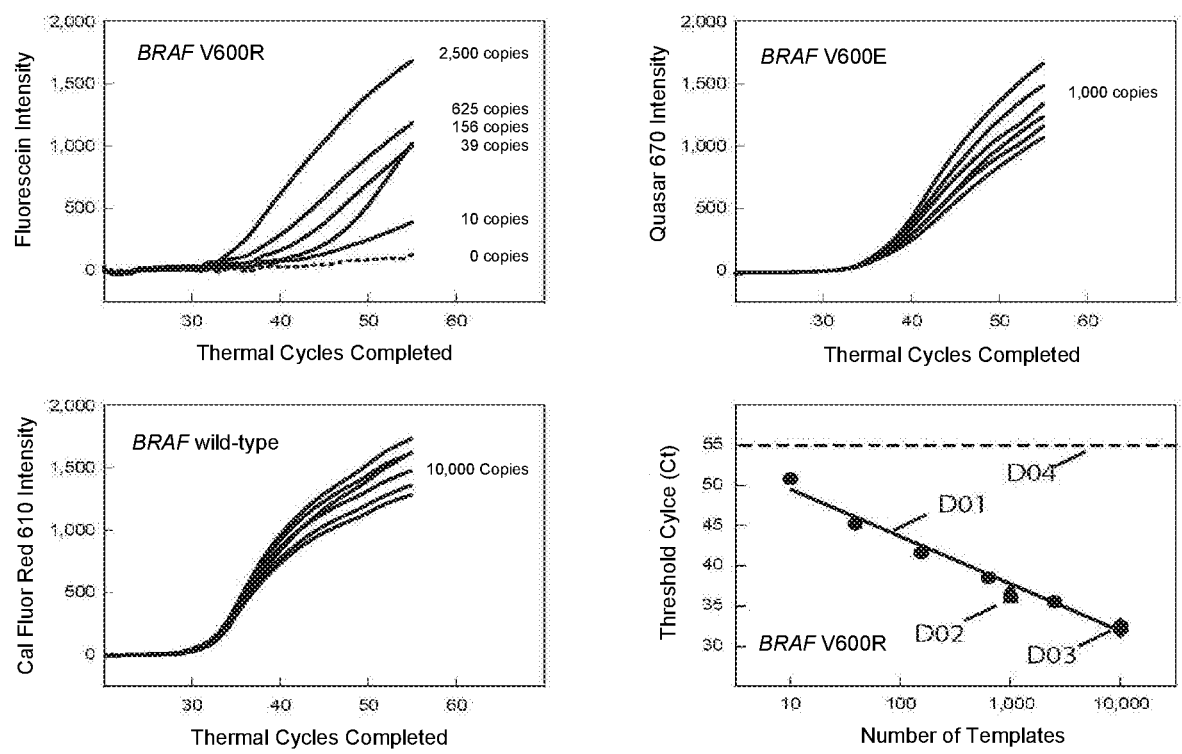
FIG. 12 shows the real-time fluorescence results and a graph of $C_T$ versus the log of starting number of target sequences for PCR assays in Example 10A in which a related wild-type sequence was also amplified and detected.

The results are shown in FIG. 12. Three of the panels are graphs of real-time fluorescence curves, fluorescence intensity versus the number of thermal cycle completed. The top left graph shows the curves of fluorescence from Molecular Beacon V600R for the six samples that contained different amounts of the BRAF V600R mutant target sequence. The top right graph shows the curves of fluorescence from Molecular Beacon V600E for the 1,000 copies of the BRAF V600E target sequence contained in each of those six samples. The lower left graph shows the curve of fluorescence from Molecular Beacon Wild Type for the 10,000 copies of the BRAF wild-type sequence contained in each of those six samples. The lower right panel is a graph of the $C_T$ values obtained from the real-time curves as a function of the logarithm of the number of templates present in each reaction. The solid circles are the $C_T$ values for BRAF V600R; solid triangles, D02, are the $C_T$ values for BRAF V600E; and solid diamonds, D03, are the $C_T$ values for BRAF wild-type. Line D01 is a linear correlation fit to the BRAF V600R data. Dashed line D04 identifies the $C_T$ value for the amplification initiated with 10,000 BRAF wild-type templates, 1,000 BRAF V600E templates, and no BRAF V600R templates.

B. Varying BRAF V600E

Each of six samples contained 10,000 copies of the BRAF wild-type target sequence (SEQ ID No. 45), 1,000 copies of the BRAF V600R mutant target sequence (SEQ ID No. 44), and differing amounts (2,500; 625; 156; 39; 10; or 0 copies) of the BRAF V600E mutant target sequence (SEQ ID No. 43). Amplification reaction mixtures and PCR amplifications were as reported in part A above.

Figure 13:
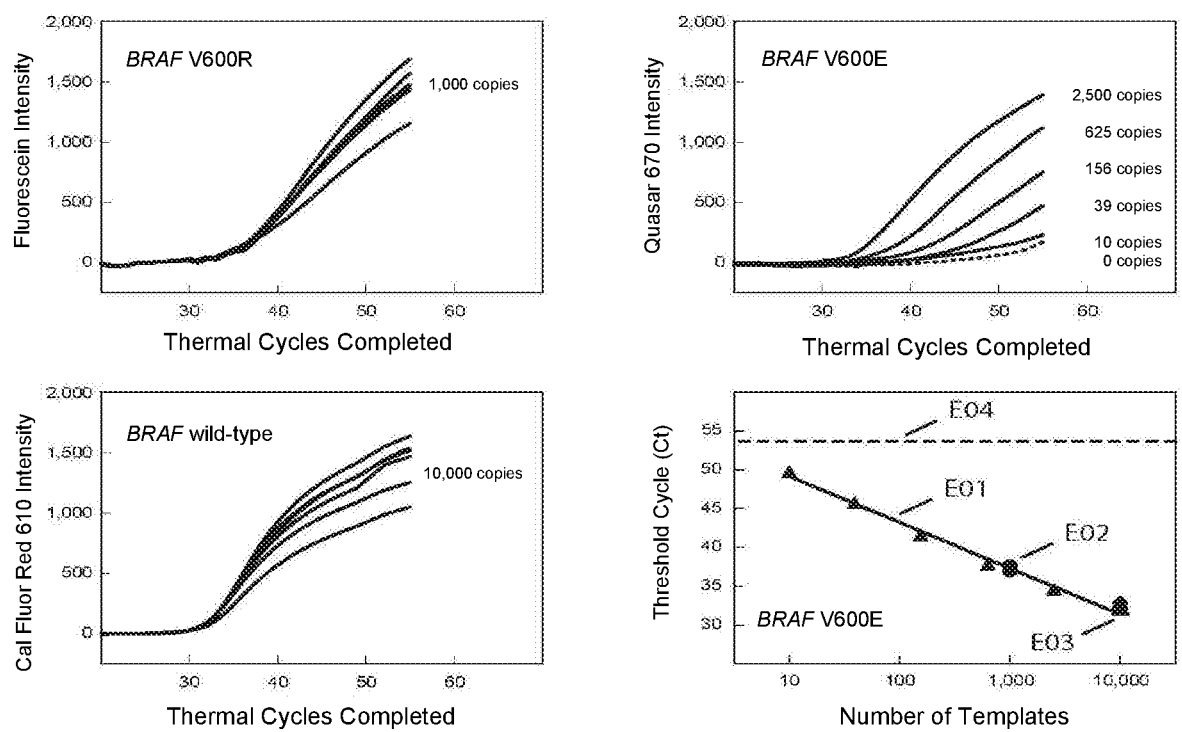
FIG. 13 shows the real-time fluorescence results and a graph of $C_T$ versus the log of starting number of target sequences for PCR assays in Example 10B in which a related wild-type sequence was also amplified and detected.

The results are shown in FIG. 13. Three of the panels are graphs of real-time fluorescence curves, fluorescence intensity versus the number of thermal cycles completed. The top right graph shows the curves of fluorescence from Molecular Beacon V600E for the six samples that contained different amounts of the BRAF V600E mutant target sequence. The top left graph shows the curves of fluorescence from Molecular Beacon V600R for the 1,000 copies of the BRAF V600R target sequence contained in each of those six samples. The lower left graph shows the curve of fluorescence from Molecular Beacon Wild Type for the 10,000 copies of the BRAF wild-type sequence contained in each of those six samples. The lower right panel is a graph of the $C_T$ values obtained from the real-time curves as a function of the logarithm of the number of templates present in each reaction. The solid triangles are the $C_T$ values for BRAF V600E; solid circles, E02, are the $C_T$ values for BRAF V600R; and solid diamonds, E03, are the $C_T$ values for BRAF wild-type. Line E01 is a linear correlation fit to the BRAF V600E data. Dashed line E04 identifies the $C_T$ value for the amplification initiated with 10,000 BRAF wild-type templates, 1,000 BRAF V600R templates, and no BRAF V600E templates.

Example 11. Length of Foot with TMAC in Different Concentrations

We investigated the effect of differing concentrations of TMAC in assays for mutation BRAF V600E utilizing a SuperSelective primer having a preferred design for an assay without TMAC (32-24-14/14-6:1:1) and a SuperSelective primer having a longer foot sequence (32-24-14/14-8:1:1).

A. SuperSelective Primer 32-24-14/14-6:1:1

All of the reactions were performed in 30-μl volumes containing 50 mM KCl, 2.5 mM MgCl$_2$, 20 mM Tris-HCl (pH 8.3), 250 μM dATP, 250 μM dCTP, 250 μM dGTP, 250 μM dTTP, 1.5 units of Platinum Taq DNA polymerase (ThermoFisher Scientific), 0.5% Tween 20 (Sigma), 300 nM of a Quasar® 670-labeled BRAF V600E-specific molecular beacon (SEQ ID No. 38) for monitoring amplicon abundance during the annealing stage of each thermal cycle. The thermal cycling program after an initial 2 min at 95° C., was 65 repetitions of 15 sec at 95° C., 20 sec at 60° C., and 20 sec at 72° C.

Reaction mixtures contained either 1,000 copies of BRAF V600E mutant target sequence and 1,000,000 copies of the related BRAF wild-type sequence, or only 1,000,000 copies of the related BRAF wild-type sequence. In the different reaction mixtures the amount of TMAC varied as follows: 0 mM, 30 mM, 50 mM, 70, mM, or 100 mM. Primer concentrations were 60 nM BRAF V600E forward primer and 500 nM BRAF conventional reverse primer.

Primer sequences (5'-tag sequence and bridge sequence underlined; interrogating nucleotide in bold):

```
SuperSelective forward primer 32-24-14/14-6:1:1
                                        (SEQ ID No. 43)
5'-ACCTGCCGTCAACACGTGCGCAGTAGACCATCCAGACAACTGTTCAA
ACTGATGGGCAAACACATCATCCGATTTCTC-3'

BRAF V600E conventional reverse primer
                                        (SEQ ID No. 44)
5'-ATAGGTGATTTTGGTCTAGC-3'
```

The results are shown in FIG. 14. Each of the five panels indicates the amount of TMAC used and presents two real-time curves of fluorescence intensity versus PCR cycle number. Curves 1401, 1403, 1405, 1407, and 1409 are assays initiated with 1,000 copies of BRAF V600E mutant targets and 1,000,000 copies of BRAF wild-type targets; and curves 1402, 1404, 1406, 1408, and 1410 are assays initiated with only 1,000,000 copies of BRAF wild-type targets. The instrument-calculated Ct values for the curves were: curve 1401, 40.6; curve 1402, 52.1; curve 1403, 39.3; curve 1404, 56.3; curve 1405, 40.0; curve 1406, N/A; curve 1407, 45.1; curve 1408, N/A; curve 1409, N/A, and curve 1410, N/A. Based on those values, the calculated values for $\Delta C_T$ through 65 PCR cycles ($C_T$ with wild-type only minus $C_T$ with mutant also present) varied with TMAC concentration: curves 1401 and 1402, 11.5; curves 1403 and 1404, 17.0. For curves 1405 and 1406, and for curves 1407 and 1408, there is no $\Delta C_T$, because at least one curve of each pair had no $C_T$.

B. SuperSelective Primer 32-24-14/14-8:1:1

Reaction mixtures and PCR cycling were as set forth in part A above, as was the reverse primer and the molecular beacon probe. The sequence of the SuperSelective BRAF V600E forward primer was different. Its sequence (5'-tag sequence and bridge sequence underlined; interrogating nucleotide in bold) was:

```
                                        (SEQ ID No. 45)
5'-ACCTGCCGTCAACACGTGCGCAGTAGACCATCTCCAGACAACTGTTC
AAACTGATGTTCAAACACAATCAGAGATTTCTC-3'
```

The results are shown in FIG. 15. Each of the five panels indicates the amount of TMAC used and presents two real-time curves of fluorescence intensity versus PCR cycle number. Curves 1501, 1503, 1505, 1507, and 1509 are assays initiated with 1,000 copies of BRAF V600E mutant targets and 1,000,000 copies of BRAF wild-type target; and curves 1502, 1504, 1506, 1508, and 1510 are assays initiated with only 1,000,000 copies of BRAF wild-type targets. The instrument-calculated Ct values for the curves were: curve 1501, 44.9; curve 1502, 47.1; curve 1503, 42.7; curve 1504, 47.9; curve 1505, 41.6; curve 1506, 52.9; curve 1507, 42.6; curve 1508, 59.0; curve 1509, N/A, and curve 1510, N/A. Based on those values, the calculated values for $\Delta C_T$ through 65 PCR cycles ($C_T$ with wild-type only minus $C_T$ with mutant also present) varied with TMAC concentration: curves 1501 and 1502, 2.2; curves 1503 and 1504, 5.2; curves 1505 and 1506, 11.3; curves 1507 and 1508, 16.4.

Example 12. The 8:1:1 Foot Sequence and Different Target Sequence Concentrations in Pseudo-Liquid Biopsy Samples We performed a series of assays using the SuperSelective primer described in Example 11 having an 8:1:1 foot sequence (SEQ ID No. 45) and the same conventional reverse primer (SEQ ID No. 44). The reaction mixtures contained 40,000 copies of the BRAF wild-type sequence and differing amounts of BRAF V600E mutant target sequence: 0; 10; 100; 1,000; or 10,000 copies. Reaction mixtures were otherwise as described in Example 11. PCR amplification and detection were as described in Example 11.

The results are shown in FIG. 16. The concentration of TMAC is indicated in the panels—either no TMAC (three left panels) or 70 mM TMAC (three right panels). Each panel presents real-time fluorescence readings from the molecular beacon probe, that is, fluorescence intensity as a function of PCR thermal cycle. Curves 1601, 1602 and 1603 are from reactions with no TMAC and 10,000, 1,000, and 100 copies of the mutant target sequence, respectively. Multiple curves 1604 are from repeat reactions with no TMAC and 10 copies of the mutant target sequence. Multiple curves 1605 are from repeat reactions with no TMAC and no copies of the mutant target sequence. Curves 1606, 1607 and 1608 are from reactions with 70 mM TMAC and 10,000, 1,000, and 100 copies of the mutant target sequence, respectively. Multiple curves 1609 are from repeat reactions with 70 mM TMAC and 10 copies of the mutant target sequence. Multiple curves 1610 are from repeat reactions with 70 mM TMAC and no copies of the mutant target sequence.

Instrument-calculated $C_T$ values for panels in the left column were as follows: curve 1601, 40.2; curve 1602, 44.7; curve 1603, 48.6; five individual curves 1604: 53.6, 50.0, 52.4, 50.9 and 50.1; five individual curves 1605: 52.9, 53.8, 61.0, 61.7 and 56.3. Values for panels in the right column were as follows: curve 1606, 37.8; curve 1607, 42.4; curve 1608, 47.2; five individual curves 1609: 51.1, 51.5, 54.5, 52.4 and 50.3; five individual curves 1610: all N/A. With no TMAC the highest $C_T$ for a reaction with 10 mutant copies was 53.6, and the lowest $C_T$ for a reaction with no mutant copies was 52.9. With 70 mM TMAC the highest $C_T$ for a reaction with 10 mutant copies was 54.5, and the lowest $C_T$ for a reaction with no mutant copies was N/A, that is, not measurable within 65 cycles of hybridization and extension.

Example 13. Detection of Mutants in Pseudo-Liquid Biopsy Samples

We performed a series of assays using SuperSelective primer EGFR G719S 32-24-18/14-7:1:0, conventional reverse primer EGFR G719S, and Molecular Beacon SEQ ID No. 38. Reaction mixtures contained 40,000 copies of the EGFR wild-type sequence and differing amounts of EGFR G719S mutant target sequence: 0; 4; 40; 400; 4,000; or 40,000 copies. Reaction mixtures were otherwise as described in Example 11, except that the TMAC concentration was 50 mM rather than 70 mM. PCR amplification and detection were as described in Example 11.

Primer sequences (5'-tag sequence and bridge sequence underlined; interrogating nucleotide in bold):

SuperSelective forward primer 32-24-18/14-7:1:0
(SEQ ID No. 46)
5'-ACCTGCCGTCAACACGTGCGCAGTAGACCATCTGAGGATCTTGAAGG
AAACTGAATCACTCTCAATTGAGCACCAGTGCTGA-3'

EGFR G719S conventional reverse primer
(SEQ ID No. 47)
5'-CACCGTGCCGAACGCA-3'

The results, shown in FIG. 17, are plotted as a graph of threshold cycle ($C_T$) versus the starting number of mutant target sequences in the reaction mixture (this axis is logarithmic). Line 1701 is a straight line fit to the $C_T$ values from the reaction mixtures containing the mutant target sequence in the amounts shown. Those instrument-calculated $C_T$'s were: for 40,000 copies, 34.6; for 4,000 copies, 37.6; for 400 copies, 40.9; for 40 copies, 46.8; and for 4 copies, 48.7. Dotted line 1702 is the $C_T$ value (54.9) for the reaction mixture containing only the corresponding wild-type sequence.

Example 14. Effect of TMAC Concentration with Different Bubbles

We performed a series of real-time PCR assays using a SuperSelective primer with a large, 18-nucleotide long bridge sequence that (in combination with a large, 18-nucleotide long intervening sequence) produced a large, 40-nucleotide circumference, symmetric bubble: SuperSelective primer BRAF V600E 32-24-18/18-8:1:1 and different concentrations of TMAC (0 mM, 20 mM, 40 mM, and 60 mM). We also performed a parallel series of real-time PCR assays using a SuperSelective primer with a smaller, 10-nucleotide long bridge sequence that (in combination with a smaller, 14-nucleotide long intervening sequence) produced a smaller, 28-nucleotide circumference, asymmetric bubble: SuperSelective primer BRAF V600E 32-24-10/14-8:1:1. For each TMAC concentration there were two assays with each primer: one starting with 100,000 copies of the BRAF V600E mutant target sequence, and one starting with 100,000 copies of the corresponding BRAF V600E wild-type sequence. Except for the primer sequences and the stated TMAC and BRAF V600E concentrations, the reaction mixtures were as described in Example 11. PCR amplification and detection were as described in Example 11. The primer sequences (5'-tag sequence and bridge sequence underlined; interrogating nucleotide in bold) were:

SuperSelective forward primer BRAF V600E 32-24-18/
18-8:1:1
(SEQ ID No. 48)
5'-ACCTGCCGTCAACACGTGCGCAGTAGACCATCTGGATCCAGACAACT
GTTCAAACTTTCAAACGCATACAATCAGAGATTTCTC-3'

SuperSelective forward primer BRAF V600E 32-24-10/
14-8:1:1
(SEQ ID No. 49)
5'-ACCTGCCGTCAACACGTGCGCAGTAGACCATCTCCAGACAACTGTTC
AAACTGATGTTCACCATCAGAGATTTCTC-3'

BRAF V600E conventional reverse primer
(SEQ ID NO. 50)
5'-TTCTTCATGAAGACCTCACA-3'

The following $C_T$'s and $\Delta C_T$'s were obtained:

TABLE 7

| | | Threshold Cycles ($C_T$) Observed for Reactions Containing Primers that Form Different Size Bubble | | |
|---|---|---|---|---|
| Primer | TMAC Conc. (mM) | $10^5$ Mutant Templates | $10^5$ Wild-type Templates | $\Delta C_T$ |
| 32-24-18/18-8:1:1 | 0 | 32.5 | 44.1 | 11.6 |
| 32-24-18/18-8:1:1 | 20 | 29.8 | 46.7 | 16.9 |
| 32-24-18/18-8:1:1 | 40 | 31.8 | 54.4 | 22.6 |
| 32-24-18/18-8:1:1 | 60 | 32.7 | 58.5 | 26.8 |
| 32-24-10/14-8:1:1 | 0 | 33.7 | 45.1 | 11.4 |
| 32-24-10/14-8:1:1 | 20 | 33.8 | 46.5 | 12.7 |
| 32-24-10/14-8:1:1 | 40 | 32.9 | 46.0 | 13.1 |
| 32-24-10/14-8:1:1 | 60 | 32.7 | 49.7 | 17.0 |

The values of $\Delta C_T$ in Table 7 are plotted against TMAC concentration in FIG. 18, where line 1801 is fitted to the $\Delta C_T$ values obtained with primer 32-24-18/18-8:1:1, and line 1802 is fitted to the $\Delta C_T$ values obtained with primer 32-24-10/14-8:1:1.

Example 15. Position of the Interrogating Nucleotide with TMAC in Different Concentrations We investigated the effect of differing concentrations of TMAC in assays for mutation BRAF V600E utilizing a SuperSelective primer having a foot sequence ten-nucleotides long and a 3'-terminal interrogating nucleotide (9:1:0) compared to the effect of using instead a SuperSelective primer also having a foot sequence ten nucleotides long but having a 3'-penultimate interrogating nucleotide (8:1:1).

A. Superselective Primer 32-24-14/14-9:1:0

All of the reactions were performed in 30-μl volumes containing 50 mM KCl, 2.5 mM $MgCl_2$, 20 mM Tris-HCl (pH 8.3), 250 µM dATP, 250 µM dCTP, 250 µM dGTP, 250 µM dTTP, 1.5 units of Platinum Taq DNA polymerase (ThermoFisher Scientific), 0.5% Tween 20 (Sigma), 300 nM of a Quasar® 670-labeled BRAF V600E-specific molecular beacon (SEQ ID No. 38) for monitoring amplicon abundance during the annealing stage of each thermal cycle. The thermal cycling program after an initial 2 min at 95° C., was 65 repetitions of 15 sec at 95° C., 20 sec at 60° C., and 20 sec at 72° C.

Reaction mixtures contained either 4,000 copies of BRAF V600E mutant target sequence and 400,000 copies of the related BRAF wild-type sequence, or only 400,000 copies of the related BRAF wild-type sequence. In the different reaction mixtures the amount of TMAC varied as follows: 0 mM, 10 mM, 20 mM, 30, mM, 40 mM, or 50 mM. Primer concentrations were 60 nM BRAF V600E forward primer and 500 nM BRAF conventional reverse primer.

Primer sequences (5'-tag sequence and bridge sequence underlined; interrogating nucleotide in bold):

```
SuperSelective forward primer 32-24-14/14-9:1:0
                                           (SEQ ID No. 51)
5'-ACCTGCCGTCAACACGTGCGCAGTAGACCATCATCCAGACAACTGTT
CAAACTGATTCAAACACAATACCCGAGATTTCT-3'

BRAF V600E conventional reverse primer
                                           (SEQ ID NO. 50)
5'-TTCTTCATGAAGACCTCACA-3'
```

B. SuperSelective Primer 32-24-14/14-8:1:1 (SEQ ID No. 45)

Reaction mixtures and PCR cycling were as set forth in part A above, except for the SuperSelective BRAF V600E forward primer, which was SEQ ID No. 45.

The following $C_T$'s and $\Delta C_T$'s were obtained.

TABLE 8

| Primer | TMAC Conc. (mM) | Threshold Cycles ($C_T$) Observed | | |
|---|---|---|---|---|
| | | $4 \times 10^3$ Mutant plus $4 \times 10^5$ Wild-type Templates | $4 \times 10^5$ Wild-type Templates | $\Delta C_T$ |
| 32-24-14/14-8:1:1 | 0 | 42.4 | 43.6 | 1.2 |
| 32-24-14/14-8:1:1 | 10 | 42.3 | 45.8 | 3.5 |

TABLE 8-continued

| Primer | TMAC Conc. (mM) | Threshold Cycles ($C_T$) Observed | | |
|---|---|---|---|---|
| | | $4 \times 10^3$ Mutant plus $4 \times 10^5$ Wild-type Templates | $4 \times 10^5$ Wild-type Templates | $\Delta C_T$ |
| 32-24-14/14-8:1:1 | 20 | 42.2 | 44.8 | 2.6 |
| 32-24-14/14-8:1:1 | 30 | 40.6 | 44.5 | 3.9 |
| 32-24-14/14-8:1:1 | 40 | 40.9 | 46.3 | 5.4 |
| 32-24-14/14-8:1:1 | 50 | 40.4 | 47.9 | 7.5 |
| 32-24-14/14-9:1:0 | 0 | 43.8 | 48.0 | 4.2 |
| 32-24-14/14-9:1:0 | 10 | 41.3 | 48.8 | 7.5 |
| 32-24-14/14-9:1:0 | 20 | 40.8 | 49.7 | 8.9 |
| 32-24-14/14-9:1:0 | 30 | 39.6 | 54.3 | 14.7 |
| 32-24-14/14-9:1:0 | 40 | 40.2 | 56.9 | 16.7 |
| 32-24-14/14-9:1:0 | 50 | 39.7 | N/A | N/A |

The values of $C_T$ for assays with SuperSelective primer 32-24-14/14-9:1:0 in Table 8 are plotted against TMAC concentration in FIG. 19, where line 1901 is for samples containing only BRAF wild-type sequences, and line 1902 is for samples containing BRAF wild-type sequences plus BRAF V600E mutant target sequences. The values of $C_T$ for assays with SuperSelective primer 32-24-14/14-8:1:1 in Table 8 are plotted against TMAC concentration in FIG. 20, where line 2001 is for samples containing only BRAF wild-type sequences, and line 2002 is for samples containing BRAF wild-type sequences plus BRAF V600E mutant target sequences. The values of $\Delta C_T$ in Table 8 are plotted against TMAC concentration in FIG. 21, where line 2101 is fitted to the $\Delta C_T$ values obtained with primer 32-24-14/14-9:1:0, and line 2102 is fitted to the $\Delta C_T$ values obtained with primer 32-24-14/14-8:1:1.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

The invention claimed is:

1. A multiplex assay method for amplifying and detecting in a sample copies of each of at least two different closely related, intended rare mutant DNA target sequences in the presence of copies of a wild-type allele of the mutant DNA target sequences ("a related wild-type DNA target sequence"), where the mutant DNA target sequences differ from each other and from the wild-type DNA target sequence by as little as a single-nucleotide polymorphism, comprising:
  (a) preparing a non-symmetric primer-dependent amplification reaction mixture that includes the sample, a DNA polymerase, deoxyribonucleoside triphosphates, other reagents required for amplification, 10-70 mM tetramethylammonium chloride (TMAC), a distinguishably labeled homogeneous fluorescence detection probe that is specific for an amplification product of each rare mutant DNA target sequence, an excess concentration of a reverse primer for the closely related mutant target sequences, and for each intended rare mutant target sequence, a limiting concentration of a unique multi-part primer:
  wherein the sequence of each multi-part primer comprises, in the 5' to 3' direction, the following three contiguous DNA sequences that are copied by extension of the reverse primer:
  an anchor DNA sequence that is sufficiently long so that it is able to hybridize with the closely related mutant DNA target sequences and with the related wild-type target sequence during primer annealing;
  a unique bridge DNA sequence at least six nucleotides long that does not hybridize during primer annealing to the unique multi-part primer's intended DNA target sequence, to any other closely related mutant target DNA sequences, or to the related wild-type DNA target sequence during primer annealing; and
  a unique foot DNA sequence that is 7 to 14 nucleotides long and that is perfectly complementary to the intended DNA target sequence but mismatches each other mutant target sequence and the related wild-type DNA sequence by one or more nucleotides, at least one of which is the 3'-terminal nucleotide or the 3'-penultimate nucleotide, wherein all of the following requirements are met:
  (i) if the anchor DNA sequence and the foot DNA sequence of the multi-part primer are both hybridized to its intended target DNA sequences thereby creating a primer-target hybrid, the primer-target hybrid comprises in the 5' to 3' direction of the multi-part primer: an anchor-target hybrid, a bubble, and a foot-target hybrid, said bubble having a circumference of 24 to 40 nucleotides and being formed by an intervening DNA sequence in the target DNA sequence that is at least eight nucleotides long and does not hybridize to the primer's bridge DNA sequence during primer annealing;
  (ii) the bubble isolates the foot-target hybrid from the anchor-target hybrid;
  (iii) the multi-part primer that has generated an amplicon strand has bridge and foot DNA sequences that are perfectly complementary to the amplicon strand's complementary strand; and
  (b) repeatedly cycling the reaction mixture to amplify the closely related rare mutant target DNA sequences present in the sample and detecting the presence of those DNA sequences by measuring the intensity of fluorescence from each distinguishably labeled probe by real-time or end-point detection.

2. The method according to claim 1 wherein cycling is temperature cycling in a polymerase chain reaction (PCR) method.

3. The method according to claim 2 wherein a CT value for one target DNA sequence represents the same number of starting templates as it does for any other target DNA sequence.

4. The method according to claim 1, wherein for at least one intended rare target sequence the multi-part primer includes a 5'-tag sequence that is not complementary to any target sequence, that is unique for each target sequence or target-sequence group that is to be separately identified, and whose complement in the amplicon strand initiated by the reverse primer is the target of the probe.

5. The method according to claim 1 wherein for at least one intended rare target sequence the target of the probe is the complement of the bridge sequence in the amplicon strand initiated by the reverse primer.

6. The method of claim 5 wherein the foot DNA sequence mismatches the closely related wild-type DNA sequence by one or more nucleotides, and wherein at least one of which is the 3'-terminal nucleotide.

7. The method according to claim 1 that includes amplifying and detecting a reference wild-type DNA sequence, wherein the primer-dependent amplification reaction mixture includes a limiting multi-part primer for, an excess reverse primer for, and a homogeneous fluorescence detection probe for, the reference DNA sequence, wherein the multi-part primer for the reference DNA sequence has the structural limitations described in claim 1, and wherein the length and nucleotide sequence of the bridge DNA sequence of the multi-part primer for the reference DNA sequence are coordinated with those of the multi-part primers for the mutant target sequences so that the difference between the CT value obtained for each mutant target DNA sequence and the CT value obtained for the reference wild-type DNA sequence reflects the abundance of that mutant target DNA sequence relative to the abundance of the reference wild-type DNA sequence, irrespective of the amount of DNA present in the sample.

8. The method according to claim 1, wherein cycling the reaction mixture is performed by an instrument, wherein the number of different target DNA sequences exceeds the number of colors the instrument can separately detect, and wherein multiple different probes are thermospecific hybridization probes having the same fluorophore but the hybrids that they form have different melting temperatures.

9. A multiplexed assay method according to claim 1, wherein amplification and detection are a digital PCR method.

10. A multiplexed assay method according to claim 1, wherein the probes are color-coded molecular beacon probes.

11. The method of claim 1, wherein hybrids formed by the multi-part primer anchor DNA sequences and the mutant target DNA sequences have melting temperatures (Tm's) that are lower than the Tm of hybrids formed by the reverse primer and the mutant target DNA sequences, wherein before step (b) multiple cycles of linear amplification utilizing the reverse primer are performed using a primer annealing temperature at which the reverse primer hybridizes but the multi-part primers are less likely to hybridize, and wherein step (b) is performed using a lower primer annealing temperature at which the multi-part primers and the reverse primer hybridize.

12. The method of claim 1, wherein the foot sequence is 8 to 10 nucleotides long.

13. The method of claim 1, wherein the lengths of the bridge and intervening sequences are unequal, and the bubble is asymmetric.

14. The method of claim 1, wherein non-symmetric primer-dependent amplification reaction mixture includes 10-50 mM TMAC.

15. The method of claim 1, wherein non-symmetric primer-dependent amplification reaction mixture includes 20-50 mM TMAC.

16. The method of claim 1, wherein non-symmetric primer-dependent amplification reaction mixture includes 20-60 mM TMAC.

17. The method of claim 1, wherein non-symmetric primer-dependent amplification reaction mixture includes 30-70 mM TMAC.

* * * * *

SEQUENCE LISTING

```
<160> NUMBER OF SEQ ID NOS: 55

<210> SEQ ID NO 1
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tggtgaaaac accgcagcat gtcacacgag tgagcccgg gcgg            44

<210> SEQ ID NO 2
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 2
ctggtgaaaa caccgcagca tgtcgcacga gtgagccctg ggcgg            45

<210> SEQ ID NO 3
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
actggtgaaa acaccgcagc atgttggagc tgtgagcctt gggcgg           46

<210> SEQ ID NO 4
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
actggtgaaa acaccgcagc atgttgcacg agtgagcctt gggcg            45

<210> SEQ ID NO 5
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tggtgaaaac accgcagcat gtcacacgag tgagccacgg gcggg            45

<210> SEQ ID NO 6
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggtgaaaaca ccgcagcatg tcaaacgagt gagccacagg cgggc            45

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gtgaaaacac cgcagcatgt caaggaagtg agccacaagc gggcc            45

<210> SEQ ID NO 8
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 8
tgaaaacacc gcagcatgtc aagacagact gacccaaacg ggcca            45

<210> SEQ ID NO 9
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tgaaaacacc gcagcatgtc aagacactca gccctgggcg g                41

<210> SEQ ID NO 10
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cgtactggtg aaaacaccgc agcactgacg acaagtgagc cctgggcgg         49

<210> SEQ ID NO 11
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgaaaacacc gcagcatgtc aagacacacg acaagtgagc cctgggcgg         49

<210> SEQ ID NO 12
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggtgaaaaca ccgcagcatg tcaatccaac aagtgagccc tgggcgg           47

<210> SEQ ID NO 13
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tactggtgaa aacaccgcag catggacgac gagccctggg cgg               43

<210> SEQ ID NO 14
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
```
cgtactggtg aaaacaccgc agcactgacg gccctgggcg g                    41

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gcatggtatt ctttctcttc cgca                                      24

<210> SEQ ID NO 16
<211> LENGTH: 95
<212> TYPE: DNA
<213> ORGANISM: Homo sapiens

<400> SEQUENCE: 16
ttctgcatgg tattctttct cttccgcacc cagcagtttg gcccgcccaa aatctgtgat    60
cttgacatgc tgcggtgttt tcaccagtac gttcc                              95

<210> SEQ ID NO 17
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
acctgccgtc aacacgtgcg cagtagacca tcatgaagac ctcacagtaa aaataggtga    60
ttcagaccca acctacagag                                               80

<210> SEQ ID NO 18
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
acctgccgtc aacacgtgcg cagtagacca tcatgaagac ctcacagtaa aaataggtga    60
ttcttaatag acccaaccta cagag                                         85

<210> SEQ ID NO 19
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
acctgccgtc aacacgtgcg cagtagacca tcgacctcac agtaaaaata ggtgattcag    60
acccaaccta cagag                                                    75

<210> SEQ ID NO 20
<211> LENGTH: 82
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 20
acgtgccctc aatacgagcc cccttcacca acatgaagac ctcacagtaa aaataggtga      60
ttaatggacg gaacctacaa gg                                              82

<210> SEQ ID NO 21
<211> LENGTH: 77
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
acgtgccctc aatacgagcc cccttcacca acgacctcac agtaaaaata ggtgattaat      60
ggacggaacc tacaagg                                                    77

<210> SEQ ID NO 22
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
acgacccgac aaccgttgct gcgtactgca tcatgaagac ctcacagtaa aaataggtga      60
ttccacagca cactacagtg                                                 80

<210> SEQ ID NO 23
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
atcagtggaa aaatagcctc aattcttacc atcc                                 34

<210> SEQ ID NO 24
<211> LENGTH: 79
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
acgacccgac aaccgttgct gcgtactgca tcggaacgta ctggtgaaaa caccgcaaat      60
agccgcagat cgatcacag                                                  79

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
catggtattc tttctcttcc gcaccca                                         27

<210> SEQ ID NO 26
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
acctgccgtc aacacgtgcg cagtagacca tcagacctca cagtaaaaat aggtgatcag    60
acccaacgct acaga                                                     75

<210> SEQ ID NO 27
<211> LENGTH: 77
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
acgtgccctc aatacgagcc cccttcacca acagacctca cagtaaaaat aggtgataat    60
ggacggaacg ctacaag                                                   77

<210> SEQ ID NO 28
<211> LENGTH: 88
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
acctgccgtc aacacgtgcg cagtagacca tcatgaagac ctcacagtaa aataggtga    60 ttcaacttaa tagacccaac ctacagag                                       88

<210> SEQ ID NO 29
<211> LENGTH: 88
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
acgtgccctc aatacgagcc cccttcacca acatgaagac ctcacagtaa aataggtga    60 ttacccaata tggacggaac ctacaagg                                       88

<210> SEQ ID NO 30
<211> LENGTH: 88
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
acctgccgtc aacacgtgcg cagtagacca tccatgaaga cctcacagta aaaataggtg    60
atcaacttaa tagacccaac gctacaga                                       88

<210> SEQ ID NO 31
<211> LENGTH: 88

-continued

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
acgtgccctc aatacgagcc cccttcacca accatgaaga cctcacagta aaaataggtg    60
atacccaata tggacggaac gctacaag                                       88

<210> SEQ ID NO 32
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
atgaagacct cacagtaaaa ataggtgatt acctgccgtc aacacgtgcg cagtagacca    60
tcctacagag                                                           70

<210> SEQ ID NO 33
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
atgaagacct cacagtaaaa ataggtgatt acgtgccctc aatacgagcc cccttcacca    60
acctacaagg                                                           70

<210> SEQ ID NO 34
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
agacctcaca gtaaaaatag gtgatcacgt tataagaatt aacgctacag a             51

<210> SEQ ID NO 35
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gacctcacag taaaaatagg tgatacccaa tatagaagga acgctacaag               50

<210> SEQ ID NO 36
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
agacctcaca gtaaaaatag gtgatcacgt tataagaatt aacctacaga g        51

<210> SEQ ID NO 37
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
agacctcaca gtaaaaatag gtgataccca atatagaagg aacctacaag g        51

<210> SEQ ID NO 38
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 38
cgcctgacct gccgtcaaca cgtgcgcagt agaccatcca ggcg                44

<210> SEQ ID NO 39
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 39
cgcctgacgt gccctcaata cgagccccct tcaccaacca ggcg                44

<210> SEQ ID NO 40
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 40
cgcctgacga cccgacaacc gttgctgcgt actgcatcca ggcg                44

<210> SEQ ID NO 41
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 41
ccgctgatag gtgatcacgt tataagaatt aacgccagcg g                   41

<210> SEQ ID NO 42
<211> LENGTH: 39
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 42
ccgtgcaggt gatacccaat atagaaggaa cgcgcacgg                      39

<210> SEQ ID NO 43
<211> LENGTH: 150
<212> TYPE: DNA
<213> ORGANISM: Homo sapiens

<400> SEQUENCE: 43
aatttaatca gtggaaaaat agcctcaatt cttaccatcc acaaaatgga tccagacaac    60
tgttcaaact gatgggaccc actccatcga gatttctctg tagctagacc aaaatcacct   120
atttttactg tgaggtcttc atgaagaaat                                    150

<210> SEQ ID NO 44
<211> LENGTH: 150
<212> TYPE: DNA
<213> ORGANISM: Homo sapiens

<400> SEQUENCE: 44
aatttaatca gtggaaaaat agcctcaatt cttaccatcc acaaaatgga tccagacaac    60
tgttcaaact gatgggaccc actccatcga gatttccttg tagctagacc aaaatcacct   120
atttttactg tgaggtcttc atgaagaaat                                    150

<210> SEQ ID NO 45
<211> LENGTH: 150
<212> TYPE: DNA
<213> ORGANISM: Homo sapiens

<400> SEQUENCE: 45
aatttaatca gtggaaaaat agcctcaatt cttaccatcc acaaaatgga tccagacaac    60
tgttcaaact gatgggaccc actccatcga gatttcactg tagctagacc aaaatcacct   120
atttttactg tgaggtcttc atgaagaaat                                    150

<210> SEQ ID NO 46
<211> LENGTH: 112
<212> TYPE: DNA
<213> ORGANISM: Homo sapiens

<400> SEQUENCE: 46
tttgcctcct tctgcatggt attctttctc ttccgcaccc agcagtttgg ccagcccaaa    60
atctgtgatc ttgacatgct gcggtgtttt caccagtacg ttcctggctg cc           112

<210> SEQ ID NO 47
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
caccgtgccg aacgca                                                    16

<210> SEQ ID NO 48
<211> LENGTH: 84
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48

```
acctgccgtc aacacgtgcg cagtagacca tctggatcca gacaactgtt caaactttca    60
aacgcataca atcagagatt tctc                                           84

<210> SEQ ID NO 49
<211> LENGTH: 76
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
acctgccgtc aacacgtgcg cagtagacca tctccagaca actgttcaaa ctgatgttca    60
ccatcagaga tttctc                                                    76

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ttcttcatga agacctcaca                                                20

<210> SEQ ID NO 51
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
acctgccgtc aacacgtgcg cagtagacca tcatccagac aactgttcaa actgattcaa    60
acacaatacc cgagatttct                                                80

<210> SEQ ID NO 52
<211> LENGTH: 78
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
acctgccgtc aacacgtgcg cagtagacca tccagacaac tgttcaaact gatgggcaaa    60
cacatcatcc gatttctc                                                  78

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ataggtgatt ttggtctagc                                                20

<210> SEQ ID NO 54
<211> LENGTH: 80
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 54
acctgccgtc aacacgtgcg cagtagacca tctccagaca actgttcaaa ctgatgttca        60
aacacaatca gagatttctc                                                   80

<210> SEQ ID NO 55
<211> LENGTH: 82
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
acctgccgtc aacacgtgcg cagtagacca tctgaggatc ttgaaggaaa ctgaatcact        60
ctcaattgag caccagtgct ga                                                82
```